US011447548B2

(12) United States Patent
Van Hooren et al.

(10) Patent No.: US 11,447,548 B2
(45) Date of Patent: Sep. 20, 2022

(54) IMMUNOTOXINS, FORMULATIONS THEREOF AND THEIR USE IN MEDICINE

(71) Applicant: Xenikos B.V., Nijmegen (NL)

(72) Inventors: Henricus Gerardus Van Hooren, Nijmegen (NL); Maarten Jaap Frijlink, Nijmegen (NL); Ypke Vincentius Johannes Maria Van Oosterhout, Nijmegen (NL)

(73) Assignee: Xenikos B.V., Nijmegen (NL)

( * ) Notice: Subject to any disclaimer, the term of this patent is extended or adjusted under 35 U.S.C. 154(b) by 0 days.

(21) Appl. No.: 16/759,952

(22) PCT Filed: Oct. 31, 2018

(86) PCT No.: PCT/EP2018/079860
§ 371 (c)(1),
(2) Date: Apr. 28, 2020

(87) PCT Pub. No.: WO2019/086534
PCT Pub. Date: Sep. 5, 2019

(65) Prior Publication Data
US 2020/0407443 A1    Dec. 31, 2020

(30) Foreign Application Priority Data
Oct. 31, 2017    (GB) ...................................... 1717966

(51) Int. Cl.
| C07K 16/28 | (2006.01) |
| A61K 47/68 | (2017.01) |
| A61P 37/06 | (2006.01) |
| A61K 9/08 | (2006.01) |
| A61K 9/19 | (2006.01) |
| A61K 47/18 | (2017.01) |
| A61K 47/26 | (2006.01) |

(52) U.S. Cl.
CPC ............ *C07K 16/2809* (2013.01); *A61K 9/08* (2013.01); *A61K 9/19* (2013.01); *A61K 47/183* (2013.01); *A61K 47/26* (2013.01); *A61K 47/6827* (2017.08); *A61K 47/6849* (2017.08); *A61P 37/06* (2018.01)

(58) Field of Classification Search
CPC ............ C07K 16/2809; A61K 47/6827; A61K 47/6849; A61K 9/08; A61K 9/19; A61K 47/183; A61K 47/26; A61P 37/06
See application file for complete search history.

(56) References Cited

U.S. PATENT DOCUMENTS

| 2006/0051355 | A1* | 3/2006 | van Oosterhout | A61K 47/6827 424/183.1 |
| 2008/0233128 | A1 | 9/2008 | Krause | |
| 2009/0022738 | A1* | 1/2009 | Hofmeister | A61P 43/00 424/173.1 |
| 2009/0041797 | A1 | 2/2009 | Davis et al. | |
| 2010/0209434 | A1* | 8/2010 | Bishop | A61P 1/04 424/158.1 |
| 2016/0106844 | A1* | 4/2016 | Bañado | A61K 47/26 424/134.1 |

FOREIGN PATENT DOCUMENTS

| EP | 0 945 139 A1 | 9/1999 |
| EP | 1066058 B1 | 12/2003 |
| WO | WO 93/11161 A1 | 6/1993 |
| WO | WO 94/13804 A1 | 6/1994 |
| WO | WO 98/55150 A1 | 12/1998 |
| WO | WO 2007/124299 A2 | 11/2007 |

OTHER PUBLICATIONS

Broers et al. "Increased transplant-related morbidity and mortality in CMV-seropositive patients despite highly effective prevention of CMV disease after allogeneic T-cell-depleted stem cell transplantation", (Blood. Apr. 1, 2000;95(7):2240-5) (Year: 2000).*
Sakamoto et al. "Quantification of Epstein-Barr Virus DNA is Helpful for Evaluation of Chronic Epstein-Barr Virus Infection", (Tohoku J. Exp. Med., 012, 227, 307-331). (Year: 2012).*
Reusser et al., "Cytotoxic T-Lymphocyte Response to Cytomegalovirus After Human Allogeneic Bone Marrow Transplantation: Pattern of Recovery and Correlation With Cytomegalovirus Infection and Disease", Blood. 1991;78:1373 (Year: 1991).*
Rezvani et al. "Serum albumin level predicts survival of patients with gastrointestinal acute graft-versus-host disease after allogeneic stem cell transplantation", (Biol Blood Marrow Transplant. Nov. 2011;17(11):1594-601). (Year: 2014).*
Abdelhakim Haitham et al. "Role of [alpha] [beta] T Cell Depletion in Prevention of Graft versus Host Disease", Biomedicines, 2017, 5(35), pp. 1-14.
Andersen Jan Terje et al., "Cross-species binding analyses of mouse and human neonatal Fc receptor show dramatic differences in immunoglobulin G and albumin binding," J. Biol. Chem., Feb. 12, 2010, 285(7), 4826-4836.

(Continued)

*Primary Examiner* — Amy E Juedes
*Assistant Examiner* — Peter Johansen
(74) *Attorney, Agent, or Firm* — Cooley LLP; Matthew Pavao

(57) ABSTRACT

The present invention provides a composition comprising a first antibody molecule that specifically recognizes CD3 and a second antibody molecule that specifically recognizes CD7, for use in a method of treatment, or preventative treatment of viral infection or viral reactivation in a mammalian subject undergoing immunomodulatory treatment, wherein the first and second antibody molecules are each provided with a toxic moiety. Also provided is a method of treating a mammalian subject having, or being at risk of developing, chronic Graft versus Host disease (cGVHD). Also provided is a related pharmaceutical composition.

25 Claims, 16 Drawing Sheets
Specification includes a Sequence Listing.

(56) References Cited

OTHER PUBLICATIONS

Alho Ac et al., "Unbalanced recovery of regulatory and effector T cells after allogeneic stem cell transplantation contributes to chronic GVHD," Blood, Feb. 4, 2016, 127, 646-657.
Amlot P.L. et al., "A phase I study of an anti-CD22-deglycosylated ricin A chain immunotoxin in the treatment of B-cell lymphomas resistant to conventional therapy," Blood, Nov. 1, 1993, 82(9), 2624-2633.
Antin Joseph H., T-cell depletion in GVHD: less is more? BLOOD, Jun. 9, 2011, 117(23), 6061-6162.
Arai Sally et al., "Poor outcome in steroid-refractory graft-versus-host disease with antithymocyte globulin treatment," Biol. Blood Marrow Transplant, 2002, 8, 155-160.
Bacigalupo Andrea et al., "Antithymocyte globulin for graft-versus-host disease prophylaxis in transplants from unrelated donors: 2 randomized studies from Gruppo Italiano Trapianti Midollo Osseo (GITMO)" Blood, Nov. 15, 2001, 98(10), 2942-2947.
Blazar Bruce R. et al., "Advances in graft-versus-host disease biology and therapy." Nature reviews. Immunology, Jun. 2012, 12, 443-458.
Busca Alessandro et al., "In-vivo or ex-vivo T cell depletion or both to prevent graft-versus-host disease after hematopoietic stem cell transplantation", Expert Opinion on Biological Therapy, 2017, 1-15.
Byers Vera S. et al., "Use of an anti-pan T-lymphocyte ricin a chain immunotoxin in steroid-resistant acute graft-versus-host disease," Blood, Apr. 1, 1990, 75(7), 1426-1432.
Bryant John et al., "Incorporating toxicity considerations into the design of two-stage phase II clinical trials," Biometrics, Dec. 1995, 51, 1372-1383.
Calmettes Claire et al., "Risk Factors for Steroid-Refractory Acute Graft-versus-Host Disease after Allogeneic Stem Cell Transplantation from Matched Related or Unrelated Donors." Biol. Blood Marrow Transplant., 2015, 21, 860-865.
Castelletti et al., "Peptide analogues of a T-cell epitope of ricin toxin A-chain prevent agonist-mediated human T-cell response," International Immunology, 2005, 17(4), 365-372.
Chen Yi-Bin et al., "Phase 1 multicenter trial of brentuximab vedotin for steroid-refractory acute graft-versus-host disease," Blood, Jun. 15, 2017, 129(24), 3256-3261.
Clinical Trials Identifier: NCT02027805, "Safety and Efficacy Study of T-Guard to Treat Steroid-resistant Acute GVHD," Jun. 6, 2017, 1-6.
Conry Robert M. et al., "Phase I trial of an anti-CD19 deglycosylated ricin A chain immunotoxin in non-Hodgkin's lymphoma: effect of an intensive schedule of administration," Journal of Immunotherapy, 1995, 18(4), 231-241.
Crews Jennie R., et al., "A combination of two immunotoxins exerts synergistic cytotoxic activity against human breast-cancer cell lines," Int. J. Cancer, 1992, 51, 772-779.
Cousens L.P. et al., "In silico high throughput pre-clinical determination of monoclonal antibody immunogenicity," Institute for Immunology and Informatics, University of Rhode Island, 2013, 1 page.
Dean Scott G. et al., "Cell surface density of p185 (c-erbB-2) determines susceptibility to anti-p185 (c-erbB-2)—ricin A chain (RTA) immunotoxin therapy alone and in combination with anti-p170 (EGFR)-RTA in ovarian cancer cells," Clin. Cancer Res., Oct. 1998, 4, 2545-2550.
Deeg Joachim H. et al., "How I treat refractory acute GVHD," Blood, May 15, 2007, 109(10), 4119-4126.
De Pauw B. et al., "Revised definitions of invasive fungal disease from the European Organization for Research and Treatment of Cancer/Invasive Fungal Infections Cooperative Group and the National Institute of Allergy and Infectious Diseases Mycoses Study Group (EORTC/MSG) Consensus Group." Clin. Infect Dis, Jun. 15, 2008, 46, 1831-1821.
Derocq Jean-Marie et al., "Rationale for the selection of ricin A-chain anti-T immunotoxins for mature T cell depletion," Transplantation, 1987, 44(6), 763-769.
Dewitt William S. et al., "Dynamics of the cytotoxic T cell response to a model of acute viral infection," Journal of Virology, Apr. 2015, 89(8), 4517-4526.
Emerson Ryan O. et al., "Immunosequencing identifies signatures of cytomegalovirus exposure history and HLA-mediated effects on the T cell repertoire," Nature Genetics, May 2017, 49(5), 659-665.
Engert Andreas et al., "A phase-I study of an anti-CD25 ricin A-chain immunotoxin (RET5-SMPT-dgA) in patients with refractory Hodgkin's lymphoma," Blood, Jan. 15, 1997, 89(2), 403-410.
Frankel, Arthur E. et al., "Therapy of patients with T-cell lymphomas and leukemias using an anti-CD7 monoclonal antibody-ricin a chain immunotoxin," Leukemia and Lymphoma, 1997, 26, 287-298.
Furlong, et al., "Therapy with mycophenolate mofetil for refractory acute and chronic graft-versus host disease," Bone Marrow Transplant., Dec. 2009, 44(11), 739-748.
Garcia-Cadenas I, et al., "Patterns of infection and infection-related mortality in patients with steroid refractory acute graft versus host disease," Bone Marrow Transplantation, 2017, 52, 107-113.
Ghetie Victor et al., "Purification and properties of immunotoxins containing one vs. two deglycosylated ricin A chains," Journal of Immunol Methods, 1993, 166, 117-122.
Harris Andrew C., et al., "International, Multicenter Standardization of Acute Graft-versus-Host Disease Clinical Data Collection," A Report from the Mount Sinai Acute GVHD International Consortium, Biol Blood Marrow Transplant, 2016, 22, 4-10.
Herrera L. et al., "Immunotoxins against CD19 and CD22 are effective in killing precursor-B acute lymphoblastic leukemia cells in vitro," Leukemia, 2000, 14, 853-858.
Hay Kevin A., et al., "Kinetics and biomarkers of severe cytokine release syndrome after CD19 chimeric antigen receptor-modified T-cell therapy," Blood, Nov. 23, 2017, 130(21), 2295-2306.
Ho Vincent T. et al., "The history and future of T-cell depletion as graft-versus-host disease prophylaxis for allogeneic hematopoietic stem cell transplantation", Blood, Dec. 1, 2001, 98(12), 3192-3204.
Holtan Shernan G., "Acute graft-versus-host disease: a bench-to-beside update," Blood, Jul. 17, 2014, 124(3), 363-373.
Kalpoe Jayant S. et al., "Validation of Clinical Application of Cytomegalovirus Plasma DNA Load Measurement and Definition of Treatment Criteria by Analysis of Correlation to Antigen Detection," J. Clin. Microbiol., Apr. 2004, 42(4), 1498-1504.
Keymeulen Bart et al., "Transient Epstein-Barr virus reactivation in CD3 monoclonal antibody-treated patients," Blood, 2010, 115(6), 1145-1155.
Lee Daniel W., et al., "Current concepts in the diagnosis and management of cytokine release syndrome," Blood, Jul. 10, 2014, 124(2), 188-195.
Lee Stephanie J., "Classification systems for chronic graft-versus-host disease," Blood, Jan. 5, 2017, 129, pp. 30-37.
Lefranc Marie-Paule, "IMGT, the International ImMunoGeneTics Information System," Cold Spring Harb. Protoc., 2011, 595-603.
Ljungman Per, et al., "Definitions of Cytomegalovirus Infection and Disease in Transplant Patients for Use in Clinical Trials," Clin. Infect. Dis, Jan. 1, 2017, 64, 87-91.
MacMillan Margaret L., et al., "Early Antithymocyte Globulin Therapy Improves Survival in Patients With Steroid-Resistant Acute Graft-Versus-Host Disease," Biology of Blood and Marrow Transplantation, 2002, 8, 40-46.
MacMillan Margaret L., et al., "A phase 2/3 multicenter randomized clinical trial of ABX-CBL versus ATG as secondary therapy for steroid-resistant acute graft-versus-host disease," Blood, Mar. 15, 2007, 109(6), 2657-2662.
MacMillan Margaret L., et al., "What predicts high risk acute graft-versus-host disease (GVHD) at onset?: identification of those at highest risk by a novel acute GVHD risk score," Br J. Haematol, 2012, 157, 732-741.
Major-Monfried Hannah et al., "MAGIC biomarkers predict long-term outcomes for steroid-resistant acute GVHD," Blood, Jun. 21, 2018, 131(25), 2846-2855.
Martin Paul J. et al., "Evaluation of a CD5-specific immunotoxin for treatment of acute graft-versus-host disease after allogeneic marrow transplantation," Blood, Aug. 1, 1996, 88(3), 824-830.
Martin Paul J. et al., "First—and second-line systemic treatment of acute graft-versus-host disease: recommendations of the American

(56) References Cited

OTHER PUBLICATIONS

Society of Blood and Marrow Transplantation," Biol. Blood Marrow Transplant., 2012, 18, 1150-1163.
Martin Paul J. et al., "Secondary treatment of acute graft-versus-host diseases: a critical review," Biol. Blood Marrow Transplant., 2012, 18, 982-988.
Martinez Carmen et al., "Alemtuzumab as treatment of steroid-refractory acute graft-versus-host disease: results of a phase II study," Biol. Blood Marrow Transplant, 2009, 15, 639-642.
Matos Tiago R. et al., "Research Techniques Made Simple: High-Throughput Sequencing of the T-Cell Receptor," J. Invest Dermatol., 2017, 137, e131-e138.
Messmann Richard A. et al., "A phase I study of combination therapy with immunotoxins lgG-HD37-deglycosylated ricin A chain (dgA) and lgG-RFB4-dgA (Combotox) in patients with refractory CD19 (+), CD22 (+) B cell lymphoma." Clin. Cancer Res., Apr. 2000, 6, 1302-1313.
Meunier Mathieu et al., "Alemtuzumab for severe steroid-refractory gastrointestinal acute graft-versus-host disease," Biol. Blood Marrow Transplant, 2014, 20, 1451-1454.
Mohty M., "Mechanisms of action of antithymocyte globulin: T-cell depletion and beyond," Leukemia, 2007, 21, 1387-1394.
Niesters Hubert G.M. et al., "Development of a Real-Time Quantitative Assay for Detection of Epstein-Barr Virus," J. Clin. Microbiol., Feb. 2000, 38, 712-715.
Olsen Elise et al., "Pivotal phase III trial of two dose levels of denileukin Diftitox for the treatment of cutaneous T-Cell lymphoma," J. Clin. Oncol., Jan. 15, 2001, 19(2), 376-388.
Preijers FW et al., "Human T lymphocyte differentiation antigens as target for immunotoxins or complement-mediated cytotoxicity," Scandinavian Journal of Immunology, 1988, 28, 185-194.
Sausville Edward A., "Continuous infusion of the anti-CD22 immunotoxin lgG-RFB4-SMPT-dgA in patients with B-cell lymphoma: a phase I study," Blood, Jun. 15, 1995, 85(12), 3457-3465.
Schindler John, et al., "The toxicity of deglycosylated ricin A chain containing immunotoxins in patients with non-Hodgkin's Lymphoma is exacerbated by prior radiotherapy: a retrospective analysis of patients in five clinical trials," Clin. Cancer Res., Feb. 2001, 7, 255-258.
Schindler John et al., "A phase I study of a combination of anti-CD19 and anti-CD22 immunotoxins (Combotox) in adult patients with refractory B-lineage acute lymphoblastic leukemia," British Journal of Haematology, 2011, 154, 471-476.
Schnell R. et al., "Clinical trials with an anti-CD25 ricin A-chain experimental and immunotoxin (RFT5-SMPT-dgA) in Hodgkin's Lymphoma," Leukemia and Lymphoma, 1998, 30, pp. 525-537.
Schnell R. et al., "Treatment of refractory Hodgkin's lymphoma patients with an anti-CD25 ricin A-chain immunotoxin," Leukemia, 2000, 14(1), 129-135.
Schnell Ronald et al., "A Phase I study with an anti-CD30 ricin A-chain immunotoxin (Ki-4.dgA) in patients with refractory CD30+ Hodgkin's and non-Hodgkin's lymphoma," Clinical Cancer Res., Jun. 2002, 8, 1779-1786.
Schnell R. et al., "Clinical evaluation of ricin A-chain immunotoxins in patients with Hodgkin's lymphoma," Annals of Oncology, 2003, 14, 729-736.
Schnitzler Marc et al., "Successful treatment of severe acute intestinal graft-versus-host resistant to systemic and topical steroids with alemtuzumab," Biology of Blood and Marrow Transplantation, 2009, 15, 910-918.

Schwartz Daniella M., et al., "JAK Inhibition as a therapeutic strategy for immune and inflammatory diseases," Nature Reviews, Drug Discovery, Dec. 2017, 16, 843-862.
Shaughnessy Paul J. et al., "Denileukin diftitox for the treatment of steroid-resistant acute graft-versus-host disease," Biol. Blood Marrow Transplant, 2005, 11, 188-193.
SociéGéard et al., "A phase 3 randomized trial comparing inolimomab vs usual care in steroid-resistant acute GVHD," Blood, Feb. 2, 2017, 129(5), 643-649.
Socie Géard, et al., "Acute graft-versus-host disease: from the bench to the bedside," Blood, Nov. 12, 2009, 114(20), 4327-4336.
Spits Hergen et al., "Characterization of Monoclonal Antibodies Against Cell Surface Molecules Associated with Cytotoxic Activity of Natural and Activated Killer Cells and Cloned CTL Lines," Hybridoma, 1983, 2(4), 423-437.
Stone Marvin J. et al., "A phase I study of bolus versus continuous infusion of the anti-CD19 immunotoxin, lgG-HD37-dgA, in patients with B-cell lymphoma," Blood, Aug. 15, 1996, 88(4), 1188-1197.
Styczynski Jan, "Management of Epstein-Barr Virus Infections and post-transplant lymphoproliferative disorders in patients after allogeneic hematopoietic stem cell transplantation: Sixth European Conference on Infections in Leukemia (ECIL-6) guidelines," Haematologica, 2016, 101(7), 803-811.
Taur Ying et al., "Intestinal domination and the risk of bacteremia in patients undergoing allogeneic hematopoietic stem cell transplantation," Clin. Infect. Dis., Oct. 1, 2012, 55, 905-914.
Tax W.J.M. et al., "Monoclonal antibodies against human thymocytes and T lymphocytes," Protides of the biological fluids, $29^{th}$ Colloquium, 1981, edits by Peters H, Pergamon Press, Oxford and New York, 701-704.
Tax W.J.M. et al., "WT1: A Monoclonal Antibody Reactive with T-ALL but not with Other Leukemias," Haematology and Blood Transfusion, 1983, 28, 139-141.
Tax et al., "Monoclonal antibody (WT 1) directed against a T cell surface glycoprotein: characteristics and immunosuppressive activity," Clin. Exp. Immunol., 1984, 55, 427-436.
Tommasi M. et al., "Identification of ricin A-chain HLA class II-restricted epitopes by human T-cell clones," Clin. Exp. Immunol., 2001, 125, 391-400.
Van Groningen LF et al., "Combination Therapy with Inolimomab and Etanercept for Severe Steroid-Refractory Acute Graft-versus-Host Disease," Biol Blood Marrow Transplant, 2016, 22, 179-182.
Van Oosterhout et al., "Suitability of a Cocktail of CD3 and CD7 Ricin A-Immunotoxins for in vivo Treatment of Acute Graft-Versus-Host-Disease", Blood, 1997, 90(10), 1997, 376B.
Van Oosterhout et al., "A combination of anti-CD3 and anti-CD ricin A-immunotoxins for the in vivo treatment of acute graft versus host disease", Blood, Jun. 15, 2000, 95(12), 3693-3701.
Van Oosterhout et al., "Production of anti-CD3 and anti-CD7 ricin A-immunotoxins for a clinical pilot study," Int. J. Pharm, 2001, 221, 175-186.
Vitetta Ellen S. et al., "Phase I immunotoxin trial in patients with B-cell lymphoma," Cancer Research, Aug. 1, 1991, 51, 4052-4058.
Willemsen Laura, et al., "Impact of serotherapy on immune reconstitution and survival outcomes after stem cell transplantations in children: thymoglobulin versus alemtuzumab," Biology of Blood and Marrow Transplantation, 2015, 21, 473-482.
Yu Y.H. et al., "Use of immunotoxins in combination to inhibit clonogenic growth of human breast carcinoma cells," Cancer Research, Jun. 1, 1990, 50, 3231-3238.
Zeiser Robert et al., "Acute graft-versus-host disease biological process, prevention and therapy," N. Engl. J. Med., Nov. 30, 2017, 377(22), 2167-2179.

* cited by examiner

IMMUNOTOXINS, FORMULATIONS THEREOF AND THEIR USE IN MEDICINE

CROSS-REFERENCE TO RELATED APPLICATIONS

This application is a U.S. National Phase application, filed under U.S.C. § 371(c), of International Application No. PCT/EP2018/079860, filed Oct. 31, 2018, which claims the priority benefit of GB 1717966.4, filed Oct. 31, 2017, the entire contents of each of which are incorporated herein by reference in their entireties.

INCORPORATION-BY-REFERENCE OF SEQUENCE LISTING

The contents of the file named "XENI-002_N01US_SeqListing_ST25", which was created on Apr. 27, 2020, and is 19 KB in size are hereby incorporated by reference in their entirety.

FIELD OF THE INVENTION

The present invention relates to the field of therapy, including preventative therapy for chronic Graft versus Host Disease (cGVHD), antiviral therapy, including prevention of viral reactivation and control of viral reactivation, and prevention of progression of Epstein-Barr virus (EBV) infection to post-transplant lymphoproliferative disorder (PTLD), and development of Progressive multifocal leukoencephalopathy (PML), in the context of immunomodulatory therapy (e.g. immunosuppression). Provided are methods and means for use in such therapy, including improved pharmaceutical compositions.

BACKGROUND TO THE INVENTION

Immunosuppression is employed in the treatment of certain life-threatening immune conditions, such as transplant-related rejection, Graft versus Host Disease (GVHD), acute solid-organ rejection and several severe autoimmune diseases.

EP 0945139 A1, EP 1 066 058 B1 and US 2006/051355 describe an immunotoxin cocktail for treatment of immune related diseases such as GVHD after allogeneic hematopoietic stem cell transplantation (HSCT). The immunotoxin cocktail comprises an anti-CD3 antibody and anti-CD7 antibody, each conjugated to ricin A, which targets mature T cells and natural killer (NK) cells, "resetting" the immune system. These documents report a pilot clinical study in which the immunotoxin cocktail was administered to human patients having acute GVHD (aGVHD).

WO 98/55150 describes immunotoxins comprising the monoclonal antibody TXU-7 linked to an amount of pokeweed antiviral protein for the treatment of T cell leukemias, lymphomas, acute myeloid leukemias and viral infections, including HIV infection.

US 2008/233128 describes treatment of viral infections with T-cell depleting antibodies, such as anti-CD3 "OKT3". The studies described therein are study designs without reporting actual outcomes.

van Oosterhout et al., Blood, 2000, Vol. 95, No. 12, pp. 3693-3701, describes a pilot study for treatment of acute GVHD using an anti-CD3 and anti-CD7 immunotoxin combination.

Keymeulen et al., Blood, 2010, Vol. 115, No. 6, pp. 1145-1155 reports that treatment of Type 1 Diabetes patients with an anti-CD3 antibody (TRX4) was associated with a transient reactivation of EBV.

van Oosterhout et al., Int. J. Pharm, 2001, Vol. 221, pp. 175-186 describes the production of an immunotoxin cocktail of anti-CD3 and anti-CD7 ricin A-immunotoxins for a pilot clinical study into the treatment of GVHD.

Antibody therapy with Campath (Alemtuzumab) has been employed for immunotherapy of, e.g., B-cell chronic lymphocytic leukemia (B-CLL). Campath has been used in the treatment of acute intestinal GVHD resistant to systemic and topical steroids (Schnitzler et al., *Biology of Blood and Marrow Transplantation*, 2008, Vol. 15, No. 8, pp. 910-919). However, a complication of Campath therapy is a significant increase in the risk for opportunistic infections, in particular, reactivation of human cytomegalovirus (CMV) (Schnitzler et al. *ibid*).

Antibody therapy with anti-thymocyte globulin (ATG) has been employed for immunotherapy of acute rejection in organ transplantation and therapy of aplastic anaemia. ATG has also been employed in treatment of GVHD (Bacigalupo et al., *Blood*, 2001, Vol. 98, No. 10, pp. 2942-2947). However, a higher risk of lethal infection was reported (Bacigalupo et al. *ibid*). Early treatment with ATG has been reported to improve survival in patients with steroid-resistant aGVHD (MacMillan et al., *Biology of Blood and Narrow Transplantation*, 2002, Vol. 8, pp. 40-46). A phase 2/3 multicenter randomized clinical trial of ABX-CBL, a hybridoma generated murine IgM monoclonal antibody against the CD147 antigen, compared against ATG for steroid-resistant aGVHD found that ABX-CBL did not show an improvement over ATG in the treatment of acute steroid-resistant GVHD (MacMillan et al., *Blood*, 2007, Vol. 109, No 6, pp. 2657-2662).

Although a number of therapies have shown promise in the treatment of aGVHD, studies to date have reported a stubbornly high incidence of chronic GVHD (cGVHD) that develops in surviving patients at a later time point. For example, reported rates of development of cGVHD among aGVHD-treated survivors are in the range 44%-80% (see: Furlong et al., *Bone Marrow Transplant.*, 2009, Vol. 44, No. 11, pp. 739-748; Socié et al., *Blood*, 2017, Vol. 129, No. 5, pp. 643-649; MacMillan et al., *Biology of Blood and Marrow Transplantation*, 2002, Vol. 8, pp. 40-46; and MacMillan et al., *Blood*, 2007, Vol. 109, No. 6, pp. 2657-2662).

Post-transplant lymphoproliferative disorder (PTLD) is the name given to a B-cell proliferation due to therapeutic immunosuppression after organ transplantation. The disease is an uncontrolled proliferation of B cell lymphocytes latently infected with Epstein-Barr virus (EBV).

Prior known immunotoxin therapies have reported complications including capillary leak syndrome (CLS). This can limit the patients for whom immunotoxin therapy may be used (for example, to those having at least a certain serum albumin level prior to treatment. It would be desirable to provide an immunotoxin-based therapy that minimises complications including and/or related to capillary leak syndrome.

Known pharmaceutical compositions for storage and delivery of combination immunotoxins have been found to exhibit a number of shortcomings in relation to longer term stability, particularly at higher temperatures. In particular, appearance of insoluble aggregates may impact the shelf-life of such pharmaceutical compositions and/or require prolonged cold storage.

Accordingly, while anti-T-cell immunosuppression shows great promise in the treatment of certain serious immune disorders, there remains an unmet need for treatment options, including preventative treatment, for viral infection and/or viral reactivation among such immunocompromised patients, and an unmet need for treatment options that reduce the incidence of cGVHD subsequent to the treatment of aGVHD and/or which minimise or avoid complications hitherto associated with immunotoxin therapy, such as severe capillary leak syndrome. Further unmet needs include the provision of increased stability formulations of medicaments for the treatment of the above-mentioned conditions. The present invention addresses these and other needs.

BRIEF DESCRIPTION OF THE INVENTION

Broadly, the present invention relates to methods and means for treating (including prophylactic treatment) viral infection or viral reactivation in subjects who are undergoing immunomodulatory treatment, particularly T-cell directed immunosuppression and/or the suppression of inflammatory cytokines. The present inventors have surprisingly found that subjects, such as human post-transplant patients, treated with the T-Guard® combination therapy (a cocktail of anti-CD3 and anti-CD7 immunotoxins), exhibit reduced incidence of viral infection and/or viral reactivation, e.g. with human cytomegalovirus (CMV) and/or Epstein-Barr virus (EBV), when compared with patients treated with a standard immunosuppressive control. As described herein, this is reflected in increased survival among T-Guard®-treated patients especially in the early post-treatment phase when opportunistic viral infection is particularly problematic. In patients whose viral titre was monitored, resolution of viral reactivation (i.e. viral titre returning to lower levels after a spike) was seen during or following (e.g. shortly following) T-Guard® treatment.

Accordingly, in a first aspect the present invention provides a composition comprising a first antibody molecule that specifically recognises CD3 and a second antibody molecule that specifically recognises CD7, for use in a method of treatment, or preventative treatment, of viral infection or viral reactivation or of progression of a viral infection or viral reactivation to PTLD or PML, in a mammalian subject undergoing immunomodulatory treatment, wherein the first and second antibody molecules are each provided with a toxic moiety.

The first aspect of the present invention also provides a first antibody molecule that specifically recognises CD3 and which first antibody molecule is linked to a toxic moiety for use in a method of treatment, or preventative treatment, of viral infection or viral reactivation or of progression of a viral infection or viral reactivation to PTLD or PML in a mammalian subject undergoing immunomodulatory treatment, wherein said first antibody molecule is for simultaneous, separate or sequential administration with a second antibody molecule that specifically recognises CD7, said second antibody molecule being linked to a toxic moiety.

The first aspect of the present invention also provides an antibody molecule that specifically recognises CD7 ("second antibody molecule") and which antibody molecule is linked to a toxic moiety for use in a method of treatment, or preventative treatment, of viral infection or viral reactivation or of progression of a viral infection or viral reactivation to PTLD or PML in a mammalian subject undergoing immunomodulatory treatment, wherein said second antibody molecule is for simultaneous, separate or sequential administration with a further antibody molecule that specifically recognises CD3 ("first antibody molecule"), said first antibody molecule being linked to a toxic moiety.

In accordance with this aspect of the present invention the composition may be provided in the form of a mixture or cocktail of the anti-CD3 and the anti-CD7 antibody molecules or may be provided in the form of a kit of parts comprising a first composition comprising the anti-CD3 antibody molecule and a second composition comprising the anti-CD7 antibody molecule, e.g. packaged or contained in separate containers. The kit of parts may be for combination prior to administration to the subject or may be for simultaneous, separate or sequential administration, wherein the first and second compositions are each administered to the same subject.

In some cases said first and second antibody molecules are provided in the form of a composition (e.g. a mixture or cocktail) and are to be administered to the subject by administering one or more doses of said composition. The composition may, for example, be a mixture of the first and second antibody molecules each with their respective toxic moieties, wherein the first and second antibody molecules are in a molar ratio in the range 100:1 to 1:100, typically 10:1 to 1:10 and in certain cases 2:1 to 1:2, such as approximately 1:1.

In some cases the virus of the viral infection or reactivation may be other than HIV. In certain cases, the viral infection or viral reactivation may be a virus of the order Herpesvirales. In particular, the viral infection may be selected from human cytomegalovirus (CMV) and Epstein-Barr virus (EBV). In certain cases the viral infection or viral reactivation may be with a JC virus (also known as John Cunningham virus) of the family Polyomaviridae.

In some cases the immunomodulatory treatment is immunosuppressive treatment. In particular, the immunomodulatory treatment may be T-cell directed immunosuppression. In certain cases, the immunomodulatory treatment comprises treatment of Graft versus Host disease (GvHD), graft rejection, autoimmune disease, T-cell leukaemia or T-cell lymphoma. In particular, the autoimmune disease may be a disease having aberrant T-cell activity as a component.

In some cases, the composition is the same composition used for the immunomodulatory treatment. That is to say one or more doses of the composition (e.g. T-Guard®) or its component antibody molecules for simultaneous, separate or sequential administration may be administered, or for administration, to a subject to achieve a double effect or dual purpose. Namely, the treatment of a T-cell mediated condition requiring immunosuppression and the treatment or preventative treatment of viral infection or viral reactivation or progression to PTLD or PML.

In some cases, the first antibody molecule and/or the second antibody molecule is a murine antibody.

In some cases, the first antibody molecule is an IgG2b isotype monoclonal antibody that selectively binds human CD3. In particular, the first antibody molecule may be the antibody disclosed as "SPV-T3a" in EP 0945139 A1 and Spits et al., *Hybridoma,* 1983, Vol. 2, p. 423 (the entire contents of which are expressly incorporated herein by reference).

In some cases, the second antibody molecule is an IgG2a isotype monoclonal antibody. In particular, the second antibody molecule may be the antibody disclosed as "WT1" in in EP 0945139 A1 and Tax et al., Monoclonal antibodies against human thymocytes and T lymphocytes. Protides of the biological fluids, 29th Colloquium, 1981, edited by Peeters H, Pergamon Press, Oxford and New York, 1982, and Tax et al., *Clin. Exp. Immunol.,* 1984, Vol. 55, p. 427 (the entire contents of which are expressly incorporated herein by reference).

In some cases, the first antibody and the second antibody are conjugated to a toxic moiety selected from the group consisting of: ricin, deglycosylated ricin A (dgRTA), and non-glycosylated recombinant ricin A. The antibodies may be conjugated to the toxic moiety, e.g. ricin A, using any suitable conjugation or linker chemistry. In particular, the conjugation may employ N-succinimydyl 3-(2-pyridyldithio)propionate (SPDP; Pharmacia) or 4-succinimidyloxycarbonyl-alpha-methyl-α(2-pyridyldithio)toluene (SMPT). The conjugation ratio of toxin (e.g. ricin A) to antibody molecule may be in the range 0.5:1 to 5:1. In particular, the conjugation ratio of toxin (e.g. ricin A) to antibody molecule may be in the range 0.8:1 to 1.2:1.

Preparation of the antibodies and conjugation to toxins, such as ricin A, may be as described in EP 0945139 A1 (see page 8, paragraphs [0063] to [0065] thereof), the entire contents of which are expressly incorporated herein by reference. Specifically contemplated herein are fully recombinant immunotoxins (e.g., Fab, scFv or SC mAb linked through cleavable peptide linker to a recombinant ribosomal inhibiting protein. Additionally or alternatively, the first and second antibody molecules may be provided as a single bispecific (anti-CD3/anti-CD7) antibody, thereby providing a bispecific immunotoxin such as anti-CD3/CD7-rRTA.

In some cases, at least one of the following is de-immunised:
the first antibody;
the second antibody;
the toxic moiety of the first antibody; and
the toxic moiety of the second antibody. De-immunization strategy may be performed by Epibase® or Epibase IV® (Lonza Group AG) or EpiMatrix T cell epitope mapping system (EpiVax, Inc.).

In some cases, the subject has been determined to have, or to be at risk of, viral infection with EBV and/or CMV. For instance, in the case of donor-recipient transplant combinations in which the donor has, or is suspected of having, a history of EBV and/or CMV infection in combination with a EBV/CMV negative recipient. A further example is a recipient of a transplant that has been 'conditioned' with an anti-T cell therapy. In particular, the subject may exhibit an EBV and/or CMV viral titre above 1000 viral DNA copies/ml of blood. In particular, the subject may exhibit an elevated and/or rising EBV and/or CMV viral titre at any point during the period beginning 7 days prior to the first dose of immunomodulatory therapy and ending with the final dose of immunomodulatory therapy. For example, the subject may present with an elevated EBV and/or CMV plasma viral titre on the day of, or one or more days before, the first dose of the immunomodulatory treatment. Alternatively or additionally, the subject may exhibit a rising plasma viral titre of EBV and/or CMV (i.e. a higher titre on a second or subsequent measurement as compared with a first measurement) indicating that the viral infection or reactivation is poorly controlled. Subjects, including immunocompromised human patients, exhibiting elevated and/or rising EBV and/or CMV viral titre may be particularly suited to treatment with a composition of the invention, such as T-Guard®.

In some embodiments the composition provides a clinical benefit as assessed by a reduction in viral titre (e.g. an EBV and/or CMV viral titre of less than 1000 viral DNA copies/ml of blood) at 180 days after administering the composition of the first aspect of the invention.

In some cases, the composition suppresses and/or kills CD3+ and/or CD7+ T-cells.

In some cases, the composition spares CD8+ anti-viral T-cells relative to CD3+ and/or CD7+ T-cells. In particular, the composition may target CD3+ and CD7+ T-cells, while relatively sparing anti-viral T-cells, such as CTLs that target CMV and/or EBV.

In some cases the composition may be for use in a method of treatment, including preventative treatment, of PTLD. In some cases the composition may be for use in a method of treatment, including preventative treatment, of Progressive multifocal leukoencephalopathy (PML).

PML is a rare and usually fatal viral disease characterized by progressive damage or inflammation of the white matter of the brain at multiple locations. It is caused by the JC virus, which is normally present and kept under control by the immune system. JC virus is generally harmless except in cases of weakened immune systems. In general, PML has a mortality rate of 30-50 percent in the first few months and those who survive can be left with varying degrees of neurological disabilities. PML occurs almost exclusively in patients with severe immune deficiency, most commonly among patients with acquired immune deficiency syndrome (AIDS), but people on chronic immunosuppressive medications including chemotherapy are also at increased risk of PML, such as patients with transplants, Hodgkin's Lymphoma, multiple sclerosis, psoriasis and other autoimmune diseases.

In some cases the subject is monitored for viral infection and/or reactivation, e.g. with CMV or EBV, as part of the method of treatment. That is to say, the subject, or more regularly a sample such as a blood or plasma sample obtained from the subject, may be analysed in order to measure viral titre or signs of viral infection, viral multiplication or viral reactivation. Alternatively of additionally, the subject may be monitored for indirect signs of viral infection or reactivation, such as symptoms of viral infection. Such monitoring may be performed before, during and/or after treatment. In particular cases, monitoring may be performed on a periodic basis during the course of treatments, e.g. daily or weekly determinations of viral titre. In some cases, monitoring the subject for viral infection and/or reactivation comprises measuring viral titre at least once before, during and/or after the immunomodulatory treatment. In certain cases, monitoring comprises measuring plasma viral titre by real-time quantitative PCR.

In some cases, the subject is being or has been treated with prophylactic antiviral medication. For example, the subject may have undergone a course of treatment with Aciclovir®.

In a second aspect, the present invention provides a method of treating a mammalian subject having, or being at risk of, a viral infection or viral reactivation, the method comprising:
administering simultaneously, separately or sequentially a therapeutically effective amount of a first antibody molecule that specifically recognises CD3 and a second antibody molecule that specifically recognises CD7, wherein the first and second antibody molecules are each provided with a toxic moiety, to the subject in need of said treatment,
and wherein the subject is undergoing immunomodulatory treatment. In some cases said first and second antibody molecules are provided in the form of a composition (e.g. a mixture or cocktail) and are administered to the subject by administering one or more doses of said composition. The composition may, for example, be a mixture of the first and second antibody molecules each with their respective toxic moieties, wherein the first and second antibody molecules are in a molar ratio in the range 100:1 to 1:100, typically 10:1 to 1:10 and in certain cases 2:1 to 1:2, such as approximately 1:1.

In some embodiments the method of treatment provides a clinical benefit as assessed by a reduction in viral titre (e.g. an EBV and/or CMV viral titre of less than 1000 viral DNA copies/ml of blood) at 180 days after administering said first and second antibodies.

The compositions, options and other features of the first aspect of the invention apply equally to the second aspect of the invention.

In a third aspect, the present invention provides use of a composition comprising a first antibody molecule that specifically recognises CD3 and a second antibody molecule that specifically recognises CD7, in the preparation of a medicament for use in a method of treatment, or preventative treatment, of viral infection or viral reactivation in a mammalian subject undergoing immunomodulatory treatment, wherein the first and second antibody molecules are each provided with a toxic moiety. The first and second antibodies may be provided as a composition (e.g. a mixture or cocktail) to be administered to the subject by administering one or more doses of said composition. Alternatively, the first and second antibodies may be provided in the form of a kit of parts comprising a first composition comprising the anti-CD3 antibody molecule and a second composition comprising the anti-CD7 antibody molecule, e.g. packaged or contained in separate containers. The kit of parts may be for combination prior to administration to the subject or may be for simultaneous, separate or sequential administration, wherein the first and second compositions are each administered to the same subject.

The compositions, options and other features of the first aspect of the invention apply equally to the third aspect of the invention.

In a fourth aspect, the present invention provides a composition comprising a first antibody molecule that specifically recognises CD3 and a second antibody molecule that specifically recognises CD7, for use in a method of treatment, or preventative treatment, of chronic Graft versus Host disease (cGVHD) in a mammalian subject undergoing immunomodulatory treatment, wherein the first and second antibody molecules are each provided with a toxic moiety.

In some embodiments, the composition may be for use in preventative treatment of cGVHD to provide clinical benefit as measured by the incidence of cGVHD at 180 days following said immunomodulatory treatment.

In some embodiments, the immunomodulatory treatment comprises treatment of acute Graft versus Host disease (aGVHD). For example, a patient who has received an allogeneic stem cell transplant and has developed aGVHD, especially steroid-refractory aGVHD, may be treated with the composition, e.g. T-Guard®, so as to provide therapeutic benefit for the aGVHD and in order to provide clinical benefit in the form of a reduced likelihood of developing cGVHD (e.g. as measured at 180 days following the treatment with the composition, e.g. T-Guard®).

In some embodiments, the composition is the same composition used for the immunomodulatory treatment, the composition therefor being administered for a dual purpose. Namely, the treatment of aGVHD and the preventative treatment of cGVHD.

In connection with the fourth aspect of the present invention the first and second antibody molecules may be as defined in accordance with the first aspect of the invention.

In a fifth aspect, the present invention provides a method of treating a mammalian subject having, or being at risk of developing, chronic Graft versus Host disease (cGVHD), the method comprising:

administering simultaneously, separately or sequentially a therapeutically effective amount of a first antibody molecule that specifically recognises CD3 and a second antibody molecule that specifically recognises CD7, wherein the first and second antibody molecules are each provided with a toxic moiety, to the subject in need of said treatment, and wherein the subject is undergoing immunomodulatory treatment. In some cases said first and second antibody molecules are provided in the form of a composition (e.g. a mixture or cocktail) and are administered to the subject by administering one or more doses of said composition. The composition may, for example, be a mixture of the first and second antibody molecules each with their respective toxic moieties, wherein the first and second antibody molecules are in a molar ratio in the range 100:1 to 1:100, typically 10:1 to 1:10 and in certain cases 2:1 to 1:2, such as approximately 1:1.

The compositions, options and other features of the first aspect of the invention apply equally to the fifth aspect of the invention.

In some embodiments, the immunomodulatory treatment comprises treatment of acute Graft versus Host disease (aGVHD). For example, a patient who has received an allogeneic stem cell transplant and has developed aGVHD, especially steroid-refractory aGVHD, may be treated with the composition, e.g. T-Guard®, so as to provide therapeutic benefit for the aGVHD and in order to provide clinical benefit in the form of a reduced likelihood of developing cGVHD (e.g. as measured at 180 days following the treatment with the composition, e.g. T-Guard®).

In some embodiments, the composition is the same composition used for the immunomodulatory treatment, the composition therefor being administered for a dual purpose. Namely, the treatment of aGVHD and the preventative treatment of cGVHD.

In a sixth aspect, the present invention provides a pharmaceutical composition comprising:
(i) 0.05 to 0.5 mg/mL, optionally 0.2 mg/mL, of a monoclonal antibody molecule that specifically recognises CD3 and which is conjugated to at least one ricin toxin A (RTA), and/or
0.05 to 0.5 mg/mL, optionally 0.2 mg/mL, of a monoclonal antibody molecule that specifically recognises CD7 and which is conjugated to at least one RTA;
(ii) 5 to 20 mM, optionally 10 mM, of a citrate buffer;
(iii) 50 to 300 mM, optionally 75 to 200 mM or 125 mM, of L-arginine or a pharmaceutically acceptable salt thereof;
(vi) 0.01 to 0.1% (w/v), optionally 0.05° (w/v), of a polysorbate,
wherein the composition is in water and has a pH in the range 6 to 7.5, optionally 6.5.

In some embodiments, the antibody molecule that specifically recognises CD3 is a murine IgG2b isotype monoclonal antibody that selectively binds human CD3. In particular, the antibody may be SPV-T3a.

In some embodiments, the antibody molecule that specifically recognises CD7 is a murine IgG2a isotype monoclonal antibody that selectively binds human CD7. In particular, the antibody may be WT1.

In certain embodiment, both SPV-T3a and WT1 are present in the composition. In some cases, each antibody is conjugated to an average of between 1 and 2 RTA (e.g. deglycosylated RTA (dgRTA)) molecules per antibody molecule. In some cases, the conjugation is via an 4-succinimidyloxycarbonyl-alpha-methyl-α(2-pyridyldithio)toluene crosslinker.

In some embodiments, the citrate buffer comprises a pharmaceutically acceptable base forming a salt with citric acid, for example, sodium, calcium, potassium, magnesium, or ammonium citrate. In certain embodiments, the citrate buffer comprises sodium citrate.

In some embodiments, the L-arginine salt is L-arginine.HCl.

In some embodiments, the polysorbate is Tween® 20.

In some embodiments, the composition further comprises at least one agent selected from:
120 to 160 mM maltose;
100 to 150 mM, optionally 125 mM, trehalose;
25 to 75 mM, optionally 50 mM, glycine; and
80 to 120 mM, optionally 100 mM, mannitol.

In particular, the composition may comprise 130 to 150 mM, optionally 140 mM, maltose monohydrate.

In some embodiments, the composition comprises:
(i) 0.2 mg/mL of SPV-T3a-dgRTA and 0.2 mg/ml WT1-dgRTA;
(ii) 10 mM sodium citrate/citric acid buffer;
(iii) 125 mM of L-arginine.HCl;
(iv) 0.05% (w/v) Tween® 20;
(v) 140 mM maltose monohydrate
wherein the composition is in water for injection and has a pH of 6.5.

In some embodiments, the composition is sterile. In some embodiments, the composition is suitable for injection.

In a seventh aspect, the present invention provides a lyophilised composition that is a freeze-dried form of the composition of the sixth aspect of the invention. The lyophilised composition may be suitable for reconstitution, e.g., with water or an aqueous solution to form the composition of the sixth aspect of the invention.

In an eight aspect, the present invention provides the pharmaceutical composition of the sixth or seventh aspect of the invention for use in the method of treatment of the second aspect of the invention and/or for use in the method of treatment of the fifth aspect of the invention.

In a ninth aspect, the present invention provides use of a composition of the sixth or seventh aspect of the invention in the preparation of a medicament for use in the method of treatment of the second aspect of the invention and/or for use in the method of treatment of the fifth aspect of the invention.

In a tenth aspect, the present invention provides an article of manufacture comprising:
a container or housing;
the container or housing having therein a composition of the sixth or seventh aspect of the invention; and
a label or insert with instructions for use of the composition in the method of treatment of the second aspect of the invention and/or for use in the method of treatment of the fifth aspect of the invention. In some cases, the container or housing retains sterility, e.g., by means of a seal and/or air-tight closure. In an eleventh aspect, the present invention provides a composition of the sixth or seventh aspect of the invention for use in medicine.

In a twelfth aspect, the present invention provides a composition of the sixth or seventh aspect of the invention for use in a method of treatment of acute Graft versus Host disease (aGVHD), graft rejection, autoimmune disease, T-cell leukaemia or T-cell lymphoma in a mammalian subject.

In a thirteenth aspect, the present invention provides a method of treating acute Graft versus Host disease (aGVHD), graft rejection, autoimmune disease, T-cell leukaemia or T-cell lymphoma in a mammalian subject, the method comprising administering a composition of the sixth or seventh aspect of the invention to a subject in need thereof.

In a fourteenth aspect, the present invention provides use of a composition of the sixth or seventh aspect of the invention in the preparation of a medicament for treating acute Graft versus Host disease (aGVHD), graft rejection, autoimmune disease, T-cell leukaemia or T-cell lymphoma in a mammalian subject.

In a fifteenth aspect, the present invention provides an article of manufacture comprising:
a container or housing;
the container or housing having therein a composition of the sixth or seventh aspect of the invention; and
a label or insert with instructions for use of the composition in the method of treatment of acute Graft versus Host disease (aGVHD), graft rejection, autoimmune disease, T-cell leukaemia or T-cell lymphoma in a mammalian subject. In some cases, the container or housing retains sterility, e.g., by means of a seal and/or air-tight closure.

In a sixteenth aspect, the present invention provides a composition comprising a first antibody molecule that specifically recognises CD3 and a second antibody molecule that specifically recognises CD7, wherein the first and second antibody molecules are each provided with a toxic moiety, for use in a method of treatment of acute Graft versus Host disease (aGVHD), graft rejection, autoimmune disease, T-cell leukaemia or T-cell lymphoma in a human patient, wherein the patient has a serum albumin level of less than 30 g/L as measured prior to administration of said composition.

In some embodiments, the composition the patient has a serum albumin level of between 10 g/L and 30 g/L, optionally between 15 g/L and 25 g/L. In some embodiments, the composition is for use in a method to provide clinical benefit as measured by the incidence of grade 3 or above capillary leak syndrome (CLS) following administration of said composition. In some embodiments, the first and second antibody molecules are as defined in connection with the first aspect of the invention. In some embodiments, the composition is as defined in connection with the sixth aspect of the invention.

In a seventeenth aspect, the present invention provides a method for treating acute Graft versus Host disease (aGVHD), graft rejection, autoimmune disease, T-cell leukaemia or T-cell lymphoma in a human patient, the method comprising administering, simultaneously, separately or sequentially, a therapeutically effective amount of a first antibody molecule that specifically recognises CD3 and a second antibody molecule that specifically recognises CD7, wherein the first and second antibody molecules are each provided with a toxic moiety, to the patient in need of said treatment, and wherein the patient has a serum albumin level of less than 30 g/L as measured prior to administration of said composition. In some embodiments, the patient has a serum albumin level of between 10 g/L and 30 g/L, optionally between 15 g/L and 25 g/L. In some embodiments, the method is to provide clinical benefit as measured by the incidence of grade 3 or above capillary leak syndrome (CLS) following said administration. In some embodiments, the first and second antibody molecules are as defined in connection with the first aspect of the invention. In some embodiments, the composition is as defined in connection with the sixth aspect of the invention.

In an eighteenth aspect, the present invention provides use of a composition comprising a first antibody molecule that specifically recognises CD3 and a second antibody molecule that specifically recognises CD7, wherein the first and second antibody molecules are each provided with a toxic moiety, in the preparation of a medicament for treating acute Graft versus Host disease (aGVHD), graft rejection, autoimmune disease, T-cell leukaemia or T-cell lymphoma in a human patient, wherein the patient has a serum albumin level of less than 30 g/L as measured prior to administration of said composition. In some embodiments, the patient has a serum albumin level of between 10 g/L and 30 g/L, optionally between 15 g/L and 25 q/L. In some embodiments, the medicament is for providing a clinical benefit as measured by the incidence of grade 3 or above capillary leak syndrome (CLS) following said administration. In some embodiments, the first and second antibody molecules are as defined in connection with the first aspect of the invention. In some embodiments, the composition is as defined in connection with the sixth aspect of the invention.

The present invention includes the combination of the aspects and preferred features described except where such a combination is clearly impermissible or is stated to be expressly avoided. These and further aspects and embodiments of the invention are described in further detail below and with reference to the accompanying examples and figures.

DETAILED DESCRIPTION OF THE INVENTION

Figure 1:
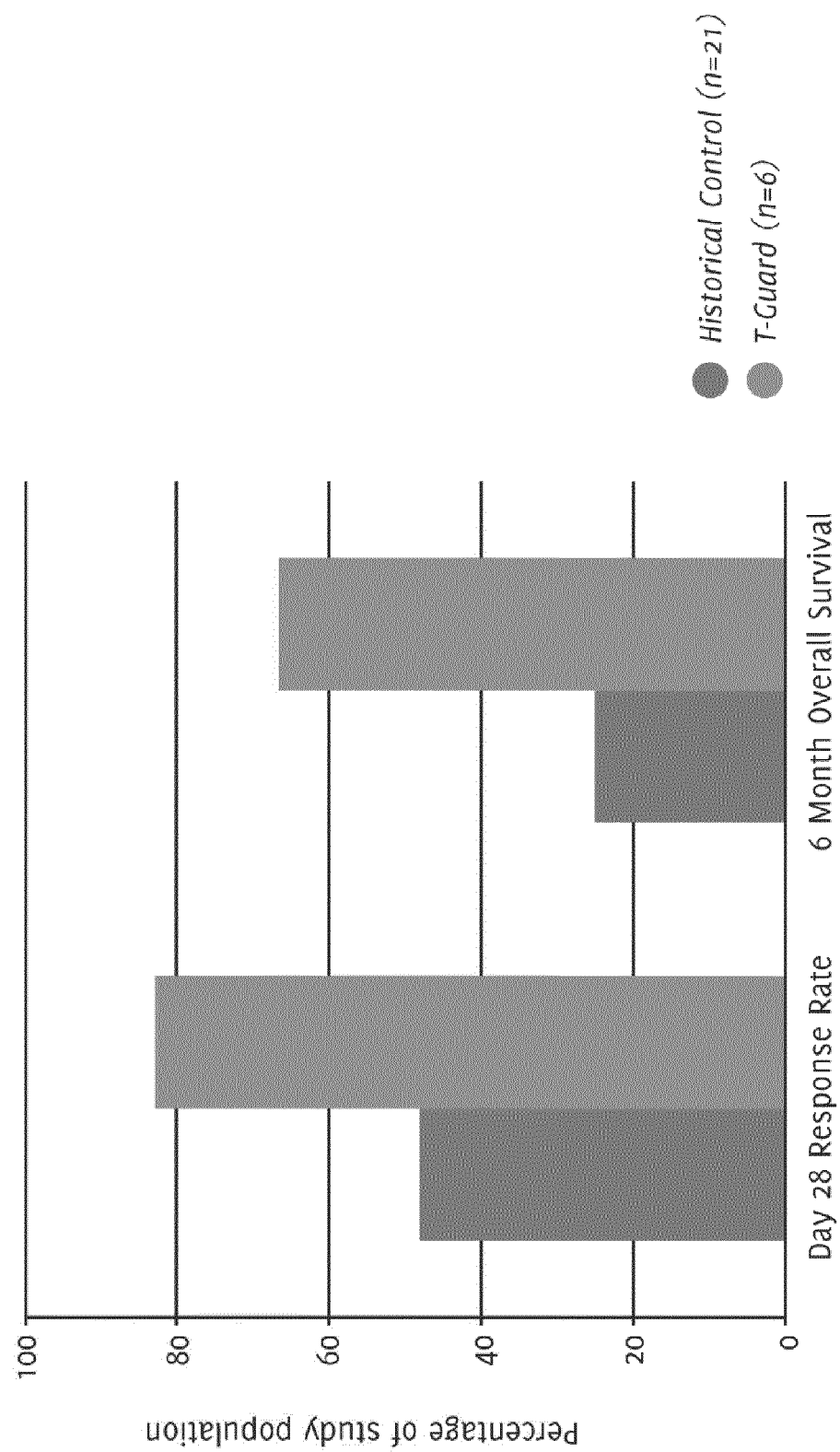
FIG. 1 shows day 28 response rate (bars 1 and 2) and 6-month overall survival (bars 3 and 4) for control (n=21) (bars 1 and 3) and for T-Guard®-treated (n=6) (bars 2 and 4) expressed as percentage of the study population. Both response rate and survival were higher in the T-Guard®-treated group.

In describing the present invention, the following terms will be employed, and are intended to be defined as indicated below.

Antibody Molecule

As used herein with reference to all aspects of the invention, the term "antibody" or "antibody molecule" includes any immunoglobulin whether natural or partly or wholly synthetically produced. The term "antibody" or "antibody molecule" includes monoclonal antibodies (mAb) and polyclonal antibodies (including polyclonal antisera). Antibodies may be intact or fragments derived from full antibodies (see below). Antibodies may be human antibodies, humanised antibodies or antibodies of non-human origin. "Monoclonal antibodies" are homogeneous, highly specific antibody populations directed against a single antigenic site or "determinant" of the target molecule. "Polyclonal antibodies" include heterogeneous antibody populations that are directed against different antigenic determinants of the target molecule. The term "antiserum" or "antisera" refers to blood serum containing antibodies obtained from immunized animals.

It has been shown that fragments of a whole antibody can perform the function of binding antigens. Thus reference to antibody herein, and with reference to the methods, arrays and kits of the invention, covers a full antibody and also covers any polypeptide or protein comprising an antibody binding fragment. Examples of binding fragments are (i) the Fab fragment consisting of $V_L$, $V_H$, $C_T$, and $C_H1$ domains; the Fd fragment consisting of the $V_H$ and $C_H1$ domains; (iii) the Fv fragment consisting of the $V_L$ and $V_H$ domains of a single antibody; (iv) the dAb fragment which consists of a V', domain; (v) isolated CDR regions; (vi) F(ab')$_2$ fragments, a bivalent fragment comprising two linked Fab fragments (vii) single chain Fv molecules (scFv), wherein a $V_H$ domain and a $V_L$ domain are linked by a peptide linker which allows the two domains to associate to form an antigen binding site; (viii) bispecific single chain Fv dimers (WO 93/11161) and (ix) "diabodies", multivalent or multispecific fragments constructed by gene fusion (WO94/13804; 58). Fv, scFv or diabody molecules may be stabilised by the incorporation of disulphide bridges linking the VH and VL domains. Minibodies comprising a scFv joined to a CH3 domain may also be made.

As used herein, antibody molecule and immunotoxin are intended to encompass recombinant antibodies and recombinant immunotoxins, respectively (e.g., Fab, scFv or SC mAb linked through a cleavable peptide linker to a recombinant ribosomal inhibiting protein). Additionally or alternatively, the first and second antibody molecules may be provided as a single bispecific (anti-CD3/anti-CD7) antibody, thereby providing a bispecific immunotoxin such as anti-CD3/CD7-rRTA.

In relation to an antibody molecule, the term "selectively binds" may be used herein to refer to the situation in which one member of a specific binding pair will not show any significant binding to molecules other than its specific binding partner(s). The term is also applicable where e.g. an antigen-binding site is specific for a particular epitope that is carried by a number of antigens, in which case the specific binding member carrying the antigen-binding site will be able to bind to the various antigens carrying the epitope.

The antibody that selectively binds CD3 may in some cases comprise the complementarity determining regions (CDRs) of the antibody SPV-T3a. In accordance with IMGT numbering system (Lefranc, M.-P. et al., *Nucleic Acids Research*, 1999, Vol. 27, pp. 209-212, incorporated herein by reference) the CDRs of SFV-T3a are: CDRH1-H3: SEQ ID NOs: 5-7; CDRL1-L3: SEQ ID NOs: 8-10. In some cases the antibody that selectively binds CD3 may comprise the V of SPV-T3a (SEQ ID NO: 3) and/or the $V_L$ of SPV-T3a (SEQ ID NO: 4). In certain embodiments, the antibody that selectively binds CD3 may be the SPV-T3a antibody having the heavy chain of SEQ ID NO: 1 and light chain of SEQ ID NO: 2.

The antibody that selectively binds CD7 may in some cases comprise the complementarity determining regions (CDRs) of the antibody WT1. In accordance with IMGT numbering system (Lefranc, M.-P. et al., *Nucleic Acids Research*, 1999, Vol. 27, pp. 209-212, incorporated herein by reference) the CDRs of WT1 are: CDRH1-H3: SEQ ID NOs: 15-17; CDRL1-L3: SEQ ID NOs: 18-20. In some cases the antibody that selectively binds CD7 may comprise the $V_H$ of WT1 (SEQ ID NO: 13) and/or the $V_L$ of WT1 (SEQ ID NO: 14). In certain embodiments, the antibody that selectively binds CD7 may be the WT1 antibody having the heavy chain of SEQ ID NO: 11 and light chain of SEQ ID NO: 12.

SPV-T3a

Figure 9:
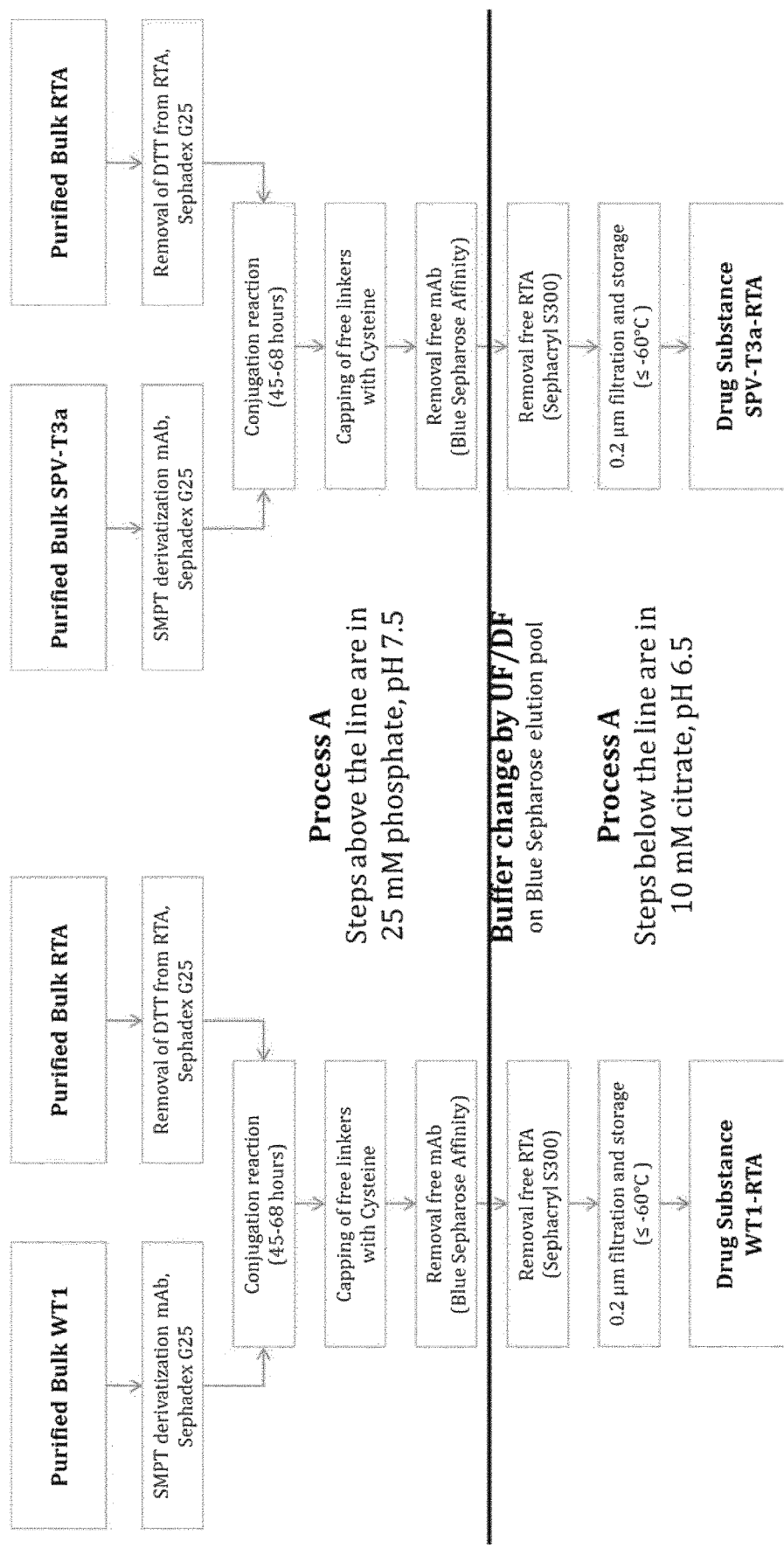
FIG. 9 shows a flow-chart depiction of the step-by-step process for preparing and purifying the antibody-toxin conjugates to obtain pharmaceutically acceptable product compositions ("Process A"). The conjugation and purification steps above the central horizontal line are performed in the 25 mM phosphate buffer at pH 7.5; steps below the horizontal line are performed in the 10 mM citrate buffer at pH 6.5.
Figure 10:
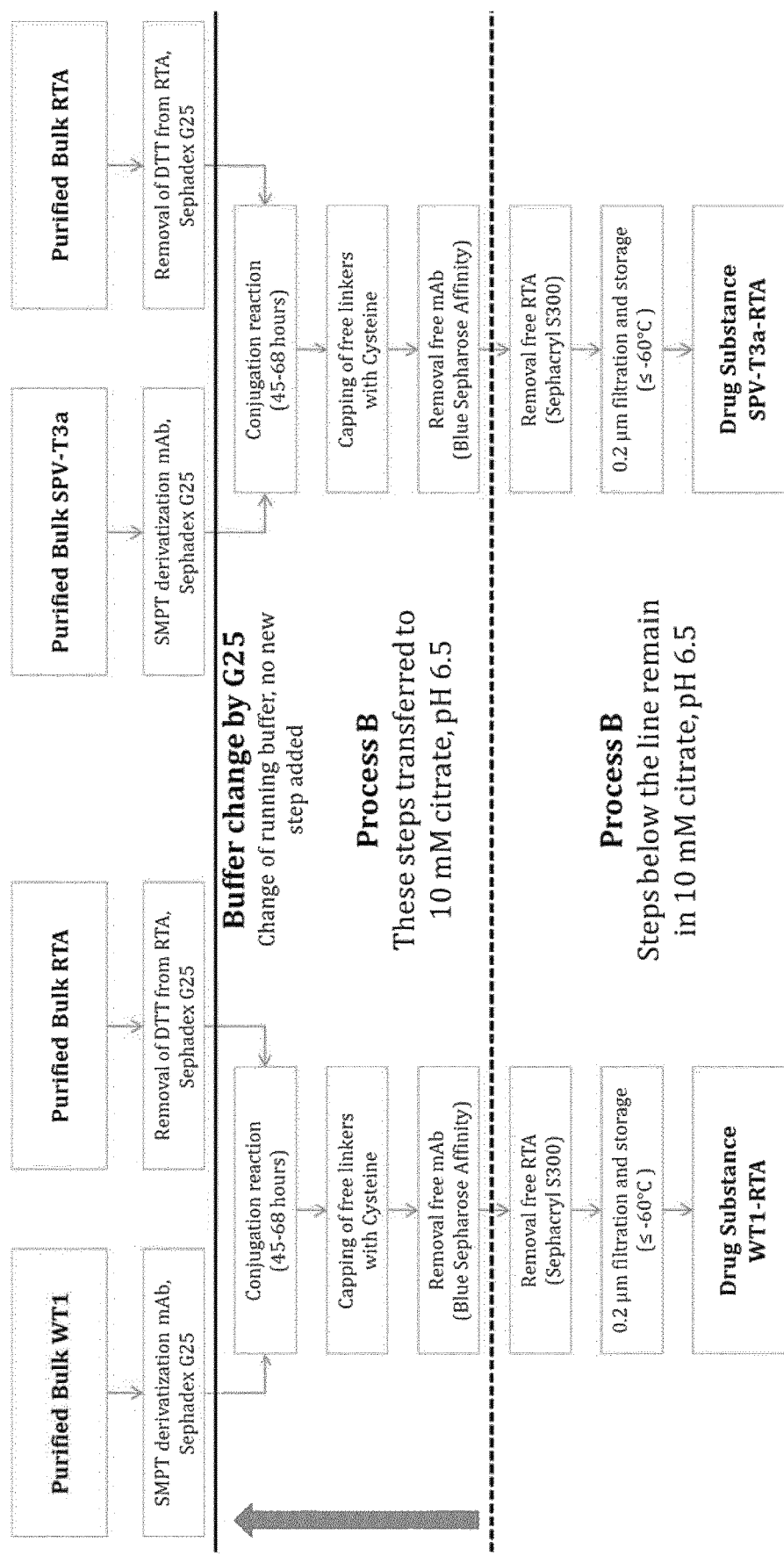
FIG. 10 shows a flow-chart depiction of an alternative step-by-step process for preparing and purifying the antibody-toxin conjugates to obtain pharmaceutically acceptable product compositions ("Process B"). The difference relative to Process A is that the change to the 10 mM citrate buffer occurs further upstream at the point shown by the upper horizontal line. Steps below that upper horizontal line are performed in the 10 mM citrate buffer at pH 6.5.

SPV-T3a is a murine IgG2b monoclonal antibody that selectively binds human CD3, a T cell surface glycoprotein composed of a CD3γ chain (UniProt: P09693), a CD3δ chain (UniProt: P04234), and two CD3ε chains (UniProt: P07766). The production and characterization of SPV-T3a is described in Spits et al., *Hybridoma*, 1983, Vol. 2, pp. 423-437, the entire content of which is expressly incorporated herein by reference. As described herein, the SVP-T3a antibody may be conjugated to ricin toxin A (RTA), for example deglycosylated ricin toxin A, using the 4-succinimidyloxocarbonyl-α-methyl-α-(2-pyridyldithio)toluene ("SMPT") crosslinker. The average number of deglycosylated ricin toxin A molecules conjugated to each SPV-T3a antibody is believed to be approximately 1.5. This antibody conjugate may be referred to herein as SPV-T3a-RTA. Conjugation and purification may be carried out by the process depicted in FIG. 9 or the process depicted in FIG. 10.

The amino acid sequence of the SPV-T3a light chain and heavy chain were determined by extracting mRNA from hybridoma cell pellets, RT-PCR was performed and DNA sequenced on an ABI3130x1 Genetic Analyzer. Amino acid sequences were predicted and were corroborated by Mass Spectrometry analysis. The complementarity determining regions (CDRs) are as determined according to the IMGT numbering system (Lefranc, M.-P. et al., *Nucleic Acids Research*, 1999, Vol. 27, pp. 209-212, incorporated herein by reference).

The amino acid sequences of SPV-T3a heavy chain and light chain, respectively, are shown below.

```
SPV-T3a Heavy Chain:
                                                    (SEQ ID NO: 1)
  1   QVQLQQSGAE LARPGASVKM SCKASGYTFT SYTMHWVKQR PGQGLEWIGY

51   INPSSGYTNY IQRFKDKATL TADKSSSTAY MQVSSLTSED SAVYYCARGS

101   RYDYYGMDYW GQGTSVTVSS AKTTPPSVYP LAPGCGDTTG SSVTLGCLVK

151   GYFPESVTVT WNSGSLSSSV HTFPALLQSG LYTMSSSVTV PSSTWPSQTV

201   TCSVAHPASS TTVDKKLEPS GPISTINPCP PCKECHKCPA PNLEGGPSVF

251   IFPPNIKDVL MISLTPKVTC VVVDVSEDDP DVQISWFVNN VEVHTAQTQT

301   HREDYNSTIR VVSTLPIQHQ DWMSGKEFKC KVNNKDLPSP IERTISKIKG

351   LVRAPQVYIL PPPAEQLSRK DVSLTCLVVG FNPGDISVEW TSNGHTEENY

401   KDTAPVLDSD GSYFIYSKLN MKTSKWEKTD SFSCNVRHEG LKNYYLKKTI

451   SRSPGK
```

VH domain is underlined; CDRH1-H3 are shown in bold and curved underlined.

```
SPV-T3a Light Chain:
                                                    (SEQ ID NO: 2)
  1   QIVLTQSPAI MSASPGEKVT MTCSASSSVS YMHWYQQKSG TSPKRWIYDT

51   SKLASGVPAR FSGSGSGTSY SLTISSMEAE DAATYYCQQW SSNPLTFGAG

101   TKLELKRADA APTVSIFPPS SEQLTSGGAS VVCFLNNFYP KDINVKWKID

151   GSERQNGVLN SWTDQDSKDS TYSMSSTLTL TKDEYERHNS YTCEATHKTS

201   TSPIVKSFNR NEC
```

VL domain is underlined; CDRL1-L3 are shown in bold and curved underlined.

```
SFV-T3a-VH:
                                                    (SEQ ID NO: 3)
  1   QVQLQQSGAE LARPGASVKM SCKASGYTFT SYTMHWVKQR PGQGLEWIGY

51   INPSSGYTNY IQRFKDKATL TADKSSSTAY MQVSSLTSED SAVYYCARGS

101   RYDYYGMDYW GQGTSVTVSS
```

-continued

```
SPV-T3a-VL:
                                                        (SEQ ID NO: 4)
  1  QIVLTQSPAI MSASPGEKVT MTCSASSSVS YMHWYQQKSG TSPKRWIYDT

51  SKLASGVPAR FSGSGSGTSY SLTISSMEAE DAATYYCQQW SSNPLTFGAG

101  TKLELKR

SPV-T3a-CDRH1:
                                                        (SEQ ID NO: 5)
GYTFTSYT

SPV-T3a-CDRH2:
                                                        (SEQ ID NO: 6)
INPSSGYT

SPV-T3a-CDRH3:
                                                        (SEQ ID NO: 7)
ARGSRYDYYGMDY

SPV-T3a-CDRL1:
                                                        (SEQ ID NO: 8)
SSVSY

SPV-T3a-CDRL2:
                                                        (SEQ ID NO: 9)
DTS

SPV-T3a-CDRL3:
                                                        (SEQ ID NO: 10)
QQWSSNPLT
```

WT1

WT1 is a murine IgG2a monoclonal antibody that selectively binds human CD7 (UniProt: P09564), a transmembrane protein which is a member of the immunoglobulin superfamily and is found on thymocytes and mature T cells. The production and characterization of WT1 is described in Tax et al., *Hamatol Bluttransfus*, 1983, Vol. 28, pp. 139-141 and Tax et al., *Clin Exp Immunol*, 1984, Vol. 55, pp. 427-436, the contents of both of which are expressly incorporated herein by reference. As described herein, the WT1 antibody may be conjugated to ricin toxin A (RTA), for example deglycosylated ricin toxin A, using the SMPT crosslinker. The average number of deglycosylated ricin toxin A molecules conjugated to each WT1 antibody is believed to be approximately 1.5. This antibody conjugate may be referred to herein as WT1-RTA. Conjugation and purification may be carried out by the process depicted in FIG. 9 or the process depicted in FIG. 10. WT1 is commercially available. For example, the anti-CD7 antibody (clone WT1) is sold by LifeSpan BioSciences, Inc. under catalogue number: LS-C122885-1000 (1000 μl in PBS, 0.1% sodium azide) for research use, e.g., immunofluorescence and immunohistochemistry.

The amino acid sequence of the WT1 light chain and heavy chain were determined by extracting mRNA from hybridoma cell pellets, RT-PCR was performed and DNA sequenced on an ABI3130x1 Genetic Analyzer. Amino acid sequences were predicted and were corroborated by Mass Spectrometry analysis. The complementarity determining regions (CDRs) are as determined according to the IMGT numbering system (Lefranc, M.-P. et al., *Nucleic Acids Research*, 1999, Vol. 27, pp. 209-212, incorporated herein by reference).

The amino acid sequences of WT1 heavy chain and light chain, respectively, are shown below.

```
WT1 Heavy Chain:
                                                        (SEQ ID NO: 11)
  1  QIQLVQSGPE LKKPGETVKI SCKASGYTFT NYGMNWVKQA PGKGLMWLGW

51  INTYTGEPTY ADDFKGRFAF SLETSASTAY LQINNLKNED TATYFCARWA

101  YFYGSSPYFF DYWGQGTTLT VSSAKTTAPS VYPLAPVCGD TTGSSVTLGC

151  LVKGYFPEPV TLTWNSGSLS SGVHTFPAVL QSDLYTLSSS VTVTSSTWPS

201  QSITCNVAHP ASSTKVDKKI EPRGPTIKPC PPCKCPAPNL LGGPSVFIFP

251  PKIKDVLMIS LSPIVTCVVV DVSEDDPDVQ ISWFVNNVEV HTAQTQTHRE

301  DYNSTLRVVS ALPIQHQDWM SGKEFKCKVN NKDLPAPIER TISKPKGSVR

351  APQVYVLPPP EEEMTKKQVT LTCMVTDFMP EDIYVEWTNN GKTELNYKNT
```

```
401  EPVLDSDGSY FMYSKLRVEK KNWVERNSYS CSVVHEGLHN HHTTKSFSRT

451  PGK
```

VH domain is underlined; CDRH1-H3 are shown in bold and curved underlined.

```
WT1 Light Chain:
                                              (SEQ ID NO: 12)
  1  QAVVTQESAL TTSPGETVTL TCRSSTGAVT TSNYANWVQE KPDHLFTGLI

51  GGTNNRAPGV PARFSGSLIG DKAALTITGA QTEDEAIYFC ALWCSNHLVF

101  GGGTKLTVLG QPKSSPSVTL FPPSSEELET NKATLVCTIT DFYPGVVTVD

151  WKVDGTPVTQ GMETTQPSKQ SNNKYMASSY LTLTARAWER HSSYSCQVTH

201  EGHTVEKSLS RADCS
```

VL domain is underlined; CDRL1-L3 are shown in bold and curved underlined.

```
WT1-VH:
                                              (SEQ ID NO: 13)
  1  QIQLVQSGPE LKKPGETVKI SCKASGYTFT NYGMNWVKQA PGKGLMWLGW

51  INTYTGEPTY ADDFKGRFAF SLETSASTAY LQINNLKNED TATYFCARWA

101  YFYGSSPYFF DYWGQGTTLT VSS

WT1-VL:
                                              (SEQ ID NO: 14)
  1  QAVVTQESAL TTSPGETVTL TCRSSTGAVT TSNYANWVQE KPDHLFTGLI

51  GGTNNRAPGV PARFSGSLIG DKAALTITGA QTEDEAIYFC ALWCSNHLVF

101  GGGTKLTVL

WT1-CDRH1:
                                              (SEQ ID NO: 15)
GYTFTNYG

WT1-CDRH2:
                                              (SEQ ID NO: 16)
INTYTGEP

WT1-CDRH3:
                                              (SEQ ID NO: 17)
ARWAYFYGSSPYFFDY

WT1-CDRL1:
                                              (SEQ ID NO: 18)
TGAVTTSNY

WT1-CDRL2:
                                              (SEQ ID NO: 19)
GTN

WT1-CDRL3:
                                              (SEQ ID NO: 20)
ALWCSNHLV
```

Graft Versus Host Disease (GVHD)—Acute and Chronic

GVHD is a medical complication following the receipt of transplanted tissue from a genetically different person. GVHD is commonly associated with stem cell transplant (bone marrow transplant), but the term also applies to other forms of tissue graft. Immune cells in the donated tissue (the graft) recognize the recipient (the host) as foreign (nonself). The transplanted immune cells then attack the host's body cells. Traditionally, GVHD that occurred within the first 100 days after transplantation was arbitrarily classified as acute, whereas GVHD that was still present, or developed, at a later stage was referred to as chronic GVHD. The current viewpoint is that chronic GVHD is not simply a continuation of acute GVHD (Toubai et al. 2008, Flowers et al. 2011). While there is significant overlap between the organs involved in acute and chronic GVHD, the distribution of affected organs in chronic GVHD is much broader, including also the eyes, lungs, salivary glands, and esophagus. Based on histological signs, acute GVHD is dominated by apoptosis and necrosis, whereas chronic GVHD represents an inflammatory and fibrotic process similar to as seen in certain autoimmune disorders (Higman et al. 2004, Filipovich et al. 2005). Although acute GVHD is highly associated with subsequent chronic GVDH, approximately 20-30% of people with acute GVHD do not develop chronic GVHD later. Moreover, 25-35% of chronic GVHD is 'de novo' without any preceding acute manifestations (Lee 2005).

As used herein "providing a clinical benefit as measured by the incidence of grade 3 or above capillary leak syndrome (CLS)" means avoiding development of grade 3 or above capillary leak syndrome or vascular leak syndrome (VLS) in a patient administered the composition of the present invention, for example as assessed between 1 and 100, e.g. between 1 and 10 days following administration of said composition. CLS/VLS grading may be as defined in Sausville et al., *Blood*, 1995, Vol. 85, No. 12, pp. 3457-3465, the contents of which are expressly incorporated herein by reference. In particular, the NCI Common Toxicity criteria were used. Vascular leak was specifically graded as follows: grade 1, minimal ankle pitting edema; grade 2, ankle pitting edema and weight gain, but total weight gain of less than 10 lb; grade 3, peripheral edema with a weight gain of greater than 10 lb or pleural effusion with no pulmonary function deficit documented; grade 4, anasarca, pleural effusion or ascites with pulmonary function deficit or pulmonary edema; and grade 5, respiratory failure requiring mechanical ventilation in the setting of pulmonary edema or hypotension requiring pressor support.

Pharmaceutical Compositions and Administration Thereof

The compositions of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient may be in the form of a parenterally acceptable aqueous solution or liquid which is pyrogen-free and has suitable pH, tonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient(s), the compositions can comprise one or more of a pharmaceutically acceptable excipient, carrier, buffer, stabiliser, tonicising adjusting agent, preservative or anti-oxidant or other materials well known to those skilled in the art. Such materials should be non-toxic and should not interfere with the efficacy of the active ingredient. The precise nature of the carrier or other material may depend on the route of administration, e.g., intravenous injection.

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

In particular cases, the pharmaceutical compositions of the present invention may be administered, or for administration, at a dose of approximately 4 $mg/m^2$ Body Surface Area (BSA). The pharmaceutical compositions of the present invention may advantageously be administered, or for administration, as multiple infusions, e.g. four 4-hour infusions given at 48-hour intervals.

The following is presented by way of example and is not to be construed as a limitation to the scope of the claims.

EXAMPLES

Example 1—Prolonged Survival of Graft Vs. Host Disease Patients Following Treatment with T-Guard® Immunotoxin Cocktail The investigational product is an immunotoxin-combination named T-Guard®, consisting of equal amounts (w/w) of two murine antibodies (mAb) SVP-T3a (anti-CD3, IgG2b) and WT1 (anti-CD7, IgG2a), each conjugated to the recombinant ricin toxin A-chain (RTA): SPV-T3a-RTA and WT1-RTA. T-Guard is administered intravenously to human GvHD patients as four 4-hour infusions given at 48-hour intervals. Each dose consists of 4 $mg/m^2$ Body Surface Area (BSA). Typically, the estimated BSA will lie somewhere between 1.4 and 2.5 $m^2$ (small person—large person). If a patient's BSA is more than 2.5 $m^2$, the dose calculation should use 2.5 $m^2$.

Figure 2:
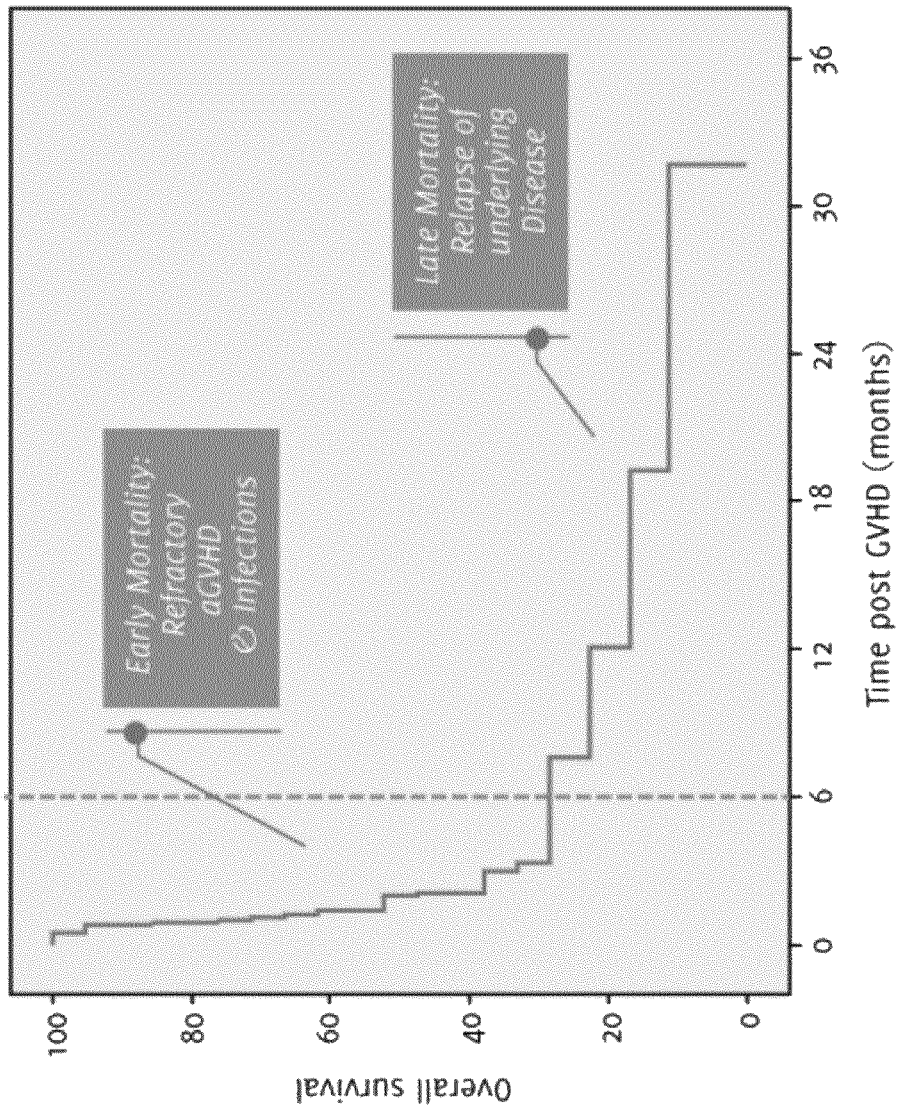
FIG. 2 shows a survival curve (survival on the y-axis plotted against time in months post-GvHD on the x-axis) for patients treated with the control (institutional standard of care). An initial phase <6 months exhibits a rapid decline in survival associated with refractory GvHD and infections; a later phase >6 months exhibits a slower decline in survival associated with relapse of underlying disease.
Figure 3:
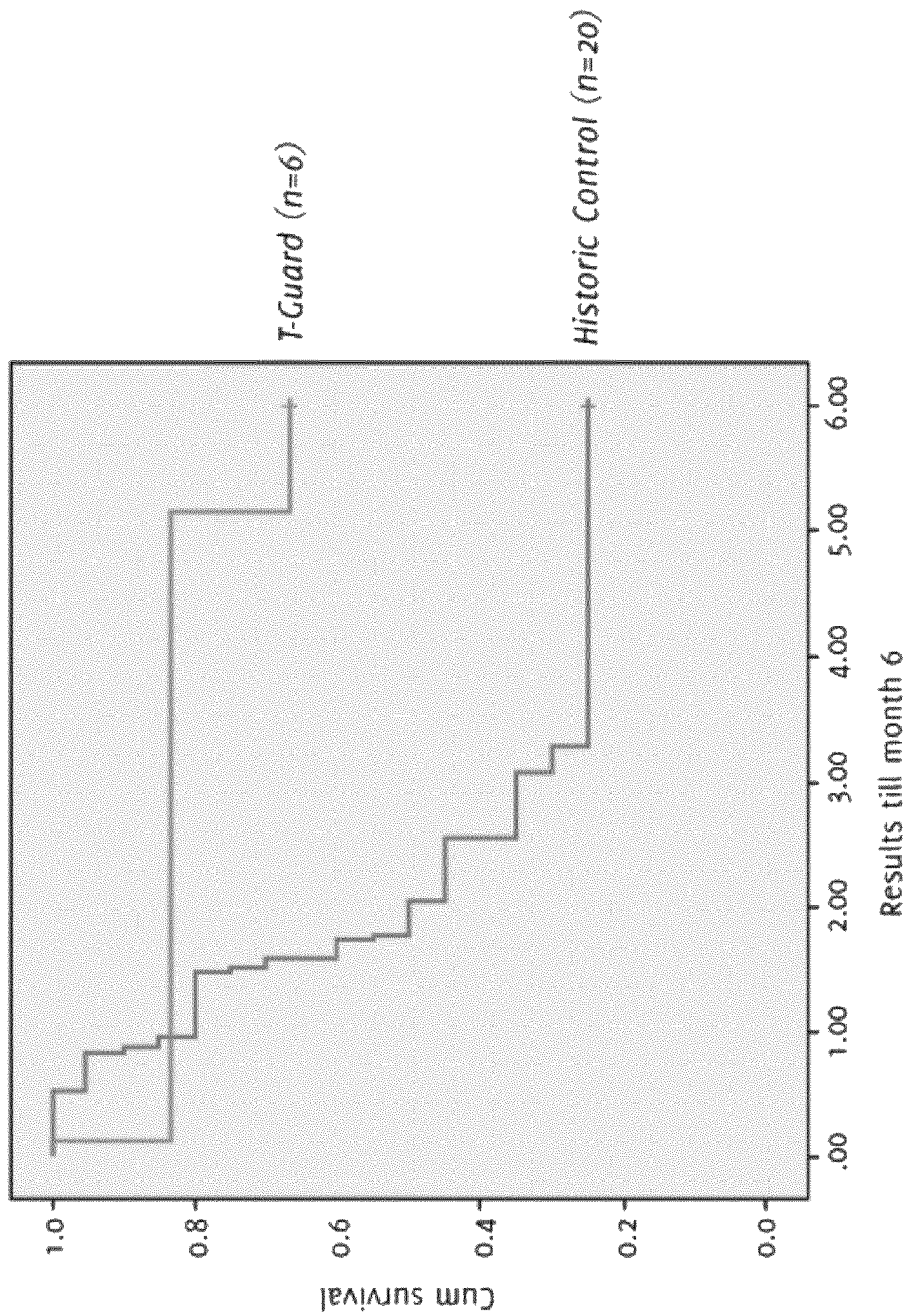
FIG. 3 shows two survival curves (survival on the y-axis plotted against time in months post-GvHD on the x-axis) for patients treated with the control (institutional standard of care) (n=20) and T-Guard® (n=6) up to 6 months. The T-Guard®-treated patients exhibit higher survival than the control group.

Of seven GvHD patients in the group to be treated with T-Guard®, one was positive for CMV and one was positive for EBV just prior to the start of the T-Guard® treatment. No new re-activations of EBV or CMV after start of the T-Guard® treatment were seen. Of the 21 patients treated with the institutional standard of care (SoC) consisting of a combination of inolimomab (trade name Leucotac, anti-CD25) and etanercept (trade name Enbrel, anti-TNF), 2 patients developed a probable invasive mould disease, 2 patients developed a CMV infection (one progressing to CMV colitis), 2 patients developed an adenovirus infection, and 3 patients developed an EBV infection. As shown in FIG. 1, day 28 response rate and 6-month survival were both superior in the T-Guard®-treated group compared with control. FIG. 2 shows a survival curve for patients treated with Institutional SoC. A marked early mortality phase (<6 months) is evident. This early mortality period is associated with both refractory GvHD and with viral infection or reactivation (see also van Groningen et al., *Biol. Blood Marrow Transplant,* 2016, Vol. 22, pp. 170-182. FIG. 3 shows survival curves for T-Guard®-treated patients versus Institutional SoC, up to the 6-month time point. It is clear that cumulative survival is higher among the T-Guard®-treated patients.

Example 2—Spontaneous Resolution of Viral Reactivation Among Graft Vs. Host Disease Patients Treated with T-Guard® Immunotoxin Cocktail A further investigation was carried out in which GvHD patients exhibiting positive virus titres were treated with T-Guard® (same dosage amount and interval as described above in Example 1) and monitored for CMV and EBV viral titres over time.

CMV titre was measured by real-time quantitative PCR, essentially as described in Kalpoe et al., *J. Clin. Microbiol.,* 2004, Vol. 42, No. 4, pp. 1498-1504, the entire contents of which are expressly incorporated herein by reference.

EBV titre was measured by real-time quantitative PCR, essentially as described in Niesters et al., *J. Clin. Microbial.,* 2000, Vol. 38, pp. 712-715, the entire contents of which are expressly incorporated herein by reference.

Figure 4:
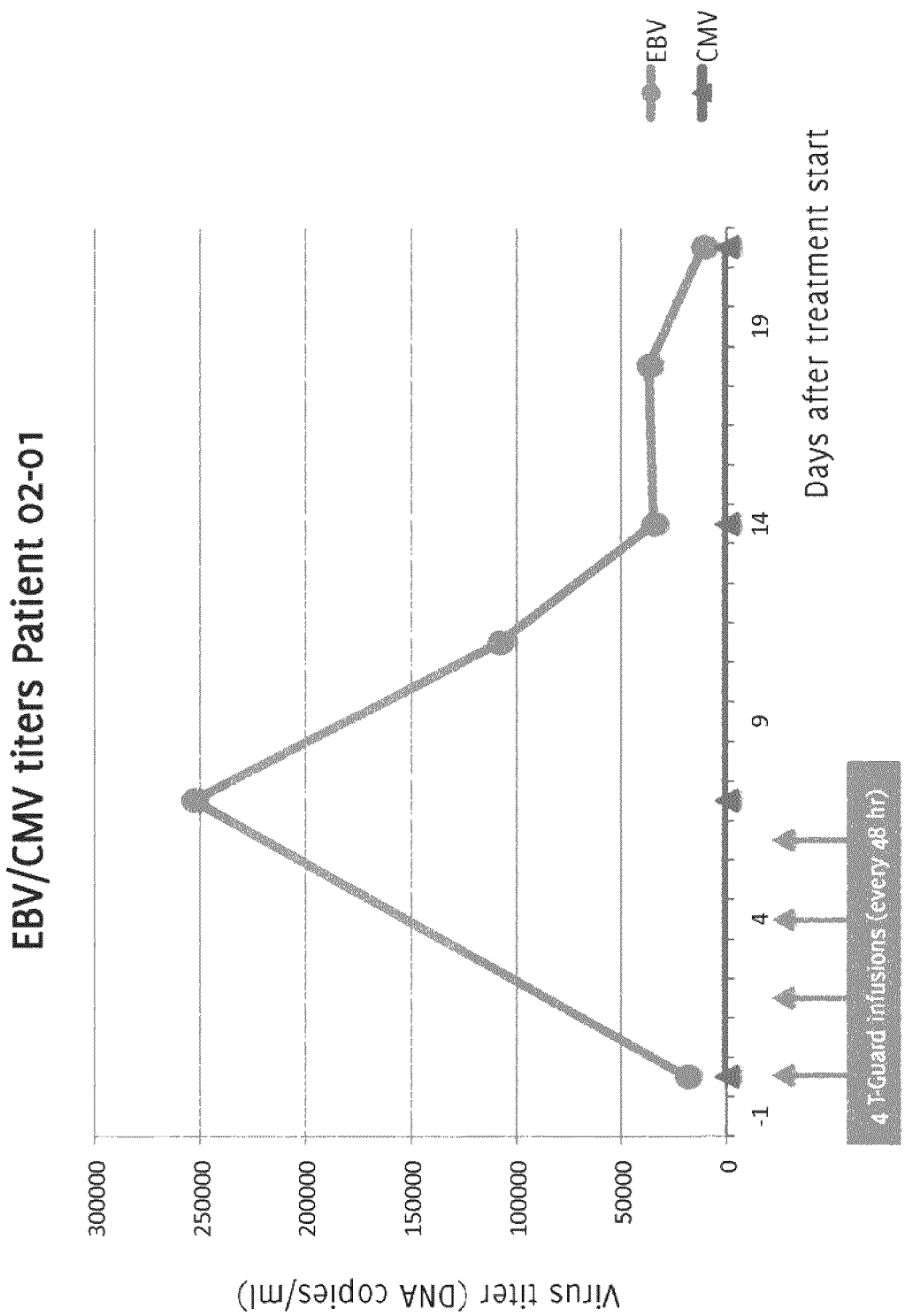
FIG. 4 shows a plot of EBV (circles) and CMV (triangles) titres plotted against time in days after treatment start for a patient treated with T-Guard® (four infusions given at 48-hour intervals as indicated by the arrows). It is clear that after T-Guard® treatment and subsequent wash-out, the EBV titre, which had reached a measured level of 250000 DNA copies/ml, exhibited a significant decline over subsequent days.
Figure 5:
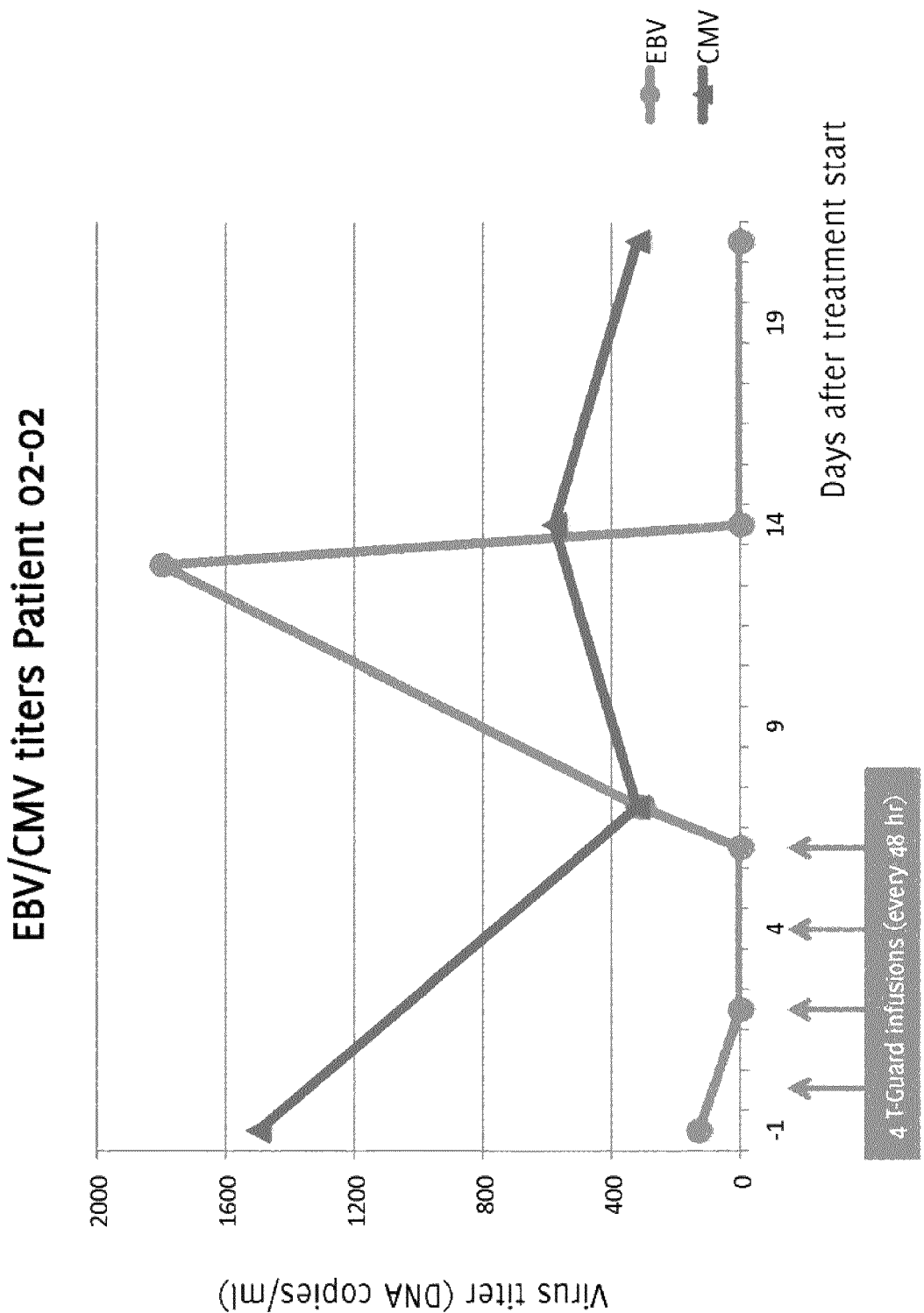
FIG. 5 shows a plot of EBV (circles) and CMV (triangles) titres plotted against time in days after treatment start for a patient (different patent than that treated in FIG. 4) treated with T-Guard® (four infusions given at 48-hour intervals as indicated by the arrows). It is clear that after T-Guard® treatment the CMV titre declined. Moreover, after T-Guard® treatment and subsequent wash out, 14 days after the start of treatment, a significant decline in EBV titre was seen.

Two GvHD patients exhibited positive virus titres at screening, despite prophylaxis with Aciclovir®. The first patient was positive for EBV, the second patient for both EBV and CMV. Especially the first patient showed a massive increase in EBV titre in the first week after T-Guard® treatment start, amounting to 250000 DNA copies/ml (see FIG. 4). Surprisingly, the EBV titre then resolved in the next two weeks without further intervention in the form of rituximab or therapeutic CTLs. A similar response was seen in the second patient, for both EBV and CMV, although at lower titres (see FIG. 5).

Figure 6:
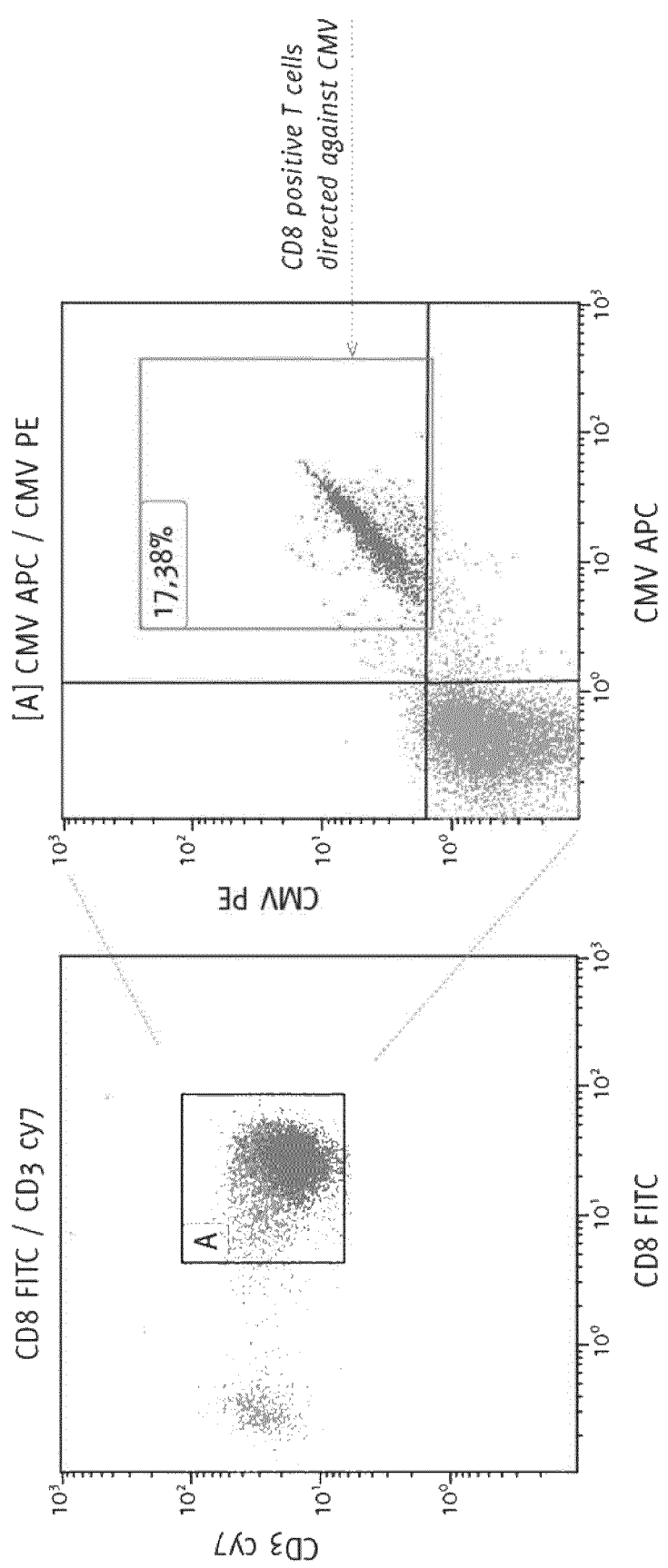
FIG. 6 shows an example from one patient of FACS cell sorting results obtained from patients treated with T-Guard®. The left-hand panel shows CD3 cy7 plotted against CD8 FITC. The right-hand panel shows CMV PE plotted against CMV APC. Analysis of circulating T cells of patient 02-02 with tetramers revealed a large fraction (17.38%) of CMV-reactive cells within the CD8 positive T cell fraction, within 3 weeks after treatment start.

Tetramer analysis of the Day 21-blood sample of the second patient showed that his CD8 positive cells included 17% that were CMV-directed T-cells (see FIG. 6). Without wishing to be bound by any particular theory, the present inventors believe that the anti-CMV T-cells, relatively spared by T-Guard® treatment, are able to keep the patient's CMV titre low. It is further contemplated that staining with HLA-matching EBV tetramers will be performed. The resolution of EBV reactivation in the second week after treatment start clearly suggests that there must be EBV-directed T-cells present as well (see FIG. 5).

Figure 11:
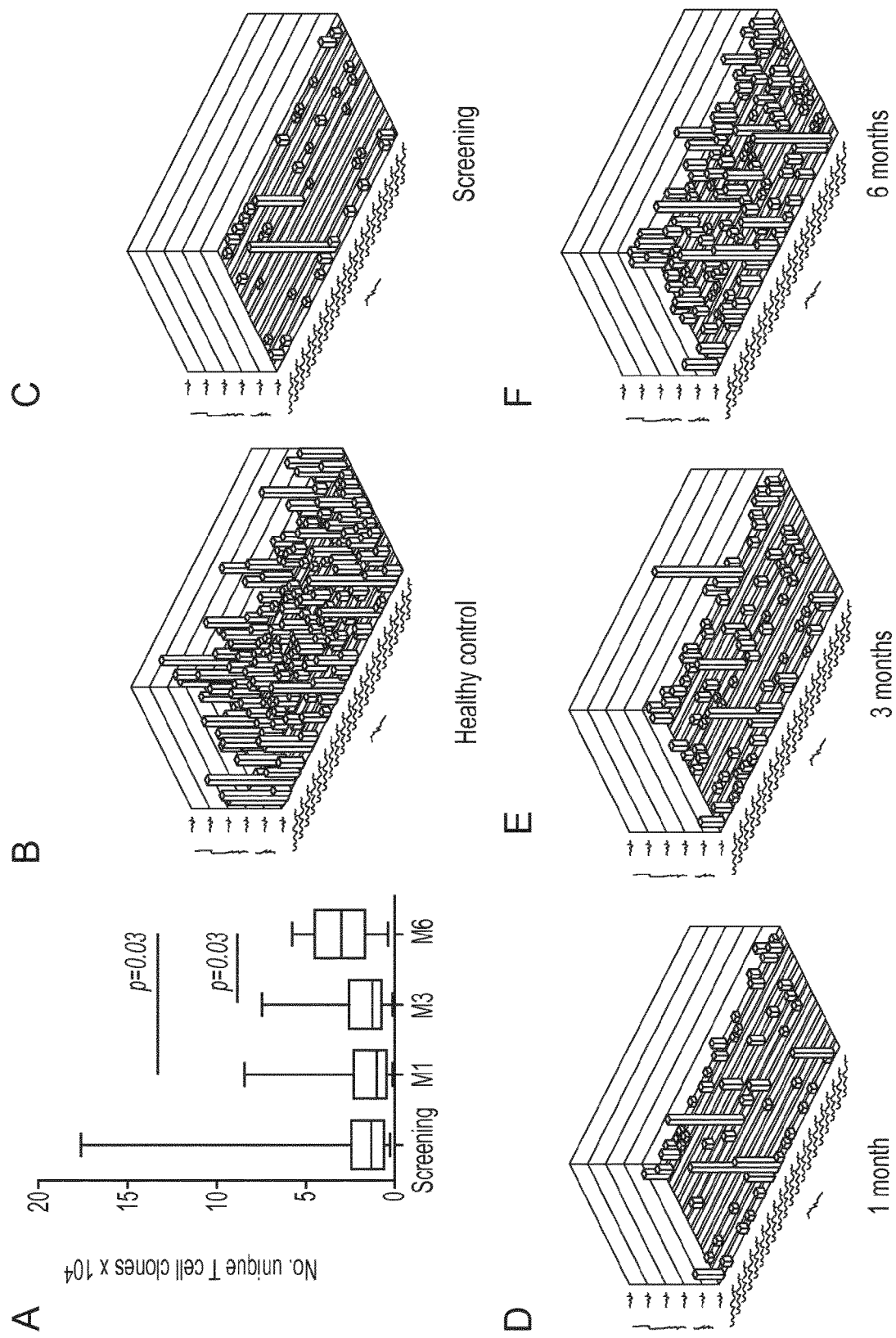
FIG. 11 shows that T-Guard® treatment induces a swift immune reconstitution with a diverse T cell repertoire. (A) The number of unique T cell clones, as measured by the total number of unique CDR3 sequences, are shown for 21 patients before (screening) and at 1 month (Ml), 3 months (M3) and 6 months (M6) after T-Guard® therapy (Wilcoxon matched-paired signed rank test). There is significant increase of unique T cell clones within the first 6 months after T-Guard® therapy, highlighting a diversity expansion within T cells. The blood T cells repertoires of a single patient before T-Guard® therapy (C), 1 month (D), 3 months (E) and 6 months (F) after therapy.

The present example demonstrates patients recovering from steroid-resistant acute GvHD and successfully fighting (pre-existing) infections within 2-3 weeks after receiving T-Guard® treatment. The fact that both these patients are 'stable' GvHD responders suggests that T-Guard® preferentially eliminates allo-reactive T-cells over anti-viral T-cells. It is presently thought that what is being seen is a relative sparing of anti-viral cells, which might then expand by lymphopenia-induced homeostatic proliferation after T-Guard® has been washed away (within 1-2 days after last infusion). Further support for this conclusion comes from the expanded T cell repertoire shown in FIG. 11.

Example 3—a Phase I/II Study on the Anti-CD3/CD7 Immunotoxin Combination (T-Guard®) for the Treatment of Steroid-Refractory Acute GVHD Background More effective therapies for steroid-refractory acute graft-versus-host disease (SR-aGVHD) are urgently needed. Because infections and relapse of the hematological malignancy contribute to the dismal overall survival (OS), therapies that limit the duration of immune suppression after achieving a remission might be preferred. The immunotoxin (IT)-combination (T-Guard®) consists of two antibody-drug conjugates (i.e. Ricin A) that target CD3 and CD7 on activated T lymphocytes and has shown efficacy as third-line therapy in SR-aGVHD while allowing fast immune reconstitution. T-Guard® is therefore a composition in accordance with the various aspects of the present invention.

Objectives

We conducted a prospective phase I/II multicenter trial on the safety and efficacy of T-Guard® for the treatment of SR-aGVHD (NCT02027805).

Methods

Adult patients with grade II-IV SR-aGVHD were eligible for inclusion. Exclusion criteria consisted of the presence of uncontrolled infections, signs of chronic GVHD, severe renal impairment and severe hypoalbuminemia. T-Guard® was given as 4-hour intravenous infusions every 48 hours for a total of 4 doses of each 4 mg/m2. The primary efficacy endpoint was defined as overall clinical response (ORR) on day 28. The main secondary endpoints were the 6-month OS and the safety and tolerability.

Results

Between June 2014 and September 2016 the planned 20 adult patients were included in two European centers. Patients, 11 female and 9 male, with a median age of 53 years (range 18-74) all had received an allogeneic stem cell transplantation for myeloid and lymphoid malignancies. All but two completed the planned 8 days of treatment with T-Guard®. SR-aGVHD was grade II in 3 patients (15%), III in 11 (55%), and IV in 7 (35%). In most patients 2 organs were involved (16/20, 80%), with gastro-intestinal (GI) and liver involvement in 18 and 5 cases, respectively. Baseline albumin levels were median 23 gr/L (range: 16-34; N 35-50 gr/L) and based on the 2-biomarker model (ST2 and REG3α) no patients were classified as low-risk (<0.08), and 50% as high-risk (0.32). The 2-biomarker model is further described in WO 2013/066369, the entire content of which is expressly incorporated herein by reference.

Figure 7:
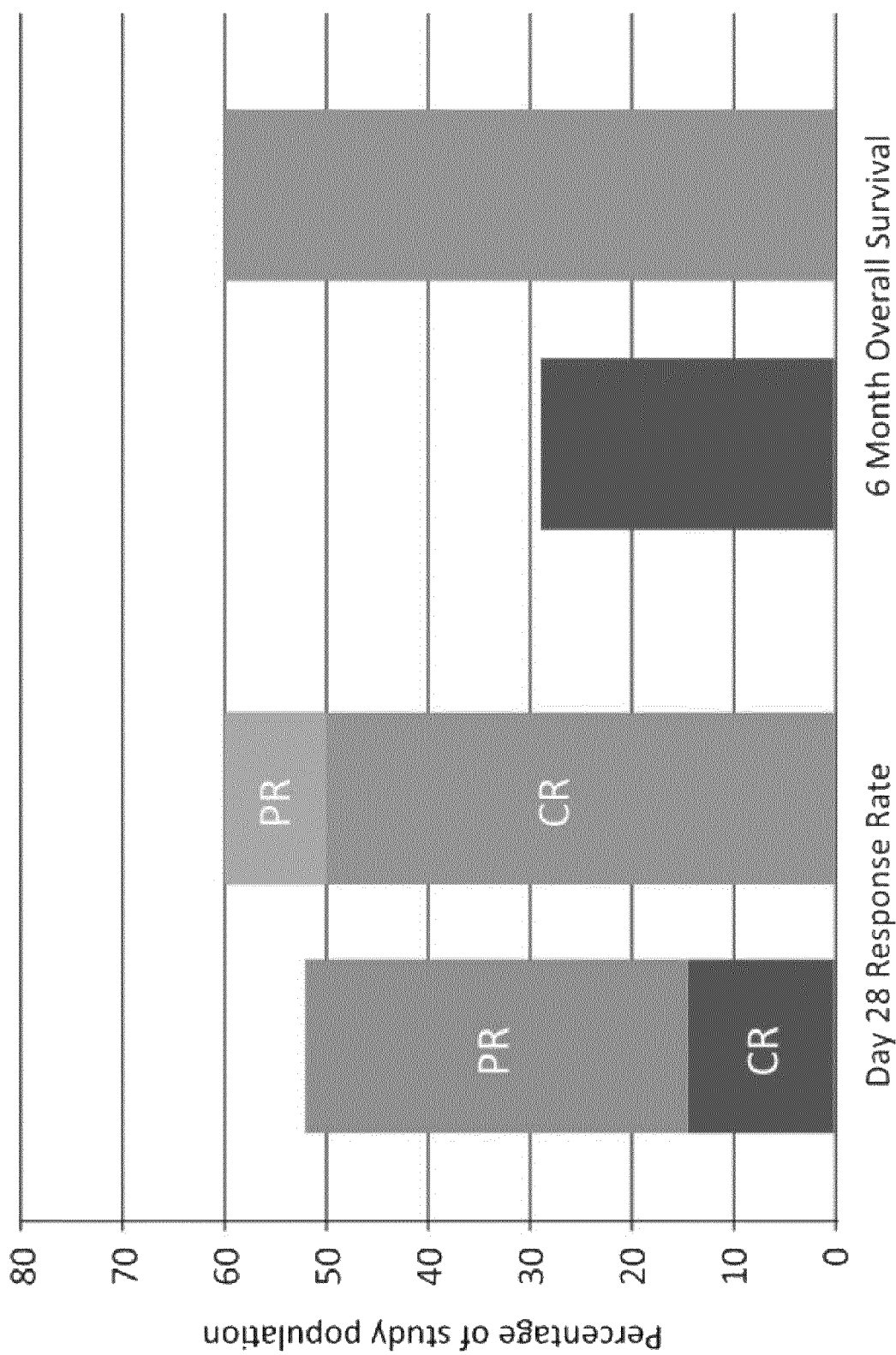
FIG. 7 shows overall clinical response (ORR) at day 28 and overall survival (OS) at 6 months for T-Guard®-treated patients and patients treated with the historical controls. The T-Guard®-treated results (n=20) are shown in bars 2 and 4; the historical controls (n=42; Nijmegen, NL (n=21): inolimomab/etanercept; Münster, DE (n=21): infliximab) are shown in bars 1 and 3. CR=Complete Response (lower bar portions in darker shading of bars 1 and 2). PR=Partial Response (upper bar portions in lighter shading). The y-axis shows the percentage of the study population. CR and OS are higher among the T-Guard®-treated patients than the historical controls.
Figure 8:
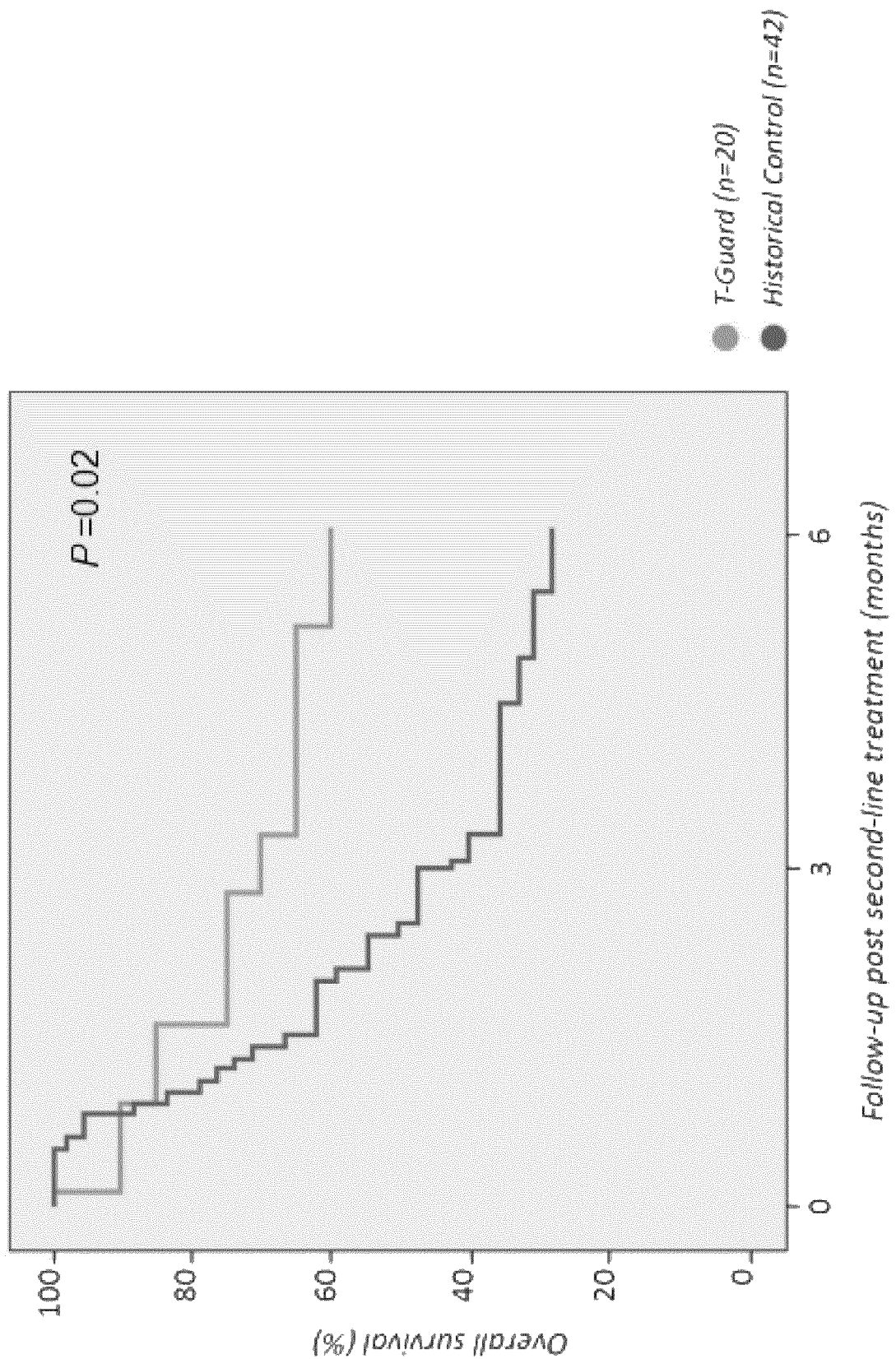
FIG. 8 shows Kaplan Meijer curves of overall survival (OS) of the patients treated with T-Guard® (n=20; orange; upper curve from around 1 month onwards) and the historical controls (n=42; grey; lower curve from around 1 month onwards). The y-axis is OS (%); the x-axis is time (months) follow-up post-second line treatment. Six month OS was 60% for T-Guard®-treated vs. 29% for historical controls. A Cox regression analysis gave P=0.02.

On day 28, 12 patients had achieved a clinical response (ORR: 12/20, 60%), with 10 (50%) achieving a complete remission (CR), FIG. 7. In those with a high-risk biomarker profile a CR was achieved in 50%. With a minimum follow-up of 6 months 12 patients were alive (6-month OS 60%), FIG. 7. The cause of death in the other eight patients was refractory aGVHD (N=4), refractory GVHD and infection (N=3) and pseudomembranous colitis (N=1). Of those receiving the planned treatment the ORR, CR rate and 6-month OS were 60%, 50%, and 60% respectively. The outcomes compared favorably with historical controls receiving either infliximab (N=21) or inolimomab/etanercept (N=21) were the ORR was 52% and the 6-month OS 29% (FIGS. 7 and 8).

No significant infusion reactions were recorded, although two patients experienced chills on their first infusion, and after introduction of clemastine pre-infusion no infusion reactions were seen. As expected, the rate of overall infection and adverse events was high. However, there was a limited number of potentially attributable adverse events that occurred in more than one patient, and consisted of hypoalbuminemia, microangiopathy, and thrombocytopenia. Capillary Leak Syndrome occurred in only one patient, with edema requiring treatment with diuretics (grade 2). Early (<3 months) EBV and CMV infections were recorded in 3 patients each, but no CMV disease or PTLD occurred. Whilst only 40% received mould-active antifungal prophylaxis no invasive fungal disease (IFD) were seen. The low number and mild severity of side effects observed is considered unusual in comparison with other RTA immunotoxins. This suggests that the dose was able to produce a therapeutic effect while minimising side effects.

While the one-week treatment course was associated with an immediate depletion of T and NK cells, the T-Guard® IT-combination's short half-life (~9 hrs) allowed for a swift immune reconstitution accompanied by a diverse T cell receptor repertoire and without a negative effect on the fraction of anti-viral EBV and CMV-specific clones, as assessed by deep sequencing. Within 6 months there was a significant increase of unique T cell clones compared to the first month post-therapy (p=0.03) (see FIG. 11).

Of particular note, only 1 out of 12 patients was diagnosed with cGVHD symptoms 6 months (180 Days) after T-Guard® treatment in this Phase 1/2 study; this translates to a cGVHD incidence at 180 days of only 8.3%. Moreover, this cGVHD event was assessed to be "limited" only (see Table 1).

TABLE 1

Chronic GVHD Events

| cGVHD | % (n) | Pt. No. | Days Diagnosed | R/OS | Comments |
|---|---|---|---|---|---|
| Absent | 80% (16) | NA | NA | | |
| Limited | 15% (3) | 01-06* | Pre-study, and D28-56 | CR/A | End of study absent |
| | | 01-07** | Pre-study, and D02-56 | PR/D | End of study absent, cause of death: gut failure |
| | | 02-05 | D1B0 | CR/A | |
| Extensive | 5% (1) | 01-02 | End of study | CR/D | Cause of death: fever and intestinal failure |

*Signs and symptoms of cGVHD (mouth and skin) reported before enrolment.
**Patient had confirmed cGVHD reported in medical history.
CR = Complete Responder; PR = Partial Responder; A = Alive; D = Death.

The cGVHD rate for survivors at 6 months (180 days) is only 8.3% instead of the typical >40% incidence reported in the literature. In particular, the following cGVHD have been reported previously:

Furlong et al., *Bone Marrow Transplant.*, 2009, Vol. 44, No. 11, pp. 739-748: 73.3% for MMF after 100 Days (survivors only).
Socie et al., *Blood*, 2017, Vol. 129, No. 5, pp. 643-649: 75.4% for inolimomab and 80.2% for ATG after 1 year (survivors only); all events were assessed to be severe.
MacMillan et al., *Biology of Blood and Marrow Transplantation*, 2002, Vol. 8, pp. 40-46: 50.6% for ATG after 1 year (survivors only).
MacMillan et al., *Blood*, 2007, Vol. 109, No. 6, pp. 2657-2662: 44% for ABX-CBL an 46% for ATG relative to the patients who started treatment.

CONCLUSIONS

Treatment of SR-aGVHD with a short course of the T-Guard® proved to be safe and well tolerated, and resulted in a high rate of CR and a promising 6-month OS of 60%, especially considering the high-risk setting (90% GI involvement, 50% high-risk biomarker profile).

Furthermore, the study results surprisingly show that T-Guard®, a composition in accordance with the various aspects of the present invention, was able to preventatively treat cGVHD as assessed by incidence of cGVHD at 180 days after second-line treatment (i.e. T-Guard® administration) for SR-aGVHD. These results therefore indicate that T-Guard® may enjoy a secondary use in the preventative treatment of cGVHD among the patient group undergoing immunomodulatory treatment for aGVHD, including SR-aGVHD.

Absence of Severe RTA-Related Toxicities

One of the main safety concerns associated with the therapeutic use of RTA-based immunotoxins is capillary leak syndrome (CLS), followed by myalgia associated with elevated CK levels (Vitetta et al. 1991, Amlot et al. 1993, Conry et al. 1995, Sausville et al. 1995, Stone et al. 1996, Engert et al. 1997, Frankel et al. 1997, Schnell et al. 1998, Messmann et al. 2000, Schnell et al. 2000, Schindler et al. 2001, Schnell et al. 2002, Schnell et al. 2003, Schindler et al. 2011). The research group of Prof. Vitetta described for comparable immunotoxins that serum concentrations at or above 1 µg/ml (~0.5×10-8 M) were typically associated with the occurrence of serious RTA-associated side effects, predominantly consisting of CLS (Amlot et al. 1993, Sausville et al. 1995, Stone et al. 1996). Moreover, based upon a retrospective analysis of patients in five clinical trials, Schindler et al. concluded that the toxicity of RTA-based immunotoxins is exacerbated by prior radiotherapy (Schindler et al. 2001). Stone et al., 2001 and Sausville et al. 1995 reported that immunotoxin Cmax is positively correlated with CLS/VLS severity (see, e.g., FIG. 2 of Sausville et al., 1995).

Interestingly, as described herein, T-Guard® treatment did not induce any severe CLS or myalgia in any of the patients treated so far. Not in the Phase 1/2 trial, nor in the investigator-initiated dose escalation study, while all respective patients had received prior chemo- and radiotherapy, and Cmax values at or above 1 µg/ml were obtained in all patients. Although eight of the patients in the Phase 2 study were diagnosed to have some limited symptoms associated with CLS, 7 of these patients did not require treatment at all (mild CLS; Grade 1) and only one was treated with diuretics for edema (moderate CLS; Grade 2). Thus far, no severe cases of CLS have been reported in any of the 32 patients treated with T-Guard® (including the investigator-initiated dose escalation study and 'named patients'). There were also no observations of CK rise or treatment-related myalgia in the Phase 1/2 study (in the investigator-initiated dose escalation study, only 1 patient demonstrated a Grade 1 increase of plasma CK levels).

Without wishing to be bound by any particular theory, the present inventors postulate that the reason for T-Guard®'s favorable safety profile might be the partitioning of the RTA toxin over SPV-T3a and WT1 (half a dose each), which mAbs might have different systemic distribution profiles (and, thereby, causing a dilution of nonspecific toxicities)

due to differences in isoelectric point. Together with the presumed synergistic elimination of T cells by SPV-T3a-RTA and WT1-RTA, and the additive immunosuppression provided by SPV-T3a through inhibition of alloactivation, this might explain T-Guard®'s promising therapeutic window thus far observed.

By way of contrast, the use of Denileukin Diftitox (Ontak®) in Cutaneous T Cell Lymphoma (CTCL) has label warning "Delay administration of Ontak until serum albumin levels are at least 3.0 g/dL" (see ONTAK® US label revised 10/2009). Capillary leak syndrome was reported as occurring in 32.5% (76/234) of Ontak®-treated patients. The label warns: "Withhold Ontak for serum albumin levels of less than 3.0 g/dL". Moreover, Olsen et al., *J. Clin. Oncol.*, 2001, Vol. 19, No. 2, pp. 376-388, describing a phase III trial of denileukin difitox for the treatment of CTCL, defines CLS (or vascular leak syndrome "VLS" as they call it) as 'the simultaneous occurrence, regardless of severity, of at least two of the following: edema, hypoalbuminemia (2.8 g/dL), and/or hypotension.' By this definition, 25% (18 of 71) of the patients experienced VLS. Olsen et al. 2001 further stated that 'The four patients who experienced a second episode of VLS on rechallenge had albumin levels less than 2.8 g/dL at the start of the course in which the second episode occurred. Serum albumin levels less than 3.0 g/dL seemed to predict and may predispose patients to this syndrome. Preexisting edema was also a risk factor for development of the syndrome.'

Notably, the patients of the T-Guard® Phase 1/2 study had median serum albumin levels of 23 g/L (range 16-34 g/L) at treatment start (i.e. 2.3 g/dL (range 1.6-3.4 g/dL)). This surprisingly shows that T-Guard®, despite being and immunotoxin-based therapy, appears to be suitable for use in a patient subgroup having serum albumin levels below that considered safe for another immunotoxin-based therapy (Ontak®). Without wishing to be bound by any particular theory, the present inventors believe that this advantageously opens up further treatment choice for medical practitioners and their patients.

Additional References Cited in Example 3

Amlot, P. L., M. J. Stone, D. Cunningham, J. Fay, J. Newman, R. Collins, R. May, M. McCarthy, J. Richardson, V. Ghetie and et al. (1993). "A phase I study of an anti-CD22-deglycosylated ricin A chain immunotoxin in the treatment of B-cell lymphomas resistant to conventional therapy." *Blood* 82(9): 2624-2633.

Conry, R. M., M. B. Khazaeli, M. N. Saleh, V. Ghetie, E. S. Vitetta, T. Liu and A. F. LoBuglio (1995). "Phase I trial of an anti-CD19 deglycosylated ricin A chain immunotoxin in non-Hodgkin's lymphoma: effect of an intensive schedule of administration." *J Immunother Emphasis Tumor Immunol* 18(4): 231-241.

Engert, A., V. Diehl, R. Schnell, A. Radszuhn, M. T. Hatwig, S. Drillich, G. Schon, H. Bohlen, H. Tesch, M. L. Hansmann, S. Barth, J. Schindler, V. Ghetie, J. Uhr and E. Vitetta (1997). "A phase-I study of an anti-CD25 ricin A-chain immunotoxin (RFT5-SMPT-dgA) in patients with refractory Hodgkin's lymphoma." *Blood* 89(2): 403-410. Frankel, A. E., J. H. Laver, M. C. Willingham, L. J. Burns, J. H. Kersey and D. A. Vallera (1997). "Therapy of patients with T-cell lymphomas and leukemias using an anti-CD7 monoclonal antibody-ricin A chain immunotoxin." *Leuk Lymphoma* 26(3-4): 287-298.

Messmann, R. A., E. S. Vitetta, D. Headlee, A. M. Senderowicz, W. D. Figg, J. Schindler, D. F. Michiel, S. Creekmore, S. M. Steinberg, D. Kohler, E. S. Jaffe, M. Stetler-Stevenson, H. Chen, V. Ghetie and E. A. Sausville (2000). "A phase I study of combination therapy with immunotoxins IgG-HD37-deglycosylated ricin A chain (dgA) and IgG-RFB4-dgA (Combotox) in patients with refractory CD19(+), CD22(+) B cell lymphoma." *Clin Cancer Res* 6(4): 1302-1313.

Sausville, E. A., D. Headlee, M. Stetler-Stevenson, E. S. Jaffe, D. Solomon, W. D. Figg, J. Herdt, W. C. Kopp, H. Rager, S. M. Steinberg and et al. (1995). "Continuous infusion of the anti-CD22 immunotoxin IgG-RFB4-SMPT-dcA in patients with B-cell lymphoma: a phase I study." *Blood* 85(12): 3457-3465.

Schindler, J., S. Gajavelli, F. Ravandi, Y. Shen, S. Parekh, I. Braunchweig, S. Barta, V. Ghetie, E. Vitetta and A. Verma (2011). "A phase I study of a combination of anti-CD19 and anti-CD22 immunotoxins (Combotox) in adult patients with refractory B-lineage acute lymphoblastic leukaemia." *Br J Haematol* 154(4): 471-476. Schindler, J., E. Sausville, R. Messmann, J. W. Uhr and E. S. Vitetta (2001). "The toxicity of deglycosylated ricin A chain-containing immunotoxins in patients with non-Hodgkin's lymphoma exacerbated by prior radiotherapy: a retrospective analysis of patients in five clinical trials." *Clin Cancer Res* 7(2): 255-258. Schnell, R., P. Borchmann, J. O. Staak, J. Schindler, V. Ghetie, E. S. Vitetta and A. Engert (2003). "Clinical evaluation of ricin A-chain immunotoxins in patients with Hodgkin's lymphoma." *Ann Oncol* 14(5): 729-736.

Schnell, R., O. Staak, P. Borchmann, C. Schwartz, B. Matthey, H. Hansen, J. Schindler, V. Ghetie, E. S. Vitetta, V. Diehl and A. Engert (2002). "A Phase I study with an anti-CD30 ricin A-chain immunotoxin (Ki-4.dgA) in patients with refractory CD30+ Hodgkin's and non-Hodgkin's lymphoma." *Clin Cancer Res* 8(6): 1779-1786. Schnell, R., E. Vitetta, J. Schindler, S. Barth, U. Winkler, P. Borchmann, M. L. Hansmann, V. Diehl, V. Ghetie and A. Engert (199E). "Clinical trials with an anti-CD25 ricin A-chain experimental and immunotoxin (RFT5-SMPT-dgA) in Hodgkin's lymphoma." *Leuk Lymphoma* 30(5-6): 525-537.

Schnell, R., E. Vitetta, J. Schindler, P. Borchmann, S. Barth, V. Ghetie, K. Hell, S. Drillich, V. Diehl and A. Engert (2000). "Treatment of refractory Hodgkin's lymphoma patients with an anti-CD25 ricin A-chain immunotoxin." *Leukemia* 14(1): 129-135. Stone, M. J., E. A. Sausville, J. W. Fay, D. Headlee, R. H. Collins, W. D. Figg, M. Stetler-Stevenson, V. Jain, E. S. Jaffe, D. Solomon, R. M. Lush, A. Senderowicz, V. Ghetie, J. Schindler, J. W. Uhr and E. S. Vitetta (1996). "A phase I study of bolus versus continuous infusion of the anti-CD19 immunotoxin, IgG-HD37-dgA, in patients with B-cell lymphoma." *Blood* 88(4): 1188-1197. Vitetta, E. S. et al. (1991). "Phase I immunotoxin trial in patients with B-cell lymphoma." *Cancer Res* 51(15): 4052-4058.

Example 4—Development of an Improved Immunotoxin Formulation

T-Guard® is being developed for the treatment of GVHD. T-Guard® is a combination product which consists of two antibodies (SPV-T3a and WT1). The monoclonal antibody SPV-T3a is targeted against CD-3 whereas WT-1 targets CD-7 protein. Both are individually coupled to a Ricin Toxin A chain (RTA), which serves as a toxic load upon binding of the target cell. Antibody Drug Conjugates (ADCs) may be formulated as separate infusion concentrates (SPV-T3a-RTA and WT1-RTA) to be mixed just before administration. For example, 4 mL of each formulation (1/1 ratio) may be diluted together in 1 vial up to 100 mL with diluent.

Both antibodies (SPV-T3a and WT1) show physical stability problems in the formulation buffer (13 mM sodium phosphate buffer pH 7.5, 140 mM NaCl and 0.05%, (v/v) Tween-20). This formulation buffer corresponds to a PBS buffer supplemented with Tween-20. SPV-T3a-RTA is stable for 2.5 years at 2-8° C. in that formulation buffer, but shows aggregate formation upon freeze/thaw stress. WT1-RTA is not stable at 5-8° C. in that formulation buffer and is kept stable at −20° C. for 2.5 years. After 3 years of storage the product does not meet the specifications concerning biological activity and particle formation, as detected with DLS.

The present inventors wished to obtain a formulation which would increase the physical stability of both monoclonal antibodies (MAbs) for a longer shelf life.

Methods

Protein Content Analysis

A common application of spectrophotometry is the measurement of light absorption in the UV region of the spectrum, in order to quantify the protein concentration in a sample. Several amino acids usually found in proteins, such as tryptophan and tyrosine, absorb light in the 280 nm range. The absorption of a protein solution depends on the content of the amino acid sequence and the protein concentration. Using the mass extinction coefficient of a protein (s), the concentration in a solution can be calculated from its absorbance (A), according to Lambert-Beer's law:

$A=\varepsilon*c*l$ where:
A=absorbance
$\varepsilon$=mass extinction coefficient in $cm^{-1}*(mg\ L)^{-1}$
c=concentration in mg/mL
l=path length in cm As buffer components and salts may also absorb light at this wavelength, the spectrophotometer should always be blanked with the formulation buffer. The formulation buffer should also be used for the dilution of the sample(s). Measurements are performed on a UV-1800 Spectrophotometer (Shimadzu) using disposable cuvettes.

SDS-PAGE

SDS-PAGE separates proteins in a polyacrylamide matrix according to their electrophoretic mobility. Binding of SDS masks the intrinsic charge of proteins and results in an even distribution of charge to mass units. During gel electrophoresis, SDS-treated proteins will therefore migrate as a function of their approximate size. In addition, existing non-covalent aggregates will dissociate in the presence of SDS.

According to the application, samples can either be run under non-reducing or reducing conditions. Addition of a reducing agent (e.g. dithiothreitol (DTT)) causes the disruption of internal disulphide bonds in the protein and can be used to discriminate between proteins with an intact protein backbone and nicked proteins held together by these disulfide bridges.

Samples are analyzed on a Novex 4-126 Bis/Tris gel. In case the electrophoresis was performed under reducing conditions, NuPage reducing agent was added to the samples and antioxidant agent (Invitrogen) to the electrophoresis buffer. In order to prevent differences in band height or band broadening, equivalent volumes of the samples were loaded. The electrophoresis was run with MOPS-SDS running buffer. After incubation in the fixation solution, proteins were stained with CBBR250-solution and destained. Gels were scanned using proprietary scanning software (ImageQuant, GE).

SE-UPLC Analysis

SE-UPLC allows determination of the molecular size distribution and the relative amounts of intact, monomeric antibody and potential (protein-related) impurities and variants. The primary goal of SE-UPLC is to detect irreversible soluble protein oligomerization and aggregation as well as smaller protein fragments generated by protein hydrolysis. During the method development a column and mobile phase are selected which give minimal interaction of the protein with the solid phase to prevent "sticking" of the protein or its multimeric forms to the column while at the same time giving a good recovery. The components should be separated solely by their MW. Proteins are detected by UV absorbance at 280 nm and the relative amount of a specific protein impurity (expressed as relative surface area (5) is calculated by dividing the surface area of its peak by the total surface area.

Experiments are performed on an UPLC H-Class bio instrument (Waters) with a detection at 220 nm or 280 nm. The system is equipped with a bio-inert flow path a stainless steel, specifically for biomolecules.

Particle Size Analysis (DLS)

When a beam of light passes through a colloidal dispersion, the particles or droplets scatter some of the light in all directions. When the particles are very small compared with the wavelength of the light, the intensity of the scattered light is uniform in all directions (Rayleigh scattering); for larger particles (above approximately 250 nm diameter), the intensity is angle dependent (Mie scattering).

Using coherent laser light it is possible to observe time-dependent fluctuations in the scattered intensity using a photomultiplier detector. These fluctuations arise from the fact that the particles are small enough to undergo random thermal (Brownian) motion and the distance between them is therefore constantly varying. Analysis of the time dependence of the intensity fluctuation can therefore yield the diffusion coefficient of the particles from which, via the Stokes Einstein equation, knowing the viscosity of the medium, the hydrodynamic radius or diameter of the particles can be calculated.

DLS measurements were performed on a Zetasizer NanoZS (Malvern) in disposable low volume UVCuvettes (PlastiBrand). Typical measurements were performed in 70 µL at 25° C. where the sample was equilibrated to the temperature during 3 minutes prior to the actual measurement. Measurement duration and laser intensity was chosen automatically by the instrument based on the scattering signal of the sample. All measurements were analysed using the Zetasiser Software (version 7.02).

Buffer Exchange

To allow a fast screening of multiple buffers the buffer exchange was performed with 2 mL Zeba Spin Desalting columns (MWCC=7 kDa, Pierce). These columns contain a size exclusion resin and can be used for diluted or concentrated samples, allowing a good protein recovery. The columns were always used with sample sizes of 700 µL material.

PEG Screening

A PEG-6000 based screen was used to perform a primary formulation screen. Since it is known that the ADC's are susceptible to aggregation, solubility is one of the major stability parameters. The buffer type and pH will influence the solubility and therefore 12 different buffers were prepared to screen for an optimal solubility of the MAb's.

The conditions tested were:
Histidine buffer pH 5.5, 6.0 and 6.5
Phosphate buffer pH 7.0, 7.5 and 7.5
Citrate buffer pH 5.5, 6.0 and 6.5
Acetate buffer pH 4.0, 4.5 and 5.0
D-PBS (as reference)

50 mM solutions were prepared from each buffer as well as buffer solutions containing 40% (w/v) PEG-6000. The latter was made by weighing 12 g PEG-6000 and adding concentrated buffer solutions and MQ water up to 30 mL in order to obtain a 50 mM solution with 40% (w/v) PEG-6000. The stock solution was diluted further with buffer or protein to a final concentration of 4-20% (w/v) PEG-6000.

The original material was concentrated using a concentrator (Amicon ultra 15, 10 kDa MWCO) to approximately concentration of 0.40 mg/mL. Concentrations are determined using UV absorbance measurements. The material was diluted 2-fold in the plate in a total volume of 100 μL and after 1 day incubation at 5'C the plate was measured. The readout was performed on a Envision (Perkin Elmer) with an OD filter of 405 nm.

Summary of Results

Out of the different experiments the following overviews (Table 2 and Table 3) are made, giving an overview of the different experiments. Both overviews show a preference for a citrate buffer pH 6.5 as compared to a phosphate buffer pH 7.5. Phosphate buffers Give rise to more aggregation events as compared to citrate buffers. This is confirmed by SE-UPLC, SDS-PAGE and DLS. Differences for the excipients are observed for the citrate buffers. In this case, a higher recovery and better stability is seen for arginine as excipient. This excipient showed resistance to freeze/thaw stress and a lower amount of high molecular weight (HMW) variants at temperatures up to 25° C. At 40° C. there was also a high amount of aggregates observed. The same conclusion could be made for both antibodies and confirmation of the results was obtained by SDS-PAGE.

The formulation that was selected on the basis of the above results for WT1-RTA and SPV-T3a-RTA was: 10 mM citrate (pH 6.5), 155 mM L-Arginine.HCl and 0.05% (w/v) Tween-20. The recipe for this formulation is as follows:

Component Amount
Citric acid*0.11 g
Sodium Citrate*2.79 g
L-Arginine.HCl 32.70 g
Tween-20 0.5 g
H$_2$O Add up to 1000 mL
*correct pH to 6.5 using NaOH solution Example 5—Development of a Still-Further Improved Immunotoxin Formulation The present inventors sought to improve the stability of the T-Guard® formulation still further. In the above-mentioned formulation (10 mM citrate (pH 6.5), 155 mM L-Arginine.HCl and 0.05 (w/v) Tween-20), both SPV-T3a-RTA and WT1-RTA were found to be stable at −60° C., −20° C. and 5° C. for up to 9 months. However, stability at 25° C. was found to be sub-optimal owing to the formation of aggregates. The aim of presently-described study was to develop a more stable formulation based on accelerated stability studies.

Heat Stress Study

To characterize both compounds (WT1-RTA and SPV-T3a-RTA), 6 different analysis techniques were used:
SEC
SDS-PAGE
Aggregation point
DLS
pH
Osmolality

TABLE 2

|  |  | F/T | | | Stab 5° C. | | Stab 25° C. | | Stab 40° C. | |
|  |  | HMW | Agg | DLS | HMW | Agg | HMW | Agg | HMW | Agg |
| --- | --- | --- | --- | --- | --- | --- | --- | --- | --- | --- |
| Phosphate | Sucrose | ++ | − | − | − | ++ | − | ++ | − | + |
|  | Arginine | ++ | ++ | ++ | ++ | ++ | − | ++ | − | ++ |
|  | Mannitol | ++ | + | ++ | ++ | ++ | − | + | − | + |
|  | Trehalose | ++ | − | ++ | ++ | + | + | + | − | + |
|  | NaCl | ++ | + | − | ++ | ++ | − | ++ | − | ++ |
| Citrate | Sucrose | ++ | ++ | ++ | ++ | + | ++ | + | + | + |
|  | Arginine | ++ | ++ | ++ | ++ | ++ | ++ | ++ | − | ++ |
|  | Mannitol | ++ | ++ | ++ | ++ | + | ++ | + | + | + |
|  | trehalose | ++ | ++ | ++ | ++ | + | ++ | + | + | + | overview of the different results for WT1-RTA from the freeze/thaw analysis and short term storage study. The different buffers (phosphate and citrate) as well as the excipients are given and results are evaluated as good (++), intermediate (+) or not preferred (−). The SE-UPLC results are given as HMW and agg (area under the curve). "F/T" = freeze/thaw; "Stab" = stability; "HMW" = high molecular weight variants; "Agg" = aggregates.

TABLE 3

|  |  | F/T | | | Stab 5° C. | | Stab 25° C. | | Stab 40° C. | |
|  |  | HMW | Agg | DLS | HMW | Agg | HMW | Agg | HMW | Agg |
| --- | --- | --- | --- | --- | --- | --- | --- | --- | --- | --- |
| Phosphate | Sucrose | − | ++ | ++ | − | ++ | − | ++ | − | + |
|  | Arginine | ++ | ++ | − | ++ | ++ | − | ++ | − | ++ |
|  | Mannitol | ++ | ++ | ++ | ++ | ++ | − | + | − | + |
|  | Trehalose | ++ | ++ | ++ | ++ | + | + | + | − | + |
|  | NaCl | − | ++ | − | ++ | ++ | − | ++ | − | ++ |
| Citrate | Sucrose | ++ | ++ | ++ | ++ | + | ++ | + | + | + |
|  | Arginine | ++ | ++ | − | ++ | ++ | ++ | ++ | − | ++ |
|  | Mannitol | ++ | ++ | ++ | ++ | + | ++ | + | + | + |
|  | trehalose | ++ | ++ | ++ | ++ | + | ++ | + | + | + | overview of the different results for SPV-T3a-RTA from the freeze/thaw analysis and short term storage study. The different buffers (phosphate and citrate) as well as the excipients are given and results are evaluated as good (++), intermediate (+) or not preferred (−). The SE-UPLC results are given as HMW and agg (area under the curve). "F/T" = freeze/thaw; "Stab" = stability; "HMW" = high molecular weight variants; "Agg" = aggregates.

TABLE 4

Overview of heat stress study

| Sample | Temperature | Time point |
|---|---|---|
| SPV-T3a-RTA | 5° C. | T = 0 |
| | 40° C. | T = 2 days |
| | 40° C. | T = 4 days |
| WT1-RTA | 5° C. | T = 0 |
| | 40° C. | T = 2 days |
| | 40° C. | T = 4 days |

Since no information was available on the aggregation mechanism of the antibodies, a broad range of excipients were taken into account for the screening: reducing agents, solubilizing agents, antioxidants, amino acids and sugars.

The effect of each combination of excipients is summarised below for each antibody.

TABLE 5

Effect of the excipients on SPV-T3a-RTA

| Agent | Effect |
|---|---|
| 10 mM citrate; 150 mM L-arginine; 0.05% Tween 20; 0.2 mM N-Acetylcysteine | − |
| 10 mM citrate; 150 mM L-arginine; 0.05% Tween 20; 0.5 mg/ml poly (ethyleneimine) | − |
| 10 mM citrate; 150 mM L-arginine; 0.05% Tween 20; 0.5 mg/ml poly (ethyleneimine); 0.25 mg/ml EDTA disodium salt | − |
| 10 mM citrate; 150 mM L-arginine; 0.05% Tween 20; 0.5 mg/ml poly (ethyleneimine); 10 mM sodium benzoate | = |
| 10 mM citrate; 150 mM L-arginine; 0.05% Tween 20; 0.2 mM monothioglycerol | − |
| 10 mM citrate; 150 mM L-arginine; 0.05% Tween 20; 0.25 mg/ml vitamin E TPGS | − |
| 10 mM citrate; 150 mM L-arginine; 0.05% Tween 20; 1 mM 2-2'-dithiodipyridine | − − |
| 10 mM citrate; 100 mM L-arginine; 0.05% Tween 20; 0.5% Glycerin | − |
| 10 mM citrate; 50 mM L-arginine; 0.05% Tween 20 | − |
| 10 mM citrate; 150 mM L-arginine; 0.05% Tween 20; 12 mM glutamate | + |
| 10 mM citrate; 150 mM L-arginine; 0.05% Tween 20; 50 mM glycine | + |
| 10 mM citrate; 150 mM L-arginine; 0.05% Tween 20; 1 mM methionine | − |
| 10 mM citrate; 150 mM L-arginine; 0.05% Tween 20; 50 mM betaine | − |
| 10 mM citrate; 150 mM L-arginine; 0.05% Tween 20; 20 mM sorbitol | − |
| 10 mM citrate; 150 mM L-arginine; 0.05% Tween 20; 20 mM trehalose | − |

TABLE 6

Effect of the excipients on WT1-RTA

| Agent | Effect |
|---|---|
| 10 mM citrate; 150 mM L-arginine; 0.05% Tween 20; 0.2 mM N-Acetylcysteine | − |
| 10 mM citrate; 150 mM L-arginine; 0.05% Tween 20; 0.5 mg/ml poly (ethyleneimine) | − |
| 10 mM citrate; 150 mM L-arginine; 0.05% Tween 20; 0.5 mg/ml poly (ethyleneimine); 0.25 mg/ml EDTA disodium salt | − |
| 10 mM citrate; 150 mM L-arginine; 0.05% Tween 20; 0.5 mg/ml poly (ethyleneimine); 10 mM sodium benzoate | − |
| 10 mM citrate; 150 mM L-arginine; 0.05% Tween 20; 0.2 mM monothioglycerol | − |
| 10 mM citrate; 150 mM L-arginine; 0.05% Tween 20; 0.25 mg/ml vitamin E TPGS | − |
| 10 mM citrate; 150 mM L-arginine; 0.05% Tween 20; 1 mM 2-2'-dithiodipyridine | − − |
| 10 mM citrate; 100 mM L-arginine; 0.05% Tween 20; 0.5% Glycerin | − |
| 10 mM citrate; 50 mM L-arginine; 0.05% Tween 20 | − |
| 10 mM citrate; 150 mM L-arginine; 0.05% Tween 20; 12 mM glutamate | − |
| 10 mM citrate; 150 mM L-arginine; 0.05% Tween 20; 50 mM glycine | + |
| 10 mM citrate; 150 mM L-arginine; 0.05% Tween 20; 1 mM methionine | − |
| 10 mM citrate; 150 mM L-arginine; 0.05% Tween 20; 50 mM betaine | − |
| 10 mM citrate; 150 mM L-arginine; 0.05% Tween 20; 20 mM sorbitol | + |
| 10 mM citrate; 150 mM L-arginine; 0.05% Tween 20; 20 mM trehalose | + |

Addition of 12 mM glutamate and 50 mM glycine have a positive effect on the stability of SPV-T3aRTA, while addition of 50 mM glycine, 20 mM sorbitol and 20 mM trehalose have a positive effect on the stability of WT1-RTA.

A new formulation study was carried out in order to:
confirm the positive effect observed with glycine, sorbitol and trehalose
test additional combinations of the existent excipients (e.g. higher glycine concentration)
new excipients (e.g. other sugars)

The target for osmolality of the formulation buffers was between 300 and 450 mOsm/kg.

Accordingly, an additional excipient screen was set-up with formulation buffers which had a positive effect on both compounds in the above-described study, new combinations with the tested excipients, formulation buffers with higher concentrations of the excipients and formulation buffers with other sugars.

Accelerated stability testing was carried out according to the following overview.

TABLE 7

Overview of accelerated stability study

| Incubation temperature | Time point 2 days | Time point 2 months |
|---|---|---|
| −20° C. | 5° C. | T = 0 |
| 5° C. | 40° C. | T = 2 days |
| 25° C. | 40° C. | T = 4 days |
| 37° C. | 5° C. | T = 0 |

TABLE 8

Effect of the excipients on the stability of SPV-T3a-RTA

| Agent | Effect |
|---|---|
| 10 mM citrate; 150 mM L-arginine; 0.05% Tween 20; 50 mM glycine | = |
| 10 mM citrate; 150 mM L-arginine; 0.05% Tween 20; 12 mM glutamate | = |
| 10 mM citrate; 150 mM L-arginine; 0.05% Tween 20; 75 mM glycine, 50 mM glutamate | + |
| 10 mM citrate; 150 mM L-arginine; 0.05% Tween 20; 100 mM glycine | + |

TABLE 8-continued

| Effect of the excipients on the stability of SPV-T3a-RTA | |
|---|---|
| Agent | Effect |
| 10 mM citrate; 150 mM L-arginine; 0.05% Tween 20; 50 mM glycine; 50 mM sorbitol | + |
| 10 mM citrate; 125 mM L-arginine; 0.05% Tween 20; 125 mM trehalose; 50 mM glycine | + + |
| 10 mM citrate; 125 mM L-arginine; 0.05% Tween 20; 125 mM maltose; 50 mM glycine | + + |
| 10 mM citrate; 120 mM L-arginine; 0.05% Tween 20; 100 mM mannitol; 50 mM glycine | + + |
| 10 mM citrate; 125 mM L-arginine; 0.05% Tween 20; 140 mM maltose | + + |
| 10 mM citrate; 125 mM L-arginine; 0.05% Tween 20; 40 mM maltose; 100 mM glycine | − − |

TABLE 9

| Effect of the excipients on the stability of WT1-RTA | |
|---|---|
| Agent | Effect |
| 10 mM citrate.; 150 mM L-arginine; 0.05% Tween 20; 50 mM glycine | + |
| 10 mM citrate; 150 mM L-arginine; 0.05% Tween 20; 100 mM glycine | + + |
| 10 mM citrate; 150 mM L-arginine; 0.05% Tween 20; 50 mM glycine; 50 mM sorbitol | + |
| 10 mM citrate; 125 mM L-arginine; 0.05% Tween 20; 125 mM trehalose; 50 mM glycine | + + |
| 10 mM citrate; 125 mM L-arginine; 0.05% Tween 20; 125 mM maltose; 50 mM glycine | + + |
| 10 mM citrate; 120 mM L-arginine; 0.05% Tween 20; 100 mM mannitol; 50 mM glycine | ++ |
| 10 mM citrate; 125 mM L-arginine; 0.05% Tween 20; 140 mM maltose | + + |
| 10 mM citrate; 125 mM L-arginine; 0.05% Tween 20; 40 mM maltose; 100 mM glycine | − − |

4 of the tested formulations have a positive effect on the stability of both compounds (SPV-T3a-RTA and WT1-RTA):

1. 10 mM citrate, 125 mM L-arginine; 0.05% Tween 20; 125 mM trehalose; 50 mM glycine
2. 10 mM citrate; 125 mM L-arginine; 0.05% Tween 20; 125 mM maltose; 50 mM glycine
3. 10 mM citrate; 120 mM L-arginine; 0.05% Tween 20; 100 mM mannitol; 50 mM glycine
4. 10 mM citrate; 125 mM L-arginine; 0.05% Tween 20; 140 mM maltose Further stability testing was then carried out on the following formulation: 10 mM citrate; 125 mM L-arginine; 0.05% Tween 20; 140 mM maltose (adjusted to pH 6.5 with 37% HCl).

2 days incubation at 40° C. in the new formulation buffer resulted in approximately 23% more SPV-T3a-RTA monomer and approximately 13% more WT1-RTA monomer compared to incubations in the previous formulation buffer. Also a decrease of insoluble aggregates was observed (see Tables 10 and 11).

TABLE 10

WT1-RTA protein distribution after 2 days at 40° C. in the previous and new formulation buffer

| Formulation | Monomer (%) | Soluble aggregates (%) | Insoluble aggregates (%) |
|---|---|---|---|
| 10 mM citrate, 150 mM L-Arg•HCl, 0.05% (w/v) Tween-20 (pH 6.5) | 61.5 | 24.9 | 13.7 |
| 10 mM citrate, 125 mM L-Arg•HCl, 0.05% (w/v) Tween-20, 140 mM Maltose (pH 6.5) | 74.0 | 22.9 | 3.1 |

TABLE 11

SPV-T3a-RTA protein distribution after 2 days at 40° C. in the previous and new formulation buffer

| Formulation | Monomer (%) | Soluble aggregates (%) | Insoluble aggregates (%) |
|---|---|---|---|
| 10 mM citrate, 150 mM L-Arg•HCl, 0.05% (w/v) Tween-20 (pH 6.5) | 44.9 | 15.9 | 39.1 |
| 10 mM citrate, 125 mM L-Arg•HCl, 0.05% (w/v) Tween-20, 140 mM Maltose (pH 6.5) | 67.9 | 28.1 | 4.0 |

The aggregation point analysis showed that SPV-T3a-RTA (Tagg=51° C.) and WT1-RTA (Tagg=52° C.) are more stable in the new formulation buffer compared to the previous formulation buffer (Tagg=42° C. and 15° C. for SPV-T3a-RTA and WT1-RTA, respectively).

Example 6—Modification of the Monoclonal Antibody-RTA Conjugation Process

The above-described studies (Examples 4 and 5) resulted in a formulation that supports a very good stability profile of both conjugates. Consequently, development work continued to explore how far upstream this preferred formulation buffer could be used in the production and purification process.

The inventors aimed to reduce precipitation and resulting product loss. Yield of the Blue Sepharose column step (removal of unconjugated free antibody) is poor and the fraction that is recovered suffers from aggregation. A substantial fraction precipitates on the column and is lost.

The inventors also aimed to refine loading and elution conditions for Blue Sepharose affinity chromatography to achieve robust, complete separation of mAb and mAb-RTA conjugate.

Finally, the inventors sought to employ the favorable formulation buffer further upstream, up to and including the conjugation step, to prevent precipitation in this earlier phase too.

The change in the production process is depicted in FIGS. 9 and 10. FIG. 9 shows process A, in which the conjugation and purification steps above the central horizontal line are performed in the 25 mM phosphate buffer at pH 7.5; steps below the horizontal line are performed in the 10 mM citrate buffer at pH 6.5. FIG. 10 shows process B, which differs from process A in that the change to the 10 mM citrate buffer occurs further upstream at the point shown by the upper horizontal line. Steps below that upper horizontal line are performed in the 10 mM citrate buffer at pH 6.5.

Upon changing to process B, it was found that:

The antibody conjugation reaction is robust and is compatible with the formulation buffer (10 mM citrate, 125 mM L-Arg.HCl, 0.05% (w Tween-20, 140 mM Maltose (pH 6.5)).

Implementation is simple by changing running buffer on G25

Blue Sepharose binding can be subtly altered by changing L-Arginine concentration. Elution can be achieved by increasing the L-arginine concentration.

In 125 mM L-Arginine no non-conjugated mAb binds, only minor portion of mAb-$RTA_1$ is unbound in flow-through. Optimal selective conditions for equilibration, binding and washing can be determined within the range of 75-125 mM, such as 100-125 mM, L-Arginine.

Elution steps show that mAb-$RTA_1$, mAb-$RTA_2$ and mAb-$RTA_3$ could be separated. Binding becomes stronger with higher degree of conjugation.

Process B is amenable to optimization to balance yield and purity. Also drug-antibody variants could be selectively enriched.

The elution pool after Blue Sepharose was found to have reduced turbidity or precipitation.

Example 7—Phase I/II Trial of a Combination of Anti-CD3/CD7 Immunotoxins for Steroid-Refractory Acute Graft-Versus-Host Disease

Introduction

Acute graft-versus-host disease (aGvHD) is a major complication that can occur following allogenic hematopoietic stem cell transplantation (HSCT). The prognosis among patients who develop aGvHD is poor, particularly in cases of severe steroid-refractory aGvHD (SR-aGvHD) with gastrointestinal (GI) and/or liver involvement.[1,2] At present, no standard second-line therapy is approved for SR-aGvHD, and none of the available treatment options seems to provide convincingly superior results with on average only 30% complete responders.[1, 3, 4] Six-month survival approximates 50%, but long-term survival is achieved in 1 out of 5 patients.[2]

The underlying core of a graft-versus-host immune reaction is the proliferation and differentiation of alloreactive donor T-cells in response to the host's antigen-presenting cells, which induce tissue damage and the propagation of inflammation during the effector phase.[5-7] Therefore, many of the currently used therapies consist of antibodies that cause the depletion of T-cells or either biologicals or small molecule inhibitors designed to suppress T-cell function.[1,3,6,8] The obvious challenge of such approaches is that the induced immunosuppression should be as selective and as brief as possible, to avoid infectious complications and relapse of the underlying hematological malignancy, which could otherwise counterbalance the immediate benefit of controlling the acute GvHD reaction.[9-12]

As a novel approach to achieve this goal, we developed a combination of two anti-T-cell immunotoxins designed to induce a synergistic in-vivo depletion and suppression of T-cells while allowing for a rapid post-treatment reconstitution of the immune system.[13,14] This combination product consists of a 1:1 mixture of two murine monoclonal antibodies against CD3 and CD7, each of which is separately conjugated to a recombinant ricin toxin A chain[15] (I-Guard™), hereafter abbreviated as CD3/CD7-IT).[16,17] Preclinical studies showed that CD3/CD7-IT induces apoptosis of both T-cells—particularly activated T- and NK-cells by inhibiting protein synthesis, and reduces T-cell activation by blocking and modulation of the TCR/CD3 complex (FIG. 12).[17] In a dose-escalation study, 5 out of seven patients with SR-aGvHD, responded to CD3/CD7-IT as third-line therapy.[17] The promising outcome of that study led to the phase I/II study of CD3/CD7-IT for treatment of SR-aGVHD reported here.

Methods

This prospective single arm phase I/II study was approved by the ethics committees and institutional review boards at the Radboud University Medical Center Nijmegen (the Netherlands) and the University Medical Center Muenster (Germany). Informed consent was obtained from all patients.

The 4 mg/$m^2$ T-Guard starting dose of the phase I/II study was selected on basis of the outcome of the dose escalation study.[17] A Bryant-Day 2-stage design was applied[18], with a pre-scheduled interim analysis after 8 patients, to protect patients from unnecessary exposure to an ineffective or toxic treatment. If after the first 8 patients 2 or fewer (≤25%) day 28 responders and/or 4 or more (≥50%) dose limiting toxicities (adverse drug reactions of grade 3 or higher) would be observed (phase I), the trial would have been terminated for futility and/or toxicity. Otherwise, the trial should be extended to a total of 20 patients (phase II) (sample size estimation: S2).

Adult (≥18 years) patients who developed grade II to IV aGvHD following HSCT or following post-transplant donor lymphocyte infusion[19] were eligible for participation; aGvHD grade was defined according to the criteria established by Harris et al.[20] Diagnosis of aGvHD was confirmed with a tissue biopsy. SR-aGvHD was defined as aGvHD that progressed after 3 days or did not improve after 7 days on systemic corticosteroids (≥2 mg/kg/day prednisolone or equivalent).[3, 4] Patients who had already received additional therapeutics for SR-aGvHD were excluded, as were patients with manifestations of moderate or severe chronic GvHD (cGvHD), severe organ dysfunction, uncontrolled infection, serum creatinine levels >266 μmol/L (1.87 mg/dL), and/or serum albumin levels ≤1.5 g/dL.

The treatment schedule of CD3/CD7-IT (S3) consisted of four 4-hour intravenous (i.v.) infusions of 4 mg/m' administered at 48-hour intervals. GvHD prophylaxis, which consisted primarily of cyclosporine-A either alone or in combination with mycophenolate mofetil, was continued during therapy with CD3/CD7-IT. The recommended taper for systemic corticosteroids in patients responding to T-Guard was 10% (of the starting dose) at 3-5 days intervals. After study Day 28, the rate of steroid tapering was left to local protocols. The use of antimicrobial prophylaxis, pre-emptive and/or empirical treatment for infection, and clemastine pretreatment (2 mg i.v.) was left to the discretion of the physician and established local protocols.

Patients were included in the analysis regarding toxicity and efficacy if they received at least one dose of CD3/CD7-IT. The primary endpoints were the overall response rate (ORR, defined as the sum of PR and CR rates) on day 28 and the occurrence of possible drug-related AEs up to 6 months following treatment with CD3/CD7-IT. The secondary endpoints were the day 28 CR rate, 6-month overall survival (OS), and the incidence of cGvHD. ORR, CR on day 28, and 6-month CS were compared to results obtained with our institutions' historical controls who received either inolimomab-etanercept (N=21) or infliximab (N=21).[21] CR was defined as the resolution of all signs and symptoms associated with aGvHD. PR was defined as an improvement in GvHD stage in all initial GvHD target organs, without complete resolution or emergence of GvHD in any new organ. No response (NR) was defined as either no change, a mixed response, progressive disease, or the need for salvage therapy before day 28.[22] The 2014 NIH diagnostic criteria were used to assess and score cGvHD.[23] Hematological and non-hematological AEs, including cytokine release syndrome (CRS), were graded based on the Common Terminology Criteria for AEs (CTCAE 4.0). Capillary leak syndrome (CLS) was graded as follows using the criteria defined earlier[24]: grade 1, asymptomatic, not requiring therapy; grade 2, symptomatic, but not requiring fluid support; grade 3, respiratory compromise or requiring fluids; grade 4, life threatening, requiring vasopressor support and/or mechanical ventilation. In the event of a grade 3 AE, subsequent doses with CD3/CD7-IT were only to be given if the patient's toxicity parameters improved or when judged to be in the patient's interest, at the investigator's discretion. Invasive fungal disease (IFD), EEV- and CMV infection were defined in accordance with established guidelines.[25-27]

Manufacturing of CD3/CD7-IT

CD3/CD7-IT consists of the murine monoclonal antibodies SPV-T3a (anti-CD3) and WT1 (anti-CD7), each of which is conjugated to recombinant RTA. CD3/CD7-IT was manufactured using Good Manufacturing Practices as described previously[15], with the addition of a step to block residual linkers with cysteine and the replacement of deglycosylated plant-derived RTA with recombinant RTA.[17, 28] The immunotoxins were formulated at a concentration of 0.2 mg/ml in an isotonic buffered solution, pH6.5, and stored frozen (at −20° C. or below).

In-Vitro Laboratory Analyses

Peripheral blood samples were collected before and after treatment to analyze predictive GvHD biomarkers, cytokine levels, immune reconstitution, pharmacokinetics, and the development of human anti-drug antibodies (ADRs).

Levels of the biomarkers ST2 (suppression of tumorigenicity 2) and Reg3α (regenerating islet-derived protein 3-alpha) were measured at the Icahn School of Medicine at Mount Sinai, N.Y. A probability score, p^ was determined for each patient based on a validated algorithm[29] used to predict the risk for treatment failure and non-relapse mortality among patients with aGvHD. Patients are at high-risk when the p^ is >0.291 after one week±three days of treatment with systemic corticosteroids.

Serum cytokine levels were measured at Myriad RBM (Austin, Tex.) using quantitative, multiplexed immunoassays.

Lymphocytes were analyzed by immunophenotyping using flow cytometry. Lymphocytes were gated on CD45+ and side scatter low cells and enumeration of helper T-cells (CD5+ and CD4+), cytotoxic T-cells (CD5+ and CD8+), NK cells (CD56+ and CD5−), and B cells (CD19+) was recorded for each phenotype per microliter of blood. CD5 was used instead of CD3 to identify and quantify I-cells because of potential CD3 modulation by the CD3/CD7-IT treatment. For TCR sequencing, DNA was isolated from whole blood collected in PAXgene tubes. The TCRβ CDR3 region was then amplified and sequenced using ImmunoSEQ (Adaptive Biotechnologies, Seattle). Bias-controlled V and J gene primers were used to amplify the rearranged V(D)J segments for high-throughput sequencing (HTS) analysis at approximately 20× coverage.[30] After correcting for sequencing errors using a clustering algorithm CDR3 segments were annotated using the International ImMunoGeneTics information system, thereby identifying which V, D, and J genes contributed to each rearrangement.[31] The absolute numbers of EBV-associated and CMV-associated T-cells were determined by comparing the patients' TCRβ data with TCRβ sequences reported to be specific for EBV and CMV antigens.[37]

The serum concentrations of SPV-T3a-RTA and WT1-RTA, as well as the presence of ADAs against either of these immunotoxins, were measured at Celonic AG (Basel, Switzerland) using validated bioluminescence assays. Pharmacokinetics analyses were performed as described previously.[17]

Statistical Analysis

Patient characteristics were analyzed using descriptive statistics. The estimated aGvHD response rates along with the 95% Clopper-Pearson exact confidence interval (CI) are presented. Toxicity was analyzed by tabulating the incidence of AEs and/or infections with a CTCAE grade≥2. Kaplan-Meier curves were used to analyze overall survival. The Chi-square test was used to compare the ORR and the complete and partial rates of remission on day 28 due to CD3/CD7-IT, with the corresponding results obtained from institutional historical controls who received either inolimomab-etanercept (N=21) or infliximab (N=21).[21] The 6-month OS rate was compared using the log-rank test.

With regards to the immuno-reconstitution within-patient differences were analyzed between the pre-treatment, 1-month, 3-month, and 6-month samples using the Wilcoxon matched-paired signed rank test. A two-sided p-value <0.05 was considered statistically significant. Expanded and enriched T-cell clones were identified using differential abundance analysis as described by DeWitt et al.[33] A given clone was determined to be significantly expanded or contracted in two samples based on its proportion in each repertoire or timepoint and was analyzed using Fisher's exact test with Benjamini-Hochberg correction at the 5% level.

Results

Patient and GvHD Characteristics

Twenty patients were enrolled in the study from June 2014 through September 2016. The patient, donor and GvHD characteristics are presented in Table 1. At the time of enrollment, 3 patients (15%) had grade II aGvHD, and 17 had grade III or IV aGvHD (85%). In 16 patients (80%), two organs were involved; the GI tract and liver were involved in 18 (90%) and 5 (25%) cases, respectively. Baseline albumin levels were low, particularly in the patients with GI-GvHD (median: 2.3 g/dL; range: 1.6-3.4 g/dL; normal range: 3.5-5.0 g/dL). A validated algorithm using serum concentration of ST2 and Reg3α demonstrated significant risk for all patients with a mean p^ of 0.345; the majority of patients (11/20) were classified as high-risk for treatment failure and NRM.[29] Treatment with CD3/CD7-IT was initiated after a median interval of 8 days (range: 5-16 days) after the initial corticosteroid treatment and median 48 days after transplantation (range: 26-308 days).

GvHD Response and Patient Outcome

Figure 13:
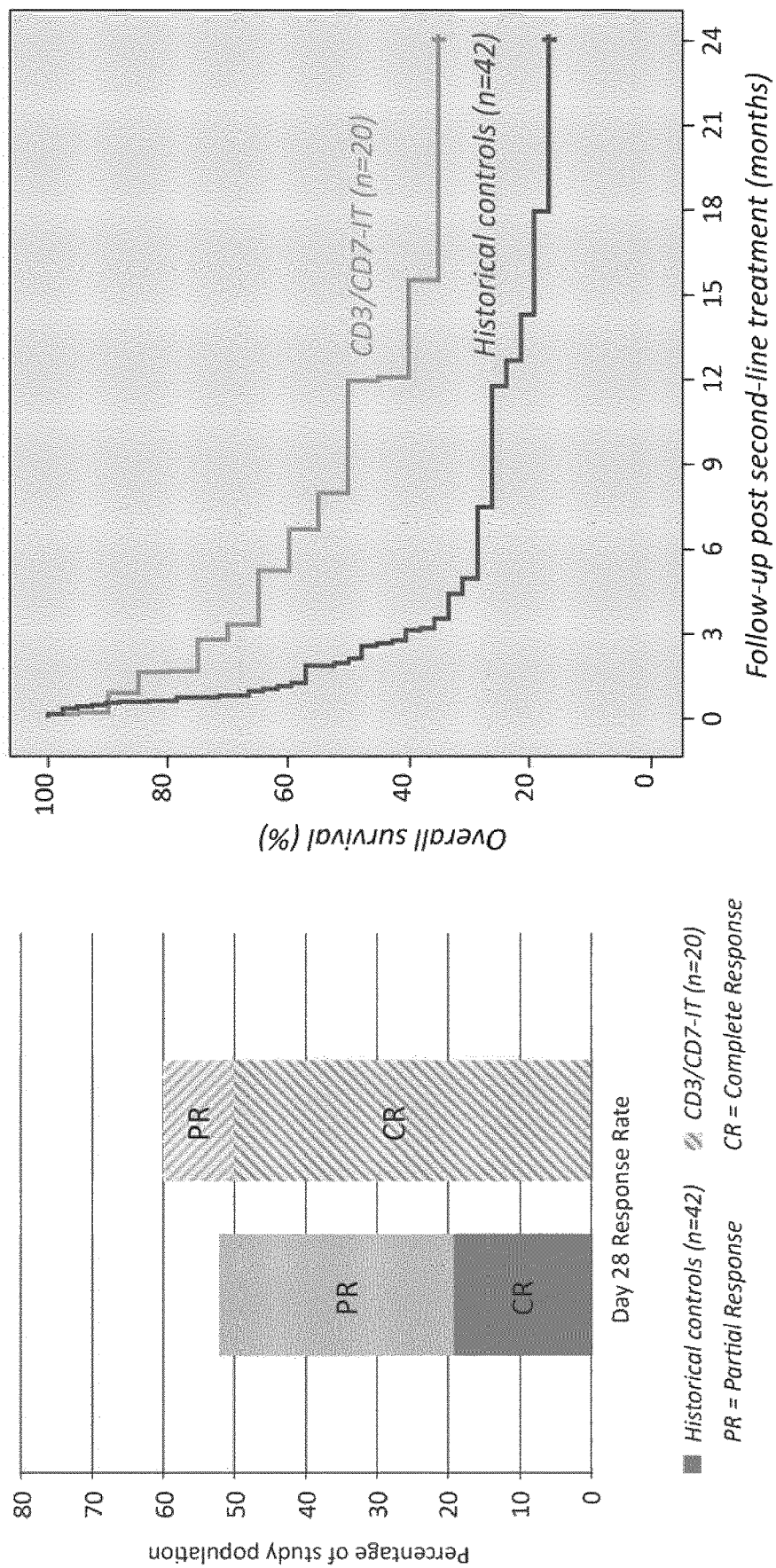
FIG. 13 Overview of the response rate at day 28 (top) and overall survival 6 months after treatment with CD3/CD7-IT (bottom) compared to historical controls. The difference between patients who received CD3/CD7-IT and the his- FIG. 14 CD3/CD7-IT induces rapid immune reconstitution with a diverse T-cell repertoire. (A-C) Time course of the median T-cell count (A), median NK-cell count (B), and median B-cell count (C) for all patients. In each plot, the blue line represents the median value, and the lower and upper gray dotted lines represent the $25^{th}$ and $75^{th}$ percentiles, respectively. (D) Summary of the absolute number of unique T-cell clones prior to administration of CD3/CD7-IT (Pre) and 1, 3, and 6 months after treatment. The number of unique T-cell clones was measured using the total number of unique CDR3 sequences. The p-values are based on a Wilcoxon matched-paired signed rank test. The significant increase in unique T-cell clones 6 months after CD3/CD7-IT therapy reflects an increase in the diversity of expanded T-cells. (E-H) Representative histograms showing the T-cell repertoires in a single patient pre-therapy (E) and 1 (F), 3 (G), and 6 (H) months after CD3/CD7-IT therapy.

The median follow-up period after therapy with CD3/CD7-IT was 292 days (range: 3-889 days). Two patients died due to progressive SR-aGvHD before completing the treatment schedule. The remaining 18 patients (90%) received all four scheduled doses at 48-hour intervals. On day 28, ORR was 60% (12/20 patients) with a 95% CI of 36-81%; 10 patients (50%; 95% CI:27-73%) achieved a CR (FIG. 13). In the 12 responding and surviving patients corticosteroids could be tapered according to protocol. ORR was 55% (6/11) in patients with a high-risk biomarker profile. At the 6-month time point, 12 patients had survived after response on the CD3/CD7-IT combination, corresponding to an OS rate of 60% (95% CI:36-78%) (FIG. 13); survival was 64% (7/11) for patients with a high-risk biomarker profile. The cause of death for the 8 patients who died during the trial was refractory aGvHD (4 patients), refractory GvHD with infection (3 patients), and pseudomembranous colitis (1 patient). The outcomes achieved with CD3/CD7-IT were favorable compared to the outcomes reported for the cohort of 42 patients that were included immediately adjacent to the start of the trial. Specifically, the CR rate was 50% versus 19%, respectively (p=0.012), and the 6-month OS rate was 60% versus 29% (p=0.021). No clear differences could be found with regards to baseline characteristics predicting day 28 response or 6-month survival. To compensate for differences in aGVHD severity at treatment start, the above analysis was repeated following adjustment for overall aGVHD grading. After adjustment for aGVHD grade[20], the CR and OS rates remained significant (p=0.032 and 0.034 respectively). At 24-month after treatment start, the study patients still showed an almost doubling in overall survival as compared to this historical control group (from 16.7 to 35%, p=0.47 and 0.09 respectively). Three of the 12 patients (25%) who survived to the 6-month time point developed cGVHD; for two patients the severity was reported to be mild, for one patient severe. Relapse was seen in three patients with AML, but all were patients with an adverse risk AML.

Safety

The Data and Safety Monitoring Board (DSMB) reviewed the pre-planned interim analysis of the first 8 patients, on basis of which they concluded that no major safety concerns had arisen and that the observed risk-benefit balance warranted continuation of the study. In general, CD3/CD7-IT was well tolerated and was found to be safe, with no SUSARs (suspected unexpected serious adverse reactions) or SAEs (serious AEs) related to the study-drug reported. Although no clinically significant infusion-related reactions were recorded, two patients who had not received pre-treatment experienced chills that resolved quickly after clemastine treatment (grade2 AE). Most of the patients had elevated levels of markers of macrophage activation/recruitment (MCP-1 and MIP-1β), and this increase was most prominent after the first infusion; however, only the two aforementioned patients who experienced chills also had an increase in IL-6 levels.[34, 35] The remaining patients had no increase in IL-6, IL-8, IL-10, or IFN-γ concentrations, nor did they develop clinical signs corresponding to CRS.

Several of the 20 patients developed a limited number of possible treatment-related AEs, including hypoalbuminemia, microangiopathy, and/or thrombocytopenia (Tablet). Hypoalbuminemia was present in all 20 patients at baseline (grade 2 or 3 in 80% of patients) and may have worsened in 8 patients due to treatment with CD3/CD7-IT. These 8 patients developed mild peripheral edema, which in all but one case could easily be managed with diuretics. One patient required treatment with an albumin infusion and diuretics for generalized edema and marked weight gain; this patient was therefore classified as having grade 2 CLS. Fifteen patients (75%) had a pre-existing low platelet count (grade 3 or 4 in 25% of cases), and thrombocytopenia either occurred or worsened in 14 patients (70%). Although various other causes may have contributed to the development of thrombocytopenia, the time course is at least suggestive of a possible relationship with CD3/CD7-IT in nine patients. Nevertheless, the thrombocytopenia was transient, did not result in a bleeding event, and rarely required platelet transfusion. Early EBV and CMV infections (within 3 months) were observed in 3 patients each (with two patients being positive for both EBV and CMV); however, no EBV or CMV disease occurred. Although only 40% of patients received mold-active antifungal prophylaxis, IFD was not observed in any of the patients. Nevertheless, as expected in this setting, the number of infections and AEs was relatively high. Two patients developed a *Clostridium difficile* infection, which resulted in one death due to pseudomembranous colitis. Moreover, although patients developed bacteremia (with enterococci, staphylococci, or *Klebsiella oxytoca* infection 2, 2, and 1 patient, respectively), this incidence rate (25%) was not higher than reported in historical controls.[21]

After treatment with CD3/CD7-IT, ADAs were detected against SPV-T3a-RTA and/or WT1-RTA in 10 out of 20 patients (50%); in four of these 10 patients, the titers were ≥20,000 at any given point. Nevertheless, no cases of serum sickness were reported. The emergence of ADAs was considered to be of little clinical relevance, as ADAs typically form after 9-10 days, whereas CD3/CD7-IT is currently developed as a one-week treatment option only, and its serum half-life is only 9 hours.

Pharmacokinetics

Pharmacokinetics analysis revealed that the mean serum half-life and $C_{max}$ (and SD) of CD3/CD7-IT were 8.59±3.04 h and 1231±671 µg/L, respectively, which is consistent with previously published data.[17]

Immune Reconstitution and Anti-Viral Immunity

Figure 14:
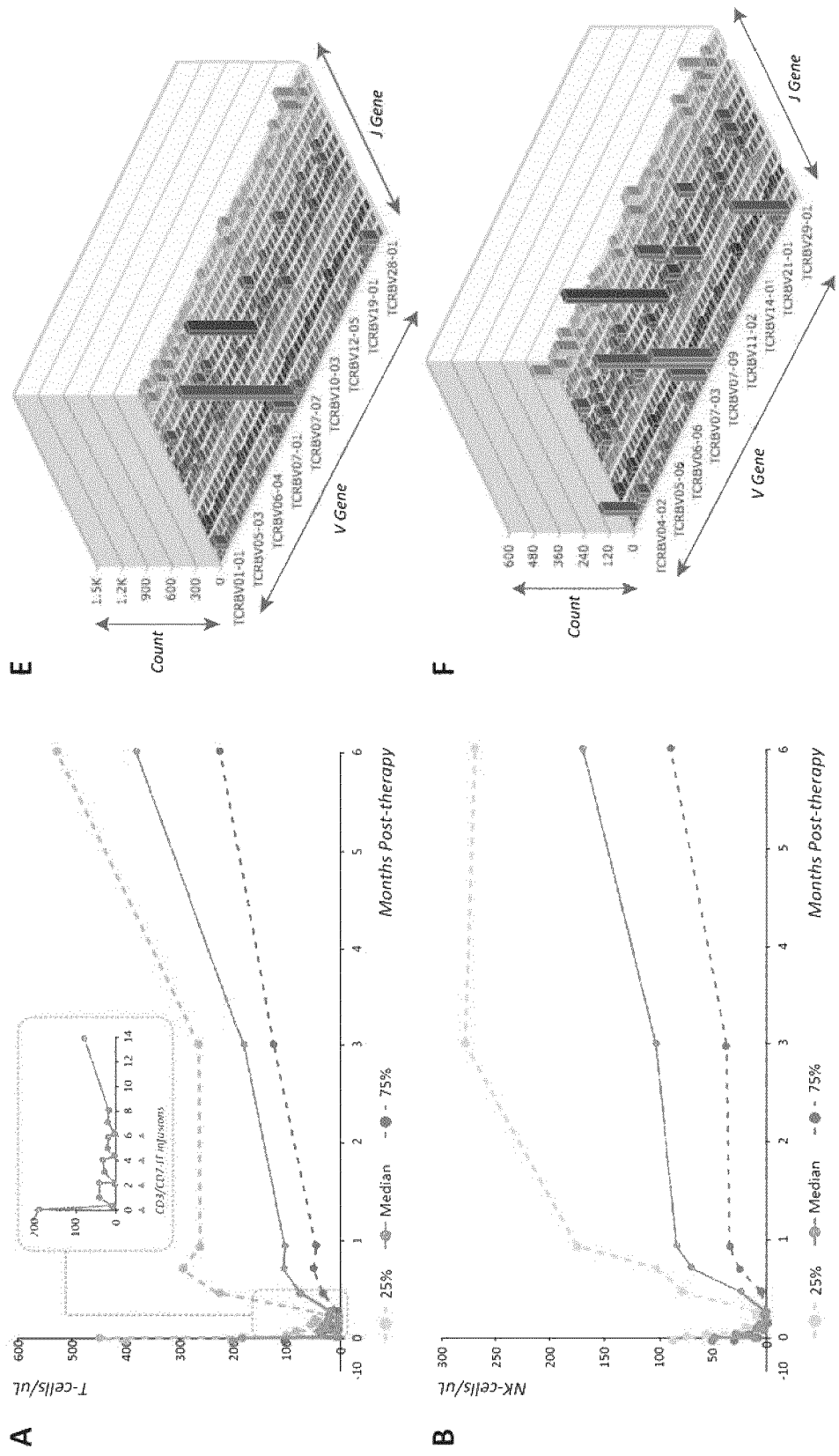
Figure 14:
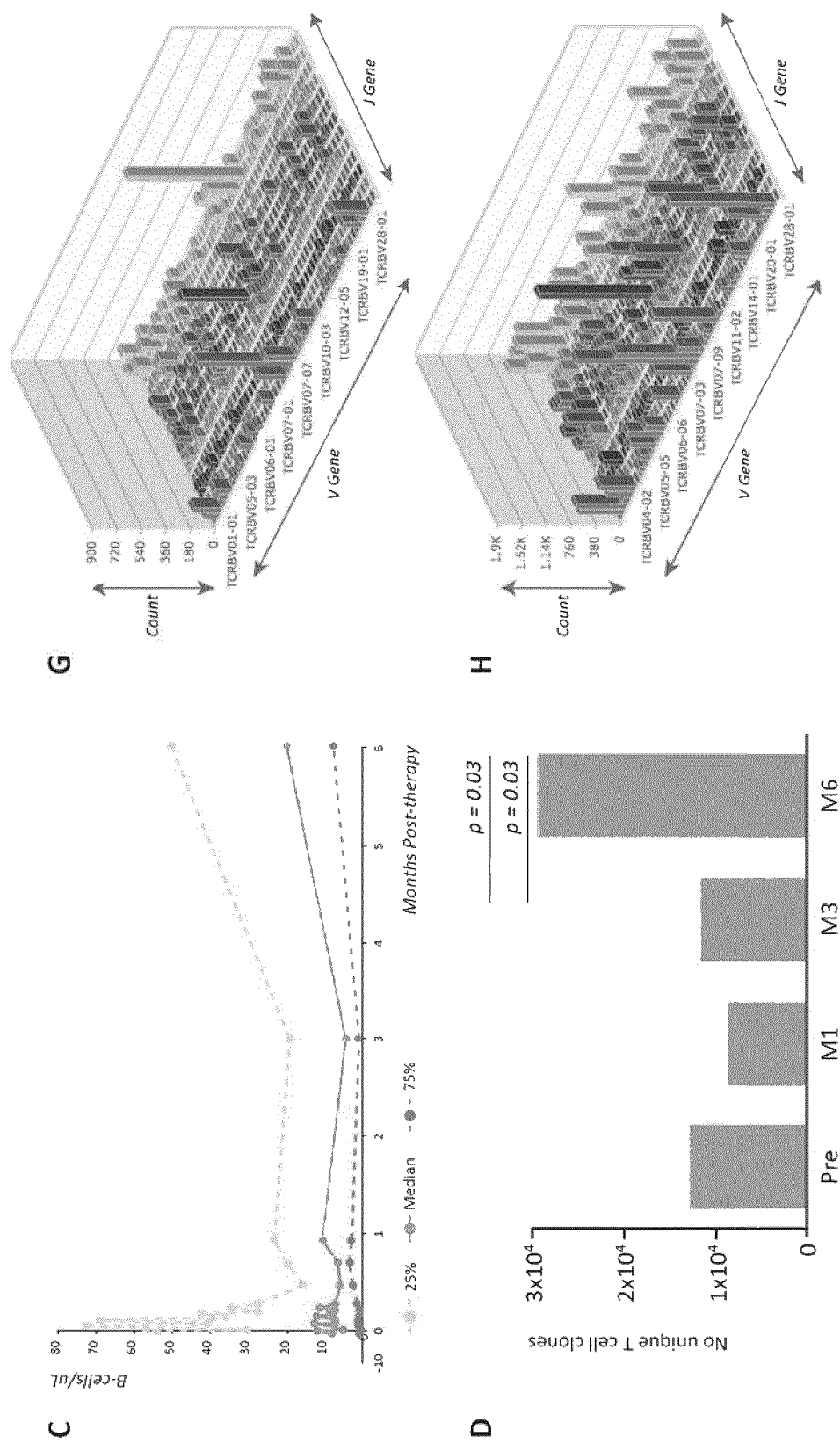

Consistent with its intended effect, treatment with CD3/CD7-IT led to a profound depletion of T-cells and NK-cells, with rapid recovery starting as early as the second week following treatment (FIG. 14A-B). Importantly, no significant effect could be observed on the absolute B cell count (FIG. 14C). No apparent patterns were seen in terms of treatment-induced changes in the relative proportions of naïve, memory, effector and effector memory type of T-cells before and after treatment start (also no decrease or reversal of the CD4:CD8 ratio). In addition, the absolute count of regulatory T cells (Tregs) and the percentage of Tregs in the CD4 population showed normal variation and no obvious upward or downward trends could be observed at 28 days after treatment start or during the rest of the follow up period.

HTS was performed on the CDR3 region of the TCR-β genes in PBMCs before and—when possible—1, 3, and 6 months after treatment with CD3/CD7-IT. HTS can determine the total T-cell count, the diversity of the T-cell repertoire, and the sequences of the TCR CDR3 regions in all T-cells in a given sample. The T-cell diversity in a sample is characterized by the number of unique T-cell clones present in the sample, which is reflected by the number of unique CDR3 sequences identified using HTS. Prior to the start of treatment with CD3/CD7-IT, patients had low T-cell diversity that decreased further by month one, most probably due to a reduction in the absolute number of T-cells. T-cell diversity steadily rebounded by six months post-treatment with a diverse T-cell repertoire that included several new polyclonal T-cell populations (FIG. 14D-H).

Next, we examined whether CD3/CD7-IT affects anti-virus T-cell clones. We therefore analyzed the development of EBV- and/or CMV-specific T-cell clones in patients following treatment with CD3/CD7-IT. Anti-viral T-cell clones were identified by screening for a validated list of 164 and 854 TCRβ sequences encoding receptors that recognize CMV- and EBV-specific antigens, respectively.

Figure 15:
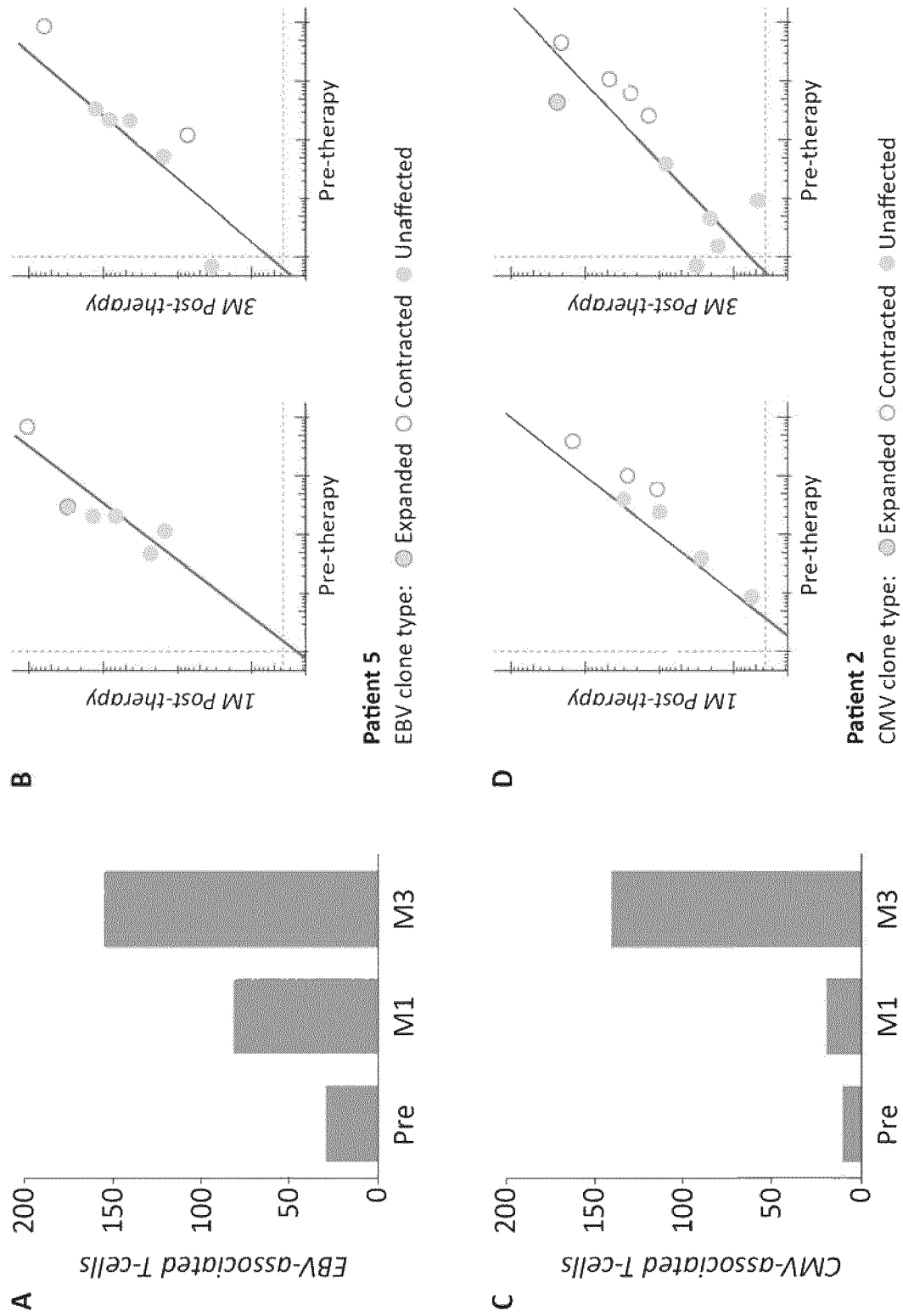
FIG. 15 CD3/CD7-IT does not affect the fraction of anti-virus EBV- and CMV-associated T cell clones. (A&C) Summary of the absolute numbers of anti-EBV (A) and anti-CMV (C) T-cells in patients who tested positive for viral infection after treatment. In each patient group, the number of virus-associated T-cells was measured prior and after treatment. (B&D) Plots showing the differential abundance analysis of unique anti-EBV (B) and anti-CMV (D) T-cell clones. Shown are representative graphs of two patients who tested positive for the respective viral infection prior to treatment. Screening samples were compared to samples taken 1 month and 3 months after therapy with CD3/CD7-IT. This pairwise comparison confirms that the majority of the respective CMV- and EBV-associated clones neither expanded nor contracted as a result of therapy. In each plot, the solid gray diagonal line indicates equal numbers of clones in both samples (no change). Clones positioned between the dotted gray lines and the respective X or Y-axis were not present in other sample, e.g. present pre-therapy but not post therapy.

Patients had positive serology in 95% and 40% and donors in 85% and 35%, for EBV and CMV, respectively. Infections occurred only in those patients with positive serology. FIG. 15A&C show the four patients who experienced an EBV and/or CMV infection after treatment with CD3/CD7-IT (two patients had EBV or CMV infection only and two patients had both EBV&CMV infections). All these patients demonstrated increased numbers of post-infection EBV- and CMV-associated clones, suggesting that the antiviral T-cell response was not negatively affected by treatment with CD3/CD7-IT.

Lastly, we ran a differential analysis of unique antiviral T-cell clones by performing pairwise comparisons between samples taken directly before treatment with CD3/CD7-IT and samples taken 1 and 3 months after treatment in patients who tested positive for a viral infection prior to the start of treatment. This analysis revealed that at the start of treatment, the EBV- and CMV-associated T-cell clones were distributed equally throughout the entire T-cell population in terms of clonal abundance; moreover, these clones did not expand or contract as a result of therapy with CD3/CD7-IT (FIG. 15B-D). Similar results were obtained when we analyzed samples from patients who had anti-viral T-cells at the start of treatment but did not develop a viral infection; our data (not shown) suggest that these patients may have acquired these anti-virus clones from a seropositive donor. Summarized, these results indicate that CD3/CD7-IT does not negatively affect the proportions of anti-EBV or anti-CMV T-cell clones, suggesting that this treatment does not appear to place these patients at a higher risk of acquiring an infection with these opportunistic viruses.

Discussion

Here we report the results of a multicenter phase I/II trial to study the in-vivo safety and efficacy of using CD3/CD7-IT therapy in patients with SR-aGvHD. Our results show that this CD3/CD7-IT has promising efficacy, with an ORR of 60% on day 28; specifically, 50% of our patients achieved a CR, and the 6-month OS rate was 60%. These results were better compared to the outcome reported for our institutional historical controls (FIG. 13) and are notable given the high-risk profile of the patients: 85% with severe SR-aGvHD, 90% GI involvement, and 55% had a high-risk biomarker profile. A pooled analysis of second-line therapies showed that only 32% of patients achieve complete remission with a corresponding 6-month survival rate of 49%.[1] In addition, our phase II results surely match those reported for other drugs currently under investigation for SR-aGVHD, including brentuximab vedotin and ruxolitinib, which have been shown to achieve CR in approximately 30% of patients.[36] Our study has several limitations that require acknowledgment. First, the sample size was relatively small and we did not include a randomized comparator arm. In addition, the study population was heterogeneous with respect to age, conditioning regimen, donor type, and GvHD prophylaxis regimens used. Nonetheless, the study population is representative of patients with SR-aGvHD treated at our institutions and consisted primarily of patients with underlying high-risk features.

CD3/CD7-IT appeared safe. Despite the presence of the anti-CD3 mAb SFV-T3a, CD3/CD7-IT induced a mild infusion reaction in two patients both of whom had not received pre-infusion clemastine. In addition, we observed no toxicity related to CRS or rhabdomyolysis as can be seen with other RTA-based immunotoxins.[37,38] Investigators did consider hypoalbuminemia, microangiopathy, and thrombocytopenia as possibly related to CD3/CD7-IT. However, these events primarily consisted of worsening of pre-existing conditions. Investigators deemed these events more likely related to the underlying SR-GVHD and/or the concomitant use of a calcineurin inhibitor. Nevertheless, given the potential toxic effects of immunotoxins, it remains possible that CD3/CD7-IT may have contributed to these events and attention will need to be paid to this possibility in future studies.

As expected for this clinical setting, infections were relatively common; however, the incidence of infection did not differ substantially from previous reports or from our institutional controls. The multifaceted immune defects due to the presence—and treatment—of GvHD itself, the disruption in the mucosal barrier due to GI-GvHD, and/or dysbiosis can explain the majority of these infections, particularly the *Clostridium difficile* infections and enterococcal bacteremia.[41] Although only half of our patients received mold-active antifungal prophylaxis, we observed no cases of IFD. More importantly, despite the profound depletion of I-cells and NK-cells, the incidence of EBV/CMV infections (15%) appeared to be relatively low,[21,39] and no cases of post-transplant lymphoproliferative disorder or CMV disease occurred in our patients. This may be explained by the fact that virus-specific T-cells were relatively spared by the treatment and by the fact that immune reconstitution occurred within 6 months after starting treatment. In the second week of treatment, the T-cell and NK-cell counts began to rise, particularly in patients who achieved remission of their SR-aGvHD; at 3 months, these cell counts were similar to those normally seen following HSCT.[42] This increase in cell numbers was also accompanied by a simultaneous and significant increase in the diversity of T-cell clones. Thus, therapy with CD3/CD7-IT allows the patient's immune system to recover after remission is achieved, and the immune reconstitution after therapy seems favorable compared to other treatment modalities that rely on in-vivo T-cell depletion (for example anti-thymocyte globulins and alemtuzumab).[42, 44]

Figure 12:
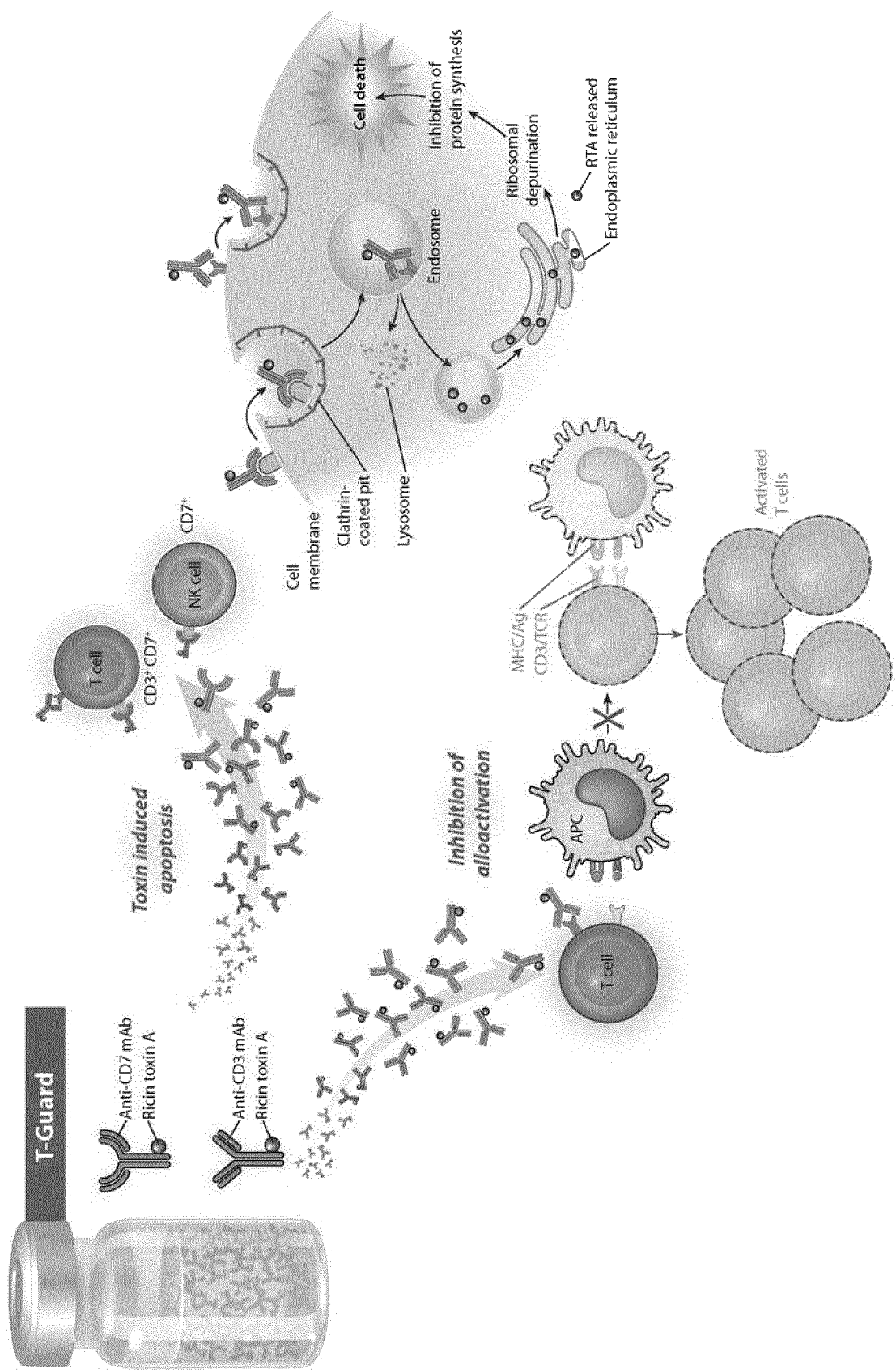
FIG. 12 shows an illustration depicting the possible mechanistic mode of action of immunotoxin combination of the present invention, as exemplified by T-Guard® administration. Both toxin-induced apoptosis (anti-CD3 and anti-CD7 directed) and inhibition of alloactivation are believed to be implicated.

Other immunotoxin-based treatments, such as H65-RTA (anti-CD5, ricin A chain) and denileukin diftitox (CD25, diphtheria toxin), have been clinically evaluated for treating aGvHD.[13,45] CD3/CD7-IT may offer advantages compared to these prior therapies. First, the combination targets multiple antigens on the same target cell, a strategy that tends to be more efficacious than using single immunotoxins.[46-53] In addition, CD3/CD7-IT has a clear preference for recently activated T-cells as well as the NK-cells that may play a role in the efferent phase of aGvHD.[17] Finally, CD3/CD7-IT has a dual mechanism of action in that the anti-CD3 mAb SPV-T3a provides added immunosuppression by binding to the CD3/TCR complex via a mechanism independent of RTA-induced cell killing (FIG. 12)[37].

In summary, we report the results of a phase I/II study involving patients with high-risk SR-aGvHD, showing that CD3/CD7-IT provides a high rate of clinical remissions and rapid immune reconstitution following treatment. Based on these results, a phase III study is currently being designed in order to examine the potential value of including CD3/CD7-IT in the treatment of SR-aGvHD.

TABLE 1

Patients characteristics and HSCT and GvHD features.

|  | N | % |
|---|---|---|
| Characteristics |  |  |
| Number of patients | 20 | 100 |
| Age in years, median | 53 | NA |
| (range) | (18-74) |  |
| Sex, M/F | 9/11 | 45/55 |

TABLE 1-continued

Patients characteristics and HSCT and GvHD features.

| | N | % |
|---|---|---|
| Diagnosis | | |
| Myeloid malignancy | 15 | 75 |
| Lymphoid malignancy | 5 | 25 |
| Donor | | |
| MUD | 13 | 65 |
| MRD | 5 | 25 |
| MMUD | 1 | 5 |
| Haploid | 1 | 5 |
| Stem cell source | | |
| PBSCs | 19 | 95 |
| BM | 1 | 5 |
| Disease risk index | | |
| Low | 0 | 0 |
| Intermediate | 5 | 25 |
| High | 15 | 75 |
| Conditioning regimen[a] | | |
| MAC | 6 | 30 |
| RIC | 5 | 25 |
| NMA | 9 | 45 |
| GvHD prophylaxis | | |
| CyA | 5 | 25 |
| CyA/MTX | 1 | 5 |
| CyA/MMF (post-CyA) | 13 (1) | 65 |
| Acute GvHD | | |
| Post-HSCT | 19 | 95 |
| Post-DLI | 1 | 5 |
| aGvHD grade at enrollment | | |
| II | 3 | 15 |
| III | 11 | 55 |
| IV | 6 | 30 |
| Organ (s) involved | | |
| Skin | 15 | 75 |
| Liver | 5 | 25 |
| Intestinal | 18 | 90 |
| 2 organs involved | 16 | 80 |
| Biomarker score at start of CD3/CD7-IT | | |
| High Risk p > 0.291 | 11 | 55 |
| Time to aGvHD in days median (range) | 40 (10-308) | NA |
| Time to treatment with CD3/CD7-IT in days median (range)[b] | 8 (5-16) | NA |

[a]Conditioning regimen: NMA conditioning consisted of Flu-TBI; RIC regimen were Flu-Bus and Flu-Mel based; MAC regimen were Cyclo-TBI, Flu-Mel-TBI or FLAMSA based.
[b] Relative to the initial corticosteroid treatment.

Notes:
aGvHD = acute graft-versus-host disease; BM = bone marrow; CyA = cyclosporin A; DLI = donor lymphocyte infusion; Haploid = haploidentical related donor; MAC = myeloablative conditioning; MMF = mycophenolate mofetil; MMUD = mismatched unrelated donor; MRD = matched related donor; MTX = methotrexate; MUD = matched unrelated donor; NA = not applicable; NMA = non-myeloablative conditioning; PhAT = Pharmacological Audit Trail; PBSCs = peripheral blood stem cells; RIC = reduced intensity conditioning.
[a]Relative to the initial corticosteroid treatment.

TABLE 2

Summary of adverse events potentially related to treatment.

| Grade 2[a] | Grade 3 | Grade 4 |
|---|---|---|
| Anemia (1)[b] | Thrombocytopenia (3) | Thrombocytopenia (5) |
| Abdominal pain (1) | Neutropenia (1) | |
| Thrombocytopenia (1) | Elevated bilirubin (2) | |
| Neutropenia (1) | Myopathy (1) | |
| Microangiopathy (1) | Microangiopathy (1) | |
| Chills (2) | Hypoalbuminemia (1) | |
| Capillary leak syndrome (1) | | |
| Hypoalbuminemia (1) | | |

[a]Grading of each AE is based on version 4.0 of the Common Terminology Criteria for AEs, with the exception of capillary leak syndrome, which was graded using the system described by Messmann et al.[24]
[b] The numbers in parentheses refer to the number of patients who experienced the indicated adverse event.

References for Example 7

1. Martin P J, Inamoto Y, Flowers M E, Carpenter P A. Secondary treatment of acute graft-versus-host disease: a critical review. *Biol Blood Marrow Transplant.* 2012; 18:982-988.
2. Calmettes C, Vigouroux S, Labopin M, et al. Risk Factors for Steroid-Refractory Acute Graft-versus-Host Disease after Allogeneic Stem Cell Transplantation from Matched Related or Unrelated Donors. *Biol Blood Marrow Transplant.* 2015; 21:860-865.
3. Martin P J, Rizzo J D, Wingard J R, et al. First- and second-line systemic treatment of acute graft-versus-host disease: recommendations of the American Society of Blood and Marrow Transplantation. *Biol Blood Marrow Transplant.* 2012; 18:1150-1163.
4. Deeg H J. How I treat refractory acute GVHD. *Blood.* 2007; 109:4119-4126.
5. Socie G, Blazar B R. Acute graft-versus-host disease: from the bench to the bedside. *Blood.* 2009; 114:4327-4336.
6. Zeiser R, Blazar B R. Acute Graft-versus-Host Disease—Biologic Process, Prevention, and Therapy. *N Engl J Med.* 2017; 377:2167-2179.
7. Holtan S G, Pasquini M, Weisdorf D J. Acute graft-versus-host disease: a bench-to-bedside update. *Blood.* 2014; 124:363-373.
8. Blazar B R, Murphy W J, Abedi M. Advances in graft-versus-host disease biology and therapy. *Nature reviews. Immunology.* 2012; 12:443-458.
9. Meunier M, Bulabois C E, Thiebaut-Bertrand A, et al. Alemtuzumab for severe steroid-refractory gastrointestinal acute craft-versus-host disease. *Biol Blood Marrow Transplant.* 2014; 20:1451-1454.
10. Arai S, Margolis J, Zahurak M, Anders V, Vogelsang G B. Poor outcome in steroid-refractory graft-versus-host disease with antithymocyte globulin treatment. *Biol Blood Marrow Transplant.* 2002; 8:155-160.
11. Martinez C, Solano C, Ferra C, et al. Alemtuzumab as treatment of steroid-refractory acute graft-versus-host disease: results of a phase II study. *Biol Blood Marrow Transplant.* 2009; 15:639-642.
12. Schwartz D M, Kanno Y, Villarino A, Ward M, Gadina M, O'Shea J J. JAK inhibition as a therapeutic strategy for immune and inflammatory diseases. *Nature reviews. Drug discovery.* 2017; 16:843-862.
13. Martin P J, Nelson B J, Appelbaum F R, et al. Evaluation of a CD5-specific immunotoxin for treatment of acute 14. Byers V S, Henslee P J, Kernan N A, et al. Use of an anti-pan T-lymphocyte ricin a chain immunotoxin in steroid-resistant acute craft-versus-host disease. *Blood.* 1990; 75:1426-1432.
15. Schindler J, Gajavelli S, Ravandi F, et al. A phase I study of a combination of anti-CD19 and anti-CD22 immunotoxins (Combotox) in adult patients with refractory B-lineage acute lymphoblastic leukaemia. *Br J Haematol.* 2011; 154:471-476.
16. van Oosterhout Y V, van Emst J L, Bakker H H, et al. Production of anti-CD3 and anti-CD7 ricin A-immunotoxins for a clinical pilot study. *Int J Pharm* 2001; 221:175-186.
17. van Oosterhout Y V, van Emst L, Schattenberg A V, et al. combination of anti-CD3 and anti-CD7 ricin A-immunotoxins for the in vivo treatment of acute graft versus host disease. *Blood.* 2000; 95:3693-3701.
18. Bryant J, Day R. Incorporating toxicity considerations into the design of two-stage phase II clinical trials. *Biometrics.* 1995; 51:1372-13E3.
19. Andersen J T, Daba M B, Berntzen G, Michaelsen T E, Sandlie I. Cross-species binding analyses of mouse and human neonatal Fc receptor show dramatic differences in immunoglobulin G and albumin binding. *J Biol Chem.* 2010; 285:4826-4836.
20. Harris A C, Young R, Devine S, et al. International, Multicenter Standardization of Acute Graft-versus-Host Disease Clinical Data Collection: A Report from the Mount Sinai Acute GVHD International Consortium. *Biol Blood Marrow Transplant.* 2016; 22:4-10.
21. van Groningen L F, Liefferink A M, de Haan A F, et al. Combination Therapy with Inolimomab and Etanercept for Severe Steroid-Refractory Acute Graft-versus-Host Disease. *Biol Blood Marrow Transplant.* 2016; 22:179-182.
22. MacMillan M L, DeFor T E, Weisdorf D J. What predicts high risk acute graft-versus-host disease (GVHD) at onset?: identification of those at highest risk by a novel acute GVHD risk score. *Br J Haematol.* 2012; 157:732-741.
23. Lee S J. Classification systems for chronic graft-versus-host disease. *Blood.* 2017; 129:30-37.
24. Messmann R A, Vitetta E S, Headlee D, et al. A phase I study of combination therapy with immunotoxins IgG-HD37-deglycosylated ricin A chain (dgA) and IgG-RFB4-dgA (Combotox) in patients with refractory CD19 (+), CD22(+) B cell lymphoma. *Clin Cancer Res.* 2000; 6:1302-1313.
25. de Pauw B, Walsh T J, Donnelly J P, et al. Revised definitions of invasive fungal disease from the European Organization for Research and Treatment of Cancer/Invasive Fungal Infections Cooperative Group and the National Institute of Allergy and Infectious Diseases Mycoses Study Group (EORTC/MSG) Consensus Group. *Clin Infect Dis* 2008; 46:1813-1821.
26. Styczynski J, van der Velden W, Fox C P, et al. Management of Epstein-Barr Virus infections and post-transplant lymphoproliferative disorders in patients after allogeneic hematopoietic stem cell transplantation: Sixth European Conference on Infections Leukemia (ECIL-6) guidelines. *Haematologica.* 2016; 101:803-811.
27. Ljungman P, Boeckh M, Hirsch H H, et al. Definitions of Cytomegalovirus Infection and Disease in Transplant Patients for Use in Clinical Trials. *Clin Infect Dis.* 2017; 64:87-91.
28. Chetie V, Swindell E, Uhr J W, Vitetta E S. Purification and properties of immunotoxins containing one vs. two deglycosylated ricin A chains. *J Immunol Methods.* 1993; 166:117-122.
29. Major-Monfried H, Renteria A S, Pawarode A, et al. MAGIC biomarkers predict long-term outcomes for steroid-resistant acute GVHD. *Blood.* 2018; 131:2846-2855.
30. Matos T R, de Rie M A, Teunissen M B M. Research Techniques Made Simple: High-Throughput Sequencing of the T-Cell Receptor. *J Invest Dermatol.* 2017; 137: e131-e138.
31. Lefranc M P. IMGT, the International ImMunoGeneTics Information System. *Cold Spring Harb Protoc.* 2011; 2011:595-603.
32. Emerson R O, DeWitt W S, Vignali M, et al. Immunosequencing identifies signatures of cytomegalovirus exposure history and HLA-mediated effects on the T cell repertoire. *Nature genetics.* 2017; 49:659-665.
33. DeWitt W S, Emerson R O, Lindau P, et al. Dynamics of the cytotoxic T cell response to a model of acute viral infection. *Journal of virology.* 2015; 89:4517-4526.
34. Lee D W, Gardner R, Porter D L, et al. Current concepts in the diagnosis and management of cytokine release syndrome. *Blood.* 2014; 124:188-195.
35. Hay K A, Hanafi L A, Li D, et al. Kinetics and biomarkers of severe cytokine release syndrome after CD19 chimeric antigen receptor-modified T-cell therapy. *Blood.* 2017; 130:2295-2306.
36. Chen Y B, Perales M A, Li S, et al. Phase 1 multicenter trial of brentuximab vedotin for steroid-refractory acute graft-versus-host disease. *Blood.* 2017; 129:3256-3261.
37. Schindler J, Sausville E, Messmann R, Uhr J W, Vitetta E S. The toxicity of deglycosylated ricin A chain-containing immunotoxins in patients with non-Hodgkin's lymphoma is exacerbated by prior radiotherapy: a retrospective analysis of patients in five clinical trials. *Clin Cancer Res.* 2001; 7:255-258.
38. Stone M J, Sausville E A, Fay J W, et al. A phase I study of bolus versus continuous infusion of the anti-CD19 immunotoxin, IgG-HD37-dgA, in patients with B-cell lymphoma. *Blood.* 1996; 88:1188-1197.
39. Socie G, Vigouroux S, Yakoub-Agha I, et al. A phase 3 randomized trial comparing inolimomab vs usual care in steroid-resistant acute GVHD. *Blood.* 2017; 129:643-649.
40. Garcia-Cadenas I, Rivera I, Martino R, et al. Patterns of infection and infection-related mortality in patients with steroid-refractory acute graft versus host disease. *Bone Marrow Transplant.* 2017; 52:107-113.
41. Taur Y, Xavier J B, Lipuma L, et al. Intestinal domination and the risk of bacteremia in patients undergoing allogeneic hematopoietic stem cell transplantation. *Clin Infect Dis.* 2012; 55:905-914.
42. Alho A C, Kim H T, Chammas M J, et al. Unbalanced recovery of regulatory and effector T cells after allogeneic stem cell transplantation contributes to chronic GVHD. *Blood.* 2016; 127:646-657.
43. Mohty M. Mechanisms of action of antithymocyte globulin: T-cell depletion and beyond. *Leukemia.* 2007; 21:1387-1394.
44. Willemsen L, Jol-van der Zijde C M, Admiraal R, et al. Impact of serotherapy on immune reconstitution and survival outcomes after stem cell transplantations in children: thymoglobulin versus alemtuzumab. *Biology of blood and marrow transplantation: journal of the American Society for Blood and Marrow Transplantation.* 2015; 21:473-482.

45. Shaughnessy P J, Bachier C, Grimley M, et al. Denileukin diftitox for the treatment of steroid-resistant acute graft-versus-host disease. *Biol Blood Marrow Transplant.* 2005; 11:188-193.
46. Herrera L, Farah R A, Pellegrini V A, et al. Immunotoxins against CD19 and CD22 are effective in killing precursor-B acute lymphoblastic leukemia cells in vitro. *Leukemia.* 2000; 14:853-858.
47. Preijers F W, Tax W J, Wessels J M, Capel P J, De Witte I, Haanen C. Different susceptibilities of normal T cells and T cell lines to immunotoxins. *Scandinavian journal of immunology.* 1988; 27:533-540.
48. Preijers F W, De Witte T, Rijke-Schilder G P, et al. Human T lymphocyte differentiation antigens as target for immunotoxins or complement-mediated cytotoxicity. *Scandinavian journal of immunology.* 1988; 28:185-194.
49. Derocq J M, Laurent G, Casellas P, et al. Rationale for the selection of ricin A-chain anti-T immunotoxins for mature T cell depletion. *Transplantation.* 1987; 44:763-769.
50. Yu Y H, Crews J R, Cooper K, et al. Use of immunotoxins in combination to inhibit clonogenic growth of human breast carcinoma cells. *Cancer Res.* 1990; 50:3231-3238.
51. Crews J R, Maier L A, Yu Y H, et al. A combination of two immunotoxins exerts synergistic cytotoxic activity against human breast-cancer cell lines. *Int J Cancer.* 1992; 51:772-779.
52. Dean G S, Pusztai L, Xu F J, et al. Cell surface density of p185(c-erbB-2) determines susceptibility to anti-p185 (c-erbB-2)-ricin A chain (RTA) immunotoxin therapy alone and in combination with anti-p170(EGFR)-RTA in ovarian cancer cells. *Clin Cancer Res.* 1998; 4:2545-2550.
53. Engert A, Gottstein C, Bohlen H, et al. Cocktails of ricin A-chain immunotoxins against different antigens on Hodgkin and Sternberg-Reed cells have superior anti-tumor effects against H-RS cells in vitro and solid Hodgkin tumors in mice. Int J Cancer. 1995; 63:304-309.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A pharmaceutical composition comprising:
   (i) a first monoclonal antibody that recognizes CD3 having a heavy chain variable region comprising a complementarity determining region 1 (CDRH1) comprising the amino acid sequence of SEQ ID NO: 5; a complementarity determining region 2 (CDRH2) comprising the amino acid sequence of SEQ ID NO: 6; and a complementarity determining region 3 (CDRH3) comprising the amino acid sequence of SEQ ID NO: 7; and
   a light chain variable region comprising a complementarity determining region 1 (CDRL1) comprising the amino acid sequence of SEQ ID NO: 8; a complementarity determining region 2 (CDRL2) comprising the amino acid sequence of SEQ ID NO: 9, and a complementarity determining region 3 (CDRL3) comprising the amino acid sequence of SEQ ID NO: 10, wherein the first antibody is conjugated to at least one ricin toxin A (RTA), and a second monoclonal antibody that recognizes CD7 having a heavy chain variable region comprising a CDRH1 comprising the amino acid sequence of SEQ ID NO: 15; a CDRH2 comprising the amino acid sequence of SEQ ID NO: 16; and a CDRH3 comprising the amino acid sequence of SEQ ID NO: 17; and a light chain variable region comprising a CDRL1 comprising the amino acid sequence of SEQ ID NO: 18; a CDRL2 comprising the amino acid sequence of SEQ ID NO: 19, and a CDRL3 comprising the amino acid sequence of SEQ ID NO: 20, wherein the second antibody is conjugated to at least one ricin toxin A (RTA);

(ii) 5 to 20 mM of a citrate buffer;
(iii) 50 to 300 mM of L-arginine or a pharmaceutically acceptable salt thereof;
(iv) 0.01 to 0.1% (w/v) of a polysorbate; and
(v) 120 to 160 mM maltose, wherein the composition is in water and has a pH in the range 6 to 7.5.

2. The composition of claim 1, wherein:
the first monoclonal antibody comprises a heavy chain comprising the amino acid sequence of SEQ ID NO: 1 and a light chain comprising the amino acid sequence of SEQ ID NO: 2, wherein the first antibody is conjugated to at least one ricin toxin A (RTA), and the second monoclonal antibody having a heavy chain comprising the amino acid sequence of SEQ ID NO: 11 and a light chain comprising the amino acid sequence of SEQ ID NO: 12, wherein the second antibody is conjugated to at least one ricin toxin A (RTA).

3. The composition of claim 1, further comprising at least one agent selected from:
100 to 150 mM trehalose;
25 to 75 mM glycine; and
80 to 120 mM mannitol.

4. The composition of claim 1, wherein the maltose is 130 to 150 mM maltose monohydrate.

5. The composition of claim 1, comprising 0.05 to 0.5 mg/mL of the first monoclonal antibody and 0.05 to 0.5 mg/mL of the second monoclonal antibody.

6. The composition of claim 1, comprising 0.2 mg/mL of the first monoclonal antibody and 0.2 mg/mL of the second monoclonal antibody.

7. The composition of claim 1, comprising 10 mM sodium citrate/citric acid buffer.

8. The composition of claim 1, comprising 125 mM of L-arginine HCl.

9. The composition of claim 1, comprising 0.05% (w/v) Tween 20.

10. The composition of claim 1, comprising 140 mM maltose monohydrate.

11. The composition of claim 1, wherein the composition is in water for injection and has a pH of 6.5.

12. The composition of claim 1, wherein the ricin toxin A is ricin, deglycosylated ricin A (dgRTA) or non-glycosylated recombinant ricin A.

13. A lyophilised composition that is a freeze-dried form of the composition of claim 1 and which is suitable for reconstitution with water or an aqueous solution.

14. A method of treating acute Graft versus Host disease (aGVHD) in a human subject, wherein the method comprises:
(a) analysing a sample obtained from the subject for viral infection;
(b) administering the composition of claim 1 to the subject when the subject is determined to exhibit elevated or rising Epstein-Barr virus (EBV) or human cytomegalovirus (CMV) viral titre.

15. The method of claim 14, wherein the administering comprises multiple infusions of said composition at a dose of 4 mg/m$^2$ Body Surface Area (BSA).

16. The method of claim 14, wherein the administering comprises four 4-hour infusions given at 48-hour intervals.

17. The method of claim 14, wherein at least one of the following is de-immunised:
the first antibody;
the second antibody;
the toxic moiety of the first antibody; and
the toxic moiety of the second antibody.

18. The method of claim 14, wherein the subject exhibits an EBV or CMV viral titre above 1000 viral DNA copies/ml of blood.

19. The method of claim 14, wherein the composition suppresses or kills CD3+ or CD7+ T-cells.

20. The method of claim 14, wherein the composition spares CD8+ anti-viral T-cells relative to CD3+ or CD7+ T-cells.

21. The method of claim 14, wherein the subject is monitored for viral infection or reactivation by measuring at least one of a viral titre, viral culture, viral antigen detection, viral serology, or immunohistochemistry at least once before administration of said composition.

22. The method of claim 21, wherein said monitoring comprises measuring plasma viral titre by real-time quantitative PCR.

23. The method of claim 14, wherein the subject is being or has been treated with prophylactic antiviral medication.

24. A method of preventing chronic GVHD (cGVHD) in a human subject having acute Graft versus Host disease (aGVHD), comprising the step of administering a therapeutically effective amount of the composition of claim 1.

25. A method of treating acute Graft versus Host disease (aGVHD) in a human subject, wherein the method comprises:
(a) measuring the serum albumin level in a sample obtained from the subject;
(b) administering the composition of claim 1 to the subject when the subject has a serum albumin level of between 10 g/L and 15 g/L.

\* \* \* \* \*

SEQUENCE LISTING

```
<160> NUMBER OF SEQ ID NOS: 20

<210> SEQ ID NO 1
<211> LENGTH: 456
<212> TYPE: PRT
<213> ORGANISM: Artificial Sequence
<220> FEATURE:
<223> OTHER INFORMATION: SPV-T3a Heavy Chain

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Ile Gln Arg Phe
    50                  55                  60

Lys Asp Lys Ala Thr Leu Thr Ala Asp Lys Ser Ser Ser Thr Ala Tyr
65                  70                  75                  80

Met Gln Val Ser Ser Leu Thr Ser Glu Asp Ser Ala Val Tyr Tyr Cys
                85                  90                  95

Ala Arg Gly Ser Arg Tyr Asp Tyr Tyr Gly Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Ser Val His Thr Phe Pro Ala Leu
                165                 170                 175

Leu Gln Ser Gly Leu Tyr Thr Met Ser Ser Ser Val Thr Val Pro Ser
            180                 185                 190
```

-continued

```
Ser Thr Trp Pro Ser Gln Thr Val Thr Cys Ser Val Ala His Pro Ala
            195                 200                 205

Ser Ser Thr Thr Val Asp Lys Lys Leu Glu Pro Ser Gly Pro Ile Ser
210                 215                 220

Thr Ile Asn Pro Cys Pro Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
            275                 280                 285

Asn Asn Val Glu Val His Thr Ala Gln Thr Gln Thr His Arg Glu Asp
            290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
            325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Ala Glu Gln Leu Ser
            355                 360                 365

Arg Lys Asp Val Ser Leu Thr Cys Leu Val Val Gly Phe Asn Pro Gly
            370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
            405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
            435                 440                 445

Thr Ile Ser Arg Ser Pro Gly Lys
    450                 455
```

<210> SEQ ID NO 2
<211> LENGTH: 213
<212> TYPE: PRT
<213> ORGANISM: Artificial Sequence
<220> FEATURE:
<223> OTHER INFORMATION: SPV-T3a Light Chain

<400> SEQUENCE: 2

```
Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Tr

-continued

```
Phe Gly Ala Gly Thr Lys Leu Glu Leu Lys Arg Ala Asp Ala Ala Pro
                100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 3
<211> LENGTH: 120
<212> TYPE: PRT
<213> ORGANISM: Artificial Sequence
<220> FEATURE:
<223> OTHER INFORMATION: SPV-T3a-VH

<400> SEQUENCE: 3

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Asn Tyr Ile Gln Arg Phe
        50                  55                  60

Lys Asp Lys Ala Thr Leu Thr Ala Asp Lys Ser Ser Ser Thr Ala Tyr
65                  70                  75                  80

Met Gln Val Ser Ser Leu Thr Ser Glu Asp Ser Ala Val Tyr Tyr Cys
                85                  90                  95

Ala Arg Gly Ser Arg Tyr Asp Tyr Tyr Gly Met Asp Tyr Trp Gly Gln
                100                 105                 110

Gly Thr Ser Val Thr Val Ser Ser
            115                 120

<210> SEQ ID NO 4
<211> LENGTH: 107
<212> TYPE: PRT
<213> ORGANISM: Artificial Sequence
<220> FEATURE:
<223> OTHER INFORMATION: SPV-T3a-VL

<400> SEQUENCE: 4

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60
```

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg
            100                 105

<210> SEQ ID NO 5
<211> LENGTH: 8
<212> TYPE: PRT
<213> ORGANISM: Artificial Sequence
<220> FEATURE:
<223> OTHER INFORMATION: SPV-T3a-CDRH1

<400> SEQUENCE: 5

Gly Tyr Thr Phe Thr Ser Tyr Thr
1               5

<210> SEQ ID NO 6
<211> LENGTH: 8
<212> TYPE: PRT
<213> ORGANISM: Artificial Sequence
<220> FEATURE:
<223> OTHER INFORMATION: SPV-T3a-CDRH2

<400> SEQUENCE: 6

Ile Asn Pro Ser Ser Gly Tyr Thr
1               5

<210> SEQ ID NO 7
<211> LENGTH: 13
<212> TYPE: PRT
<213> ORGANISM: Artificial Sequence
<220> FEATURE:
<223> OTHER INFORMATION: SPV-T3a-CDRH3

<400> SEQUENCE: 7

Ala Arg Gly Ser Arg Tyr Asp Tyr Tyr Gly Met Asp Tyr
1               5                   10

<210> SEQ ID NO 8
<211> LENGTH: 5
<212> TYPE: PRT
<213> ORGANISM: Artificial Sequence
<220> FEATURE:
<223> OTHER INFORMATION: SPV-T3a-CDRL1

<400> SEQUENCE: 8

Ser Ser Val Ser Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: SPV-T3a-CDRL2

<400> SEQUENCE: 9

Asp Thr Ser
1

<210> SEQ ID NO 10
<211> LENGTH: 9
<212> TYPE: PRT
```

-continued

<213> ORGANISM: Artificial Sequence
<220> FEATURE:
<223> OTHER INFORMATION: SPV-T3a-CDRL3

<400> SEQUENCE: 10

Gln Gln Trp Ser Ser Asn Pro Leu Thr
1               5

<210> SEQ ID NO 11
<211> LENGTH: 453
<212> TYPE: PRT
<213> ORGANISM: Artificial Sequence
<220> FEATURE:
<223> OTHER INFORMATION: WT1 Heavy Chain

<400> SEQUENCE: 11

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Met Trp Leu
            35                  40                  45

Gly Trp Ile Asn Thr Tyr Thr Gly Glu Pro Thr Tyr Ala Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Ala Tyr Phe Tyr Gly Ser Ser Pro Tyr Phe Phe Asp Tyr
            100                 105                 110

Trp Gly Gln Gly Thr Thr Leu Thr Val Ser Ser Ala Lys Thr Thr Ala
        115                 120                 125

Pro Ser Val Tyr Pro Leu Ala Pro Val Cys Gly Asp Thr Thr Gly Ser
130                 135                 140

Ser Val Thr Leu Gly Cys Leu Val Lys Gly Tyr Phe Pro Glu Pro Val
145                 150                 155                 160

Thr Leu Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190

Val Thr Ser Ser Thr Trp Pro Ser Gln Ser Ile Thr Cys Asn Val Ala
        195                 200                 205

His Pro Ala Ser Ser Thr Lys Val Asp Lys Lys Ile Glu Pro Arg Gly
    210                 215                 220

Pro Thr Ile Lys Pro Cys Pro Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Val Asp Val
            260                 265                 270

Ser Glu Asp Asp Pro Asp Val Gln Ile Ser Trp Phe Val Asn Asn Val
        275                 280                 285

Glu Val His Thr Ala Gln Thr Gln Thr His Arg Glu Asp Tyr Asn Ser
    290                 295                 300

Thr Leu Arg Val Val Ser Ala Leu Pro Ile Gln His Gln Asp Trp Met
305                 310                 315                 320

-continued

```
Ser Gly Lys Glu Phe Lys Cys Lys Val Asn Asn Lys Asp Leu Pro Ala
                325                 330                 335

Pro Ile Glu Arg Thr Ile Ser Lys Pro Lys Gly Ser Val Arg Ala Pro
            340                 345                 350

Gln Val Tyr Val Leu Pro Pro Glu Glu Met Thr Lys Lys Gln
        355                 360                 365

Val Thr Leu Thr Cys Met Val Thr Asp Phe Met Pro Glu Asp Ile Tyr
    370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
                405                 410                 415

Arg Val Glu Lys Lys Asn Trp Val Arg Asn Ser Tyr Ser Cys Ser
            420                 425                 430  Ser

Val Val His Glu Gly Leu His Asn His His Thr Thr Lys Ser Phe Ser
        435                 440                 445

Arg Thr Pro Gly Lys
        450

<210> SEQ ID NO 12
<211> LENGTH: 215
<212> TYPE: PRT
<213> ORGANISM: Artificial Sequence
<220> FEATURE:
<223> OTHER INFORMATION: WT1 Light Chain

<400> SEQUENCE: 12

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Cys Ser Asn
                85                  90                  95

His Leu Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215
```

<210> SEQ ID NO 13
<211> LENGTH: 123
<212> TYPE: PRT
<213> ORGANISM: Artificial Sequence
<220> FEATURE:
<223> OTHER INFORMATION: WT1-VH

<400> SEQUENCE: 13

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Met Trp Leu
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Trp Ala Tyr Phe Tyr Gly Ser Ser Pro Tyr Phe Phe Asp Tyr
            100                 105                 110

Trp Gly Gln Gly Thr Thr Leu Thr Val Ser Ser
        115                 120
```

<210> SEQ ID NO 14
<211> LENGTH: 109
<212> TYPE: PRT
<213> ORGANISM: Artificial Sequence
<220> FEATURE:
<223> OTHER INFORMATION: WT1-VL

<400> SEQUENCE: 14

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Cys Ser Asn
                85                  90                  95

His Leu Val Phe Gly Gly Gly Thr Lys Leu Thr Val Leu
            100                 105
```

<210> SEQ ID NO 15
<211> LENGTH: 8
<212> TYPE: PRT
<213> ORGANISM: Artificial Sequence
<220> FEATURE:
<223> OTHER INFORMATION: WT1-CDRH1

```
<400> SEQUENCE: 15

Gly Tyr Thr Phe Thr Asn Tyr Gly
1               5

<210> SEQ ID NO 16
<211> LENGTH: 8
<212> TYPE: PRT
<213> ORGANISM: Artificial Sequence
<220> FEATURE:
<223> OTHER INFORMATION: WT1-CDRH2

<400> SEQUENCE: 16

Ile Asn Thr Tyr Thr Gly Glu Pro
1               5

<210> SEQ ID NO 17
<211> LENGTH: 16
<212> TYPE: PRT
<213> ORGANISM: Artificial Sequence
<220> FEATURE:
<223> OTHER INFORMATION: WT1-CDRH3

<400> SEQUENCE: 17

Ala Arg Trp Ala Tyr Phe Tyr Gly Ser Ser Pro Tyr Phe Phe Asp Tyr
1               5                   10                  15

<210> SEQ ID NO 18
<211> LENGTH: 9
<212> TYPE: PRT
<213> ORGANISM: Artificial Sequence
<220> FEATURE:
<223> OTHER INFORMATION: WT1-CDRL1

<400> SEQUENCE: 18

Thr Gly Ala Val Thr Thr Ser Asn Tyr
1               5

<210> SEQ ID NO 19
<211> LENGTH: 3
<212> TYPE: PRT
<213> ORGANISM: Artificial Sequence
<220> FEATURE:
<223> OTHER INFORMATION: WT1-CDRL2

<400> SEQUENCE: 19

Gly Thr Asn
1

<210> SEQ ID NO 20
<211> LENGTH: 9
<212> TYPE: PRT
<213> ORGANISM: Artificial Sequence
<220> FEATURE:
<223> OTHER INFORMATION: WT1-CDRL3

<400> SEQUENCE: 20

Ala Leu Trp Cys Ser Asn His Leu Val
1               5
```